(12) United States Patent
Hester, Jr. et al.

(10) Patent No.: US 6,218,413 B1
(45) Date of Patent: Apr. 17, 2001

(54) OXAZOLIDINONE ANTIBACTERIAL AGENTS HAVING A THIOCARBONYL FUNCTIONALITY

(75) Inventors: Jackson B. Hester, Jr., Galesburg; Eldon George Nidy; Salvatore Charges Perricone, both of Kalamazoo; Toni-Jo Poel, Wayland, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/080,751

(22) Filed: May 18, 1998

Related U.S. Application Data

(60) Provisional application No. 60/048,342, filed on May 30, 1997.

(51) Int. Cl.$^7$ .................... A61K 31/42; A61K 31/535; A61K 31/495; C07D 263/04; C07D 413/00
(52) U.S. Cl. .................... 514/376; 514/374; 514/378; 514/382; 514/236.8; 514/255; 548/229; 548/215; 548/240; 544/137; 544/367
(58) Field of Search .................... 548/229, 215, 548/240; 514/376, 374, 378, 382, 236.8, 255; 544/137, 367

(56) References Cited

U.S. PATENT DOCUMENTS 5,627,181  5/1997  Riedl et al. .

FOREIGN PATENT DOCUMENTS

| 19601264 | 7/1997 | (DE) . |
|---|---|---|
| 0127 902 | 12/1984 | (EP) . |
| 0184 170 | 6/1986 | (EP) . |
| 0352 781 | 1/1990 | (EP) . |
| 0359 418 | 3/1990 | (EP) . |
| 0789 025 | 8/1997 | (EP) . |
| WO95/07271 | 3/1995 | (WO) . |
| WO97/14690 | 4/1997 | (WO) . |
| WO98/07708 | 2/1998 | (WO) . |

OTHER PUBLICATIONS

Yosida et al, CA 130: 223265, 1999.*

* cited by examiner

*Primary Examiner*—Deborah C. Lambkin
(74) *Attorney, Agent, or Firm*—Lucy X. Yang

(57) ABSTRACT

The present invention provides compounds of Formula 1

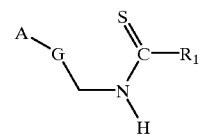

I or pharmaceutical acceptable salts thereof wherein A, G and $R_1$ are as defined in the claims which are antibacterial agents.

15 Claims, No Drawings

OXAZOLIDINONE ANTIBACTERIAL AGENTS HAVING A THIOCARBONYL FUNCTIONALITY

CROSS-REFERENCE TO RELATED APPLICATIONS

This application claims the benefit of the following provisional application: U.S. Ser. No. 60/048,342, filed May 30, 1997, under 35 USC 119(e)(i).

BACKGROUND OF THE INVENTION

The present invention relates to new and useful oxazolidinone compounds and their preparations, and more particularly to oxazolidinone compounds in which the carbonyl functionality of —NH—C(O)—R is converted to a thiocarbonyl functionality, such as a thiourea —NH—C(S)—NH$_2$, an alkyl thiourea —NH—C(S)—NH—(C$_{1-4}$ alkyl), thioamide —NH—C(S)—(C$_{1-4}$ alkyl) or —NH—C(S)—H.

Replacement of the oxygen atom with a sulfur atom has unexpectedly improved the antimicrobial properties of the compounds. The compounds are useful antimicrobial agents, effective against a number of human and veterinary pathogens, including Gram-positive aerobic bacteria such as multiply-resistant staphylococci and streptococci, Gram-negative organisms such as *H. influenzae* and *M. catarrahlis* as well as anaerobic organisms such as bacteroides and clostridia species, and acid-fast organisms such as *Mycobacterium tuberculosis* and *Mycobacterium avium*. The compounds are particularly useful because they are effective against the latter organisms which are known to be responsible for infection in persons with AIDS.

SUMMARY OF THE INVENTION

In one aspect the subject invention is a compound of the Formula I

I

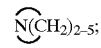

or pharmaceutical acceptable salts thereof wherein:
G is

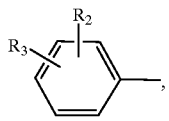

R$_1$ is
a) H,
b) NH$_2$,
c) NH—C$_{1-4}$ alkyl,
d) C$_{1-4}$ alkyl,
e) —OC$_{1-4}$ alkyl,
f) —S C$_{1-4}$ alkyl,
g) C$_{1-4}$ alkyl substituted with 1–3 F, 1–2 Cl, CN or —COOC$_{1-4}$ alkyl,
h) C$_{3-6}$ cycloalkyl,
i) N(C$_{1-4}$ alkyl)$_2$ or j)

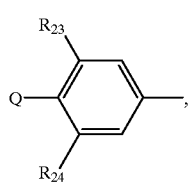

A is
a)

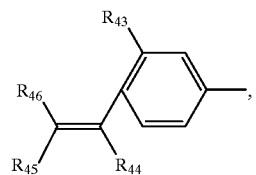

b)

R$_{23}$
Q—
R$_{24}$ c)

R$_{43}$
R$_{46}$
R$_{45}$ R$_{44}$ d) a 5-membered heteroaromatic moiety having one to three atoms selected from the group consisting of S, N, and O,
wherein the 5-membered heteroaromatic moiety is bonded via a carbon atom,
wherein the 5-membered heteroaromatic moiety can additionally have a fused-on benzene or naphthyl ring,
wherein the heteroaromatic moiety is optionally substituted with one to three R$_{48}$, e) a 6-membered heteroaromatic moiety having at least one nitrogen atom,
wherein the heteroaromatic moiety is bonded via a carbon atom,
wherein the 6-membered heteroaromatic moiety can additionally have a fused-on benzene or naphthyl ring,
wherein the heteroaromatic moiety is optionally substituted with one to three R$_{55}$, f) a β-carbolin-3-yl, or indolizinyl bonded via the 6-membered ring, optionally substituted with one to three R$_{55}$, g)

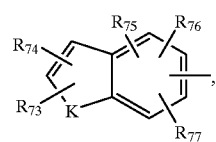

h)

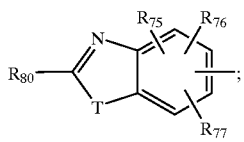

wherein $R_2$ is
a) H,
b) F,
c) Cl,
d) Br,
e) $C_{1-3}$ alkyl,
f) $NO_2$, or
g) $R_2$ and $R_3$ taken together are $-O-(CH_2)_h-O-$;
$R_3$ is
a) $-S(=O)_iR_4$,
b) $-S(=O)_2-N=S(O)_jR_5R_6$,
c) $-SC(=O)R_7$,
d) $-C(=O)R_8$,
e) $-C(=O)R_9$,
f) $-C(=O)NR_{10}R_{11}$,
g) $-C(=NR_{12})R_8$,
h) $-C(R_8)(R_{11})-OR_{13}$,
i) $-C(R_9)(R_{11})-OR_{13}$,
j) $-C(R_8)(R_{11})-OC(=O)R_{13}$,
k) $-C(R_9)(R_{11})-OC(=O)R_{13}$,
l) $-NR_{10}R_{11}$,
m) $-N(R_{10})-C(=O)R_7$,
n) $-N(R_{10})-S(=O)_iR_7$,
o) $-C(OR_{14})(OR_{15})R_8$,
p) $-C(R_8)(R_{16})-NR_{10}R_{11}$, or
q) $C_{1-8}$ alkyl substituted with one or more $=O$ other than at alpha position, $-S(=O)_iR_{17}$, $-NR_{10}R_{11}$, $C_{2-5}$ alkenyl, or $C_{2-5}$ alkynyl;
$R_4$ is
a) $C_{1-4}$ alkyl optionally substituted with one or more halos, OH, CN, $NR_{10}R_{11}$, or $-CO_2R_{13}$,
b) $C_{2-4}$ alkenyl,
c) $-NR_{16}R_{18}$,
d) $-N_3$,
e) $-NHC(=O)R_7$,
f) $-NR_{20}C(=O)R_7$,
g) $-N(R_{19})_2$,
h) $-NR_{16}R_{19}$, or
i) $-NR_{19}R_{20}$;
$R_5$ and $R_6$ at each occurrence are the same or different and are
a) $C_{1-2}$ alkyl, or
b) $R_5$ and $R_6$ taken together are $-(CH_2)_k-$;
$R_7$ is $C_{1-4}$ alkyl optionally substituted with one or more halos;
$R_8$ is
a) H, or
b) $C_{1-8}$ alkyl optionally substituted with one or more halos, or $C_{3-8}$ cycloalkyl;
$R_9$ is $C_{1-4}$ alkyl substituted with one or more
a) $-S(=O)R_{17}$,
b) $-OR_{13}$,
c) $-OC(=O)R_{13}$,
d) $-NR_{10}R_{11}$, or
e) $C_{1-5}$ alkenyl optionally substituted with CHO;
$R_{10}$ and $R_{11}$ at each occurrence are the same or different and are
a) H,
b) $C_{1-4}$ alkyl, or
c) $C_{3-8}$ cycloalkyl;
$R_{12}$ is
a) $-NR_{10}R_{11}$,
b) $-OR_{10}$; or
c) $-NHC(=O)R_{10}$;
$R_{13}$ is
a) H, or
b) $C_{1-4}$ alkyl;
$R_{14}$ and $R_{15}$ at each occurrence are the same or different and are
a) $C_{1-4}$ alkyl, or
b) $R_{14}$ and $R_{15}$ taken together are $-(CH)_1-$;
R is
a) H,
b) $C_{1-4}$ alkyl, or
c) $C_{3-8}$ cycloalkyl;
$R_{17}$ is
a) $C_{1-4}$ alkyl, or
b) $C_{3-8}$ cycloalkyl;
$R_{18}$ is
a) H,
b) $C_{1-4}$ alkyl,
c) $C_{2-4}$ alkenyl,
d) $C_{3-4}$ cycloalkyl,
e) $-OR_{13}$ or
f) $-NR_{21}R_{22}$;
$R_{19}$ is
a) Cl,
b) Br, or
c) I;
$R_{20}$ is a physiologically acceptable cation;
$R_{21}$ and $R_{22}$ at each occurrence are the same or different and are
a) H,
b) $C_{1-4}$ alkyl, or
c) $-NR_{21}R_{22}$ taken together are $-(CH_2)_m-$;
wherein $R_{23}$ and $R_{24}$ at each occurrence are the same or different and are
a) H,
b) F,
c) Cl,
d) $C_{1-2}$ alkyl,
e) CN
f) OH,
g) $C_{1-2}$ alkoxy,
h) nitro, or
i) amino;
Q is a) 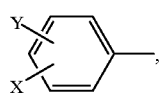
b) 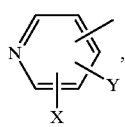
c) 
d) 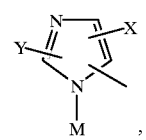
e) 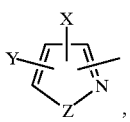
f) 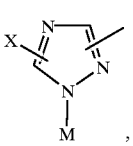
g) 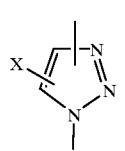
h) 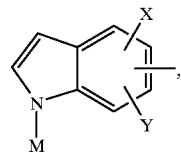
i) 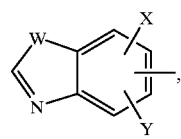
j) 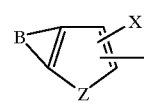
k) 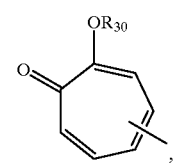
l) 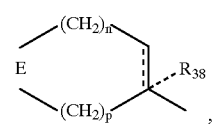
m) a diazinyl group optionally substituted with X and Y,
n) a triazinyl group optionally substituted with X and Y,
o) a quinolinyl group optionally substituted with X and Y,
p) a quinoxalinyl group optionally substituted with X and Y,
q) a naphthyridinyl group optionally substituted with X and Y,
r) 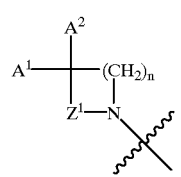

s) 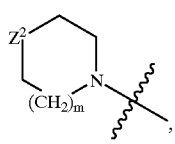
t) 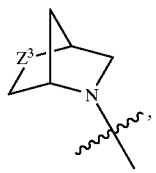
u) 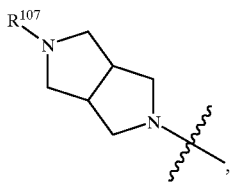
v) 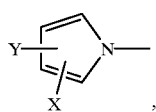
w) 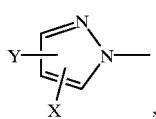
x) 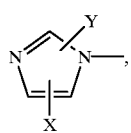
y) 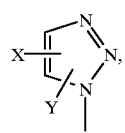
z) 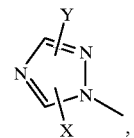
aa) 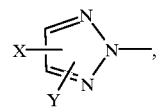
bb) 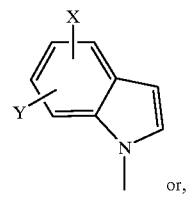
or,
Q and $R_{24}$ taken together are
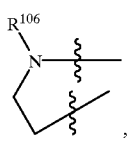
wherein $Z^1$ is
a) —CH$_2$—,
b) —CH(R$^{104}$)—CH$_2$—,
c) —C(O)—, or
d) —CH$_2$CH$_2$CH$_2$—;
wherein $Z^2$ is
a) —O$_2$S—,
b) —O—,
c) —N(R$^{107}$)—,
d) —OS—, or
e) —S—;
wherein $Z^3$ is
a) —O$_2$S—,
b) —O—,
c) —OS—, or
d) —S—;
wherein $A^1$ is
a) H—, or
b) CH$_3$;
wherein $A^2$ is
a) H—,
b) HO—,
c) CH$_3$—,
d) CH$_3$O—,
e) R$^{102}$O—CH$_2$—C(O)—NH—,
f) R$^{103}$O—C(O)—NH—, g) (C₁–C₂)alkyl—O—C(O)—,
h) HO—CH₂—,
i) CH₃O—NH—,
j) (C₁–C₃)alkyl—O₂C—
k) CH₃—C(O)—,
l) CH₃—C(O)—CH₂—,
m)

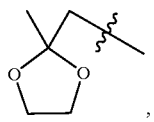
, n)

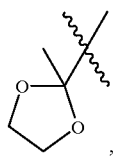
,

A¹ and A² taken together are:
a)

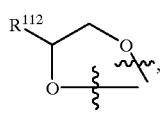

b) O=, or
c)

;

wherein R¹⁰² is
 a) H—,
 b) CH₃—,
 c) phenyl-CH₂—, or
 d) CH₃C(O)—;
wherein R¹⁰³ is
 a) (C₁–C₃)alkyl-, or
 b) phenyl-;
wherein R¹⁰⁴ is
 a) H—, or
 b) HO—;
wherein R¹⁰⁵ is
 a) H—,
 b) (C₁–C₃)alkyl-,
 c) CH₂=CH—CH₂—, or
 d) CH₃—O—(CH₂)₂—;
wherein R¹⁰⁶ is
 a) CH₃—C(O)—,
 b) H—C(O)—,
 c) Cl₂CH—C(O)—,
 d) HOCH₂—C(O)—,
 e) CH₃SO₂—, f)

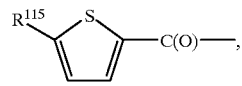
, g) F₂CHC(O)—,
h)

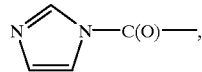
, i) H₃C—C(O)—O—CH₂—C(O)—,
j) H—C(O)—O—CH₂—C(O)—,
k)

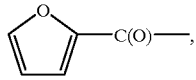
, l) HC≡C—CH₂O—CH₂—C(O)—, or
m) phenyl-CH₂—O—CH₂—C(O)—;
wherein R¹⁰⁷ is
 a) R¹⁰²O—C(R₁₁₀)(R₁₁₁)—C(O)—,
 b) R¹⁰³O—C(O)—,
 c) R¹⁰⁸—C(O)—,
 d)

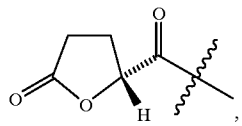
, e)

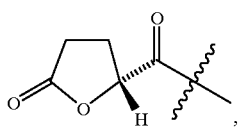
, f) H₃C—C(O)—(CH₂)₂—C(O)—,
g) R¹⁰⁹—SO₂—,
h)

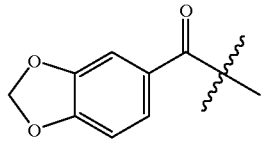
, i) HO—CH₂—C(O)—,
j) R¹¹⁶—(CH₂)₂—,
k) R¹¹³—C(O)—O—CH₂—C(O)—,
l) (CH₃)₂N—CH₂—C(O)—NH—,
m) NC—CH₂—, or
n) F₂—CH—CH₂—;

wherein $R^{108}$ is
  a) H—,
  b) $(C_1–C_4)$alkyl,
  c) aryl-$(CH_2)_p$,
  d) $ClH_2C$—,
  e) $Cl_2HC$—,
  f) $FH_2C$—,
  g) $F_2HC$—, or
  h) $(C_3–C_6)$cycloalkyl;
wherein $R^{109}$ is
  a) —$CH_3$,
  b) —$CH_2Cl$,
  c) —$CH_2CH=CH_2$,
  d) aryl, or
  e) —$CH_2CN$;
wherein $R^{110}$ and $R^{111}$ are independently
  a) H—,
  b) $CH_3$—; or
wherein $R^{112}$ is
  a) H—,
  b) $CH_3O—CH_2O—CH_2$—, or
  c) $HOCH_2$—;
wherein $R^{113}$ is
  a) $CH_3$—,
  b) $HOCH_2$—,
  c) $(CH_3)_2N$-phenyl, or
  d) $(CH_3)_2N—CH_2$—;
wherein $R^{114}$ is
  a) HO—,
  b) $CH_3O$—,
  c) $H_2N$—,
  d) $CH_3O—C(O)—O$—,
  e) $CH_3—C(O)—O—CH_2—C(O)—O$—,
  f) phenyl-$CH_2—O—CH_2—C(O)—O$—,
  g) HO—$(CH_2)_2—O$—,
  h) $CH_3O—CH_2—O—(CH_2)_2—O$—, or
  i) $CH_3O—CH_2—O$—; wherein $R^{113}$ is
  a) $CH_3$—,
  b) $HOCH_2$—,
  c) $(CH_3)_2N$-phenyl, or
  d) $(CH_3)_2N—CH_2$—;
wherein $R^{115}$ is
  a) H—, or
  b) Cl—;
wherein $R^{116}$ is
  a) HO—
  b) $CH_3O$—, or
  c) F;
B is an unsaturated 4-atom linker having one nitrogen and three carbons;
M is
  a) H,
  b) $C_{1-8}$ alkyl,
  c) $C_{3-8}$ cycloalkyl,
  d) —$(CH_2)_mOR_{13}$, or
  e) —$(CH_2)_h—NR_{21}R_{22}$;
Z is
  a) O,
  b) S, or
  c) NM;
W is
  a) CH,
  b) N, or
  c) S or O when Z is NM;
Y is
  a) H,
  b) F,
  c) Cl,
  d) Br,
  e) $C_{1-3}$ alkyl, or
  f) $NO_2$;
X is
  a) H,
  b) —CN,
  c) $OR_{27}$,
  d) halo,
  e) $NO_2$,
  f) tetrazoyl,
  g) —SH,
  h) —$S(=O)_iR_4$,
  i) —$S(=O)_2—N=S(O)_jR_5R_6$,
  j) —$SC(=O)R_7$,
  k) —$C(=O)R_{25}$,
  l) —$C(=O)NR_{27}R_{28}$,
  m) —$C(=NR_{29})R_{25}$,
  n) —$C(R_{25})(R_{28})—OR_{13}$,
  o) —$C(R_{25})(R_{28})—OC(=O)R_{13}$,
  p) —$C(R_{28})(OR_{13})—(CH_2)_h—NR_{27}R_{28}$,
  q) —$NR_{27}R_{28}$,
  r) —$N(R_{27})C(=O)R_7$,
  s) —$N(R_{27})—S(=O)_iR_7$,
  t) —$C(OR_{14})(OR_{15})R_{28}$,
  u) —$C(R_{25})(R_{16})—NR_{27}R_{26}$, or
  v) $C_{1-8}$ alkyl substituted with one or more halos, OH, =O other than at apha position, —$S(=O)_iR_{17}$, —$NR_{27}R_{28}$, $C_{2-5}$ alkenyl, $C_{2-5}$ alkynyl or $C_{3-8}$ cycloalkyl;
$R_4$, $R_5$, $R_6$, $R_7$, $R_{13}$, $R_{14}$, $R_{15}$, $R_{16}$, and $R_{17}$ are the same as defined above;
$R_{25}$ is
  a) H,
  b) $C_{1-8}$ alkyl optionally substituted with one or more halos, $C_{3-8}$ cycloalkyl, $C_{1-4}$ alkyl substituted with one or more of —$S(=O)_iR_{17}$, —$OR_{13}$, or $OC(=O)R_{13}$, $NR_{27}R_{28}$, or
  c) $C_{2-5}$ alkenyl optionally substituted with CHO, or $CO_2R_{13}$;
$R_{26}$ is
  a) $R_{28}$, or
  b) $NR_{27}N_{28}$;
$R_{27}$ and $R_{28}$ at each occurrence are the same or different and are
  a) H,
  b) $C_{1-8}$ alkyl,
  c) $C_{3-8}$ cycloalkyl,
  d) —$(CH_2)_mOR_{13}$,
  e) —$(CH_2)_h—NR_{21}R_{22}$, or
  f) $R_{27}$ and $R_{28}$ taken together are —$(CH_2)_2O(CH_2)_2$—, —$(CH_2)_hCH(COR_7)$—, or —$(CH_2)_2N(CH_2)_2(R_7)$;

$R_{29}$ is
  a) —$NR_{27}R_{28}$,
  b) —$OR_{27}$, or
  c) —$NHC(=O)R_{28}$;
wherein $R_{30}$ is
  a) H,
  b) $C_{1-8}$ alkyl optionally substituted with one or more halos, or
  c) $C_{1-8}$ alkyl optionally substituted with one or more OH, or $C_{1-6}$ alkoxy;
wherein E is
  a) $NR_{39}$,
  b) —$S(=O)_i$, or
  c) O;
$R_{38}$ is
  a) H,
  b) $C_{1-6}$ alkyl,
  c) —$(CH_2)_q$-aryl, or
  d) halo;
$R_{39}$ is
  a) H,
  b) $C_{1-6}$ alkyl optionally substituted with one or more OH, halo, or —CN,
  c) —$(CH_2)_q$-aryl,
  d) —$CO_2R_{40}$,
  e) —$COR_{41}$,
  f) —$C(=O)-(CH_2)_q-C(=O)R_{40}$,
  g) —$S(=O)_2-C_{1-6}$ alkyl,
  h) —$S(=O)_2-(CH_2)_q$-aryl, or
  i) —$(C=O)_j$-Het;
$R_{40}$ is
  a) H,
  b) $C_{1-6}$ alkyl optionally substituted with one or more OH, halo, or —CN,
  c) —$(CH_2)_q$-aryl, or
  d) —$(CH_2)_q$—$OR_{42}$;
$R_{41}$ is
  a) $C_{1-6}$ alkyl optionally substituted with one or more OH, halo, or —CN,
  b) —$(CH_2)_q$-aryl, or
  c) —$(CH_2)_q$-$OR_{42}$;
$R_{42}$ is
  a) H,
  b) $C_{1-6}$ alkyl,
  c) —$(CH_2)_q$-aryl, or
  d) —$C(=O)$—$C_{1-6}$ alkyl;
aryl is
  a) phenyl,
  b) pyridyl, or
  c) napthyl; a to c optionally substituted with one or more halo, —CN, OH, SH, $C_{1-6}$ alkyl, $C_{1-6}$ alkoxy, or $C_{1-6}$ alkylthio;
wherein $R_{43}$ is
  a) H,
  b) $C_{1-2}$ alkyl,
  c) F, or
  d) OH;
$R_{44}$ is
  a) H,
  b) $CF_3$,
  c) $C_{1-3}$ alkyl optionally substituted with one or more halo,
  d) phenyl optionally substituted with one or more halo,
  e) $R_{44}$ and $R_{45}$ taken together are a 5-, 6-, or 7-membered ring of the formula,
or

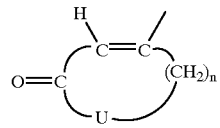

f) $R_{44}$ and $R_{45}$ taken together are —$(CH_2)_k$—, when $R_{46}$ is an electron-withdrawing group;
$R_{45}$ and $R_{46}$ at each occurrence are the same or different and are
  a) an electron-withdrawing group,
  b) H,
  c) $CF_3$,
  d) $C_{1-3}$ alkyl optionally substituted with one halo,
  e) phenyl, provided at least one of $R_{45}$ or $R_{46}$ is an electron-withdrawing group, or
  f) $R_{45}$ and $R_{46}$ taken together are a 5-, 6-, 7-membered ring of the formula

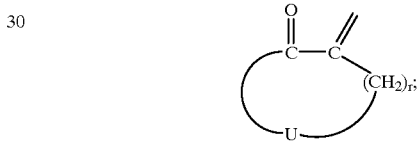

U is
  a) $CH_2$,
  b) O,
  c) S, or
  d) $NR_{47}$;
$R_{47}$ is
  a) H, or
  b) $C_{1-5}$ alkyl;
wherein $R_{48}$ is
  a) carboxyl,
  b) halo,
  c) —CN,
  d) mercapto,
  e) formyl,
  f) $CF_3$,
  g) —$NO_2$,
  h) $C_{1-6}$ alkoxy,
  i) $C_{1-6}$ alkoxycarbonyl,
  j) $C_{1-6}$ alkythio,
  k) $C_{1-6}$ acyl,
  l) —$NR_{49}R_{50}$,
  m) $C_{1-6}$ alkyl optionally substituted with OH, $C_{1-5}$ alkoxy, $C_{1-5}$ acyl, or —$NR_{49}R_{50}$,
  n) $C_{2-8}$ alkenylphenyl optionally substituted with one or two $R_{51}$,
  o) phenyl optionally substituted with one or two $R_{51}$,
  p) a 5-, or 6-membered (un)saturated heterocyclic moiety having one to three atoms selected from the group consisting of S, N, and O, optionally substituted with one or two $R_{51}$, or q)

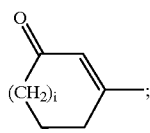

$R_{49}$ and $R_{50}$ at each occurrence are the same or different and are
a) H,
b) $C_{1-4}$ alkyl,
c) $C_{5-6}$ cycloalkyl, or
d) $R_{49}$ and $R_{50}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, $C_{1-3}$ alkyl, or $C_{1-3}$ acyl; $R_{51}$ is
a) carboxyl,
b) halo,
c) —CN,
d) mercapto,
e) formyl,
f) $CF_3$,
g) —$NO_2$, h) $C_{1-6}$ alkoxy, i) $C_{1-6}$ alkoxycarbonyl, j) $C_{1-6}$ alkythio, k) $C_{1-6}$ acyl,
l) $C_{1-6}$ alkyl optionally substituted with OH, $C_{1-5}$ alkoxy, $C_{1-5}$ acyl, or —$NR_{49}R_{50}$,
m) phenyl,
n) —C(=O)$NR_{52}R_{53}$,
o) —$NR_{49}R_{50}$,
p) —N($R_{52}$)(—$SO_2R_{54}$),
q) —$SO_2$—$NR_{52}R_{53}$, or
r) —S(=O)$_iR_{54}$;
$R_{52}$ and $R_{53}$ at each occurrence are the same or different and are
a) H,
b) $C_{1-6}$ alkyl, or
c) phenyl;
$R_{54}$ is
a) $C_{1-4}$ alkyl, or
b) phenyl optionally substituted with $C_{1-4}$ alkyl;
wherein $R_{55}$ is
a) carboxyl,
b) halo,
c) —CN,
d) mercapto,
e) formyl,
f) $CF_3$,
g) —$NO_2$,
h) $C_{1-6}$ alkoxy,
i) $C_{1-6}$ alkoxycarbonyl,
j) $C_{1-6}$ alkythio
k) $C_{1-6}$ acyl,
l) —$NR_{56}R_{57}$,
m) $C_{1-6}$ alkyl optionally substituted with OH, $C_{1-5}$ alkoxy, $C_{1-5}$ acyl, or —$NR_{56}R_{57}$, n) $C_{2-8}$ alkenylphenyl optionally substituted with one or two $R_{58}$,
o) phenyl optionally substituted with one or two $R_{58}$,
p) a 5- or 6-membered (un)saturated heterocyclic moiety having one ta, three atoms selected from the group consisting of S, N, and O, optionally substituted with one or two $R_{58}$, or q)

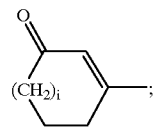

$R_{56}$ and $R_{57}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl, or
g) $R_{56}$ and $R_{57}$ taken together with the nitrogen atom is a 5-, 6-membered saturated heterocyclic moiety which optionally has a further hetero atom selected from the group consisting of S, N, and O and can in turn be optionally substituted with, including on the further nitrogen atom, phenyl, pyrimidyl, $C_{1-3}$ alkyl, or $C_{1-3}$ acyl;
$R_{58}$ is
a) carboxyl,
b) halo,
c) —CN,
d) mercapto,
e) formyl,
f) $CF_3$,
g) —$NO_2$,
h) $C_{1-6}$ alkoxy,
i) $C_{1-6}$ alkoxycarbonyl,
j) $C_{1-6}$ alkythio,
k) $C_{1-6}$ acyl,
l) phenyl,
m) $C_{1-6}$ alkyl optionally substituted with OH, azido, $C_{1-5}$ alkoxy, $C_{1-5}$ acyl, —$NR_{65}R_{66}$, —$SR_{67}$, O—$SO_2R_{68}$, or

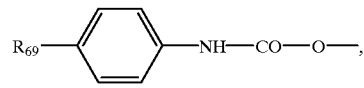

n) —C(=O)$NR_{59}R_{60}$,
o) —$NR_{56}R_{57}$,
p) —N($R_{59}$)(—$SO_2R_{54}$),
q) —$SO_2$—$NR_{59}R_{60}$,
r) —S(=O)$_iR_{54}$,
s) —CH=N—$R_{61}$, or
t) —CH(OH)—$SO_3R_{64}$;
$R_{54}$ is the same as defined above;
$R_{59}$ and $R_{60}$ at each occurrence are the same or different and are a) H,
b) $C_{1-6}$ alkyl,
c) phenyl, or
d) tolyl;
$R_{61}$ is
a) OH,
b) benzyloxy,
c) —NH—C(=O)—NH$_2$,
d) —NH—C(=S)—NH$_2$, or
e) —NH—C(=NH)—NR$_{62}$R$_{63}$;
$R_{62}$ and $R_{63}$ at each occurrence are the same or different and are
a) H, or
b) $C_{1-4}$ alkyl optionally substituted with phenyl or pyridyl;
$R_{64}$ is
a) H, or
b) a sodium ion;
$R_{65}$ and $R_{66}$ at each occurrence are the same or different and are
a) H,
b) formyl,
c) $C_{1-4}$ alkyl,
d) $C_{1-4}$ acyl,
e) phenyl,
f) $C_{3-6}$ cycloalkyl,
g) $R_{65}$ and $R_{66}$ taken together are a 5-, 6-membered saturated heterocyclic moiety having one to three atoms selected from the group consisting of S, N, and O, optionally substituted with, including on the nitrogen atom, phenyl, pyrimidyl, $C_{1-3}$ alkyl, or $C_{1-3}$ acyl,
h) —P(O)(OR$_{70}$)(OR$_{71}$), or
i) —SO$_2$—R$_{72}$;
$R_{67}$ is

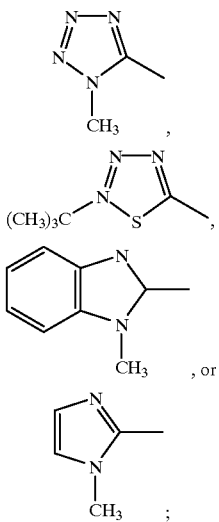

$R_{68}$ is $C_{1-3}$ alkyl;
$R_{69}$ is
a) $C_{1-6}$ alkoxycarbonyl, or
b) carboxyl;
$R_{70}$ and $R_{71}$ at each occurrence are the same or different and are a) H, or
b) $C_{1-3}$ alkyl;
$R_{72}$ is
a) methyl,
b) phenyl, or
c) tolyl;
wherein K is
a) O, or
b) S;
$R_{73}$, $R_{74}$, $R_{75}$, $R_{76}$, and $R_{77}$ at each occurrence are the same or different and are
a) H,
b) carboxyl,
c) halo,
d) —CN,
e) mercapto,
f) formyl,
g) CF$_3$,
h) —NO$_2$,
i) $C_{1-6}$ alkoxy,
j) $C_{1-6}$ alkoxycarbonyl,
k) $C_{1-6}$ alkythio,
l) $C_{1-6}$ acyl,
m) —NR$_{78}$R$_{79}$,
n) $C_{1-6}$ alkyl optionally substituted with OH, $C_{1-5}$ alkoxy, $C_{1-5}$ acyl, —NR$_{78}$R$_{79}$, —N(phenyl)(CH$_2$—CH$_2$—OH), —O—CH(CH$_3$)(OCH$_2$CH$_3$), or —O—phenyl-[para-NHC(=O)CH$_3$],
o) $C_{2-8}$ alkenylphenyl optionally substituted with $R_{51}$,
p) phenyl optionally substituted with $R_{51}$, or
q) a 5-, or 6-membered (un)saturated heterocyclic moiety having one to three atoms selected from the group consisting of S, N, and O, optionally substituted with $R_{51}$;
$R_{51}$ is the same as defined above;
$R_{78}$ and $R_{79}$ at each occurrence are the same or different and are
a) H,
b) $C_{1-4}$ alkyl,
c) phenyl, or
d) $R_{78}$ and $R_{79}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, $C_{1-3}$ alkyl, or $C_{1-3}$ acyl;
wherein T is
a) O,
b) S, or
c) SO$_2$;
$R_{75}$, $R_{76}$, and $R_{77}$ are the same as defined above;
$R_{80}$ is
a) H,
b) formyl,
c) carboxyl,
d) $C_{1-6}$ alkoxycarbonyl,
e) $C_{1-8}$ alkyl,
f) $C_{2-8}$ alkenyl,
wherein the substituents (e) and (f) can be optionally substituted with OH, halo, $C_{1-6}$ alkoxy, $C_{1-6}$ acyl, $C_{1-6}$ alkylthio or $C_{1-6}$ alkoxycarbonyl, or phenyl optionally substituted with halo, g) an aromatic moiety having 6 to 10 carbon atoms optionally substituted with carboxyl, halo, —CN, formyl, $CF_3$, —$NO_2$, $C_{1-6}$ alkyl, $C_{1-6}$ alkoxy, $C_{1-6}$ acyl, $C_{1-6}$ alkylthio, or $C_{1-6}$ alkoxycarbonyl;

h) —$NR_{81}R_{82}$, i) —$OR_{90}$, j) —$S(=O)_j$—$R_{91}$, k) —$SO_2$—$N(R_{92})(R_{93})$, or l) a radical of the following formulas:

$R_{81}$ and $R_{82}$ at each occurrence are the same or different and are a) H, b) $C_{3-6}$ cycloalkyl, c) phenyl, d) $C_{1-6}$ acyl, e) $C_{1-8}$ alkyl optionally substituted with OH, $C_{1-6}$ alkoxy which can be substituted with OH, a 5-, or 6-membered aromatic heterocyclic moiety having one to three atoms selected from the group consisting of S, N, and O, phenyl optionally substituted with OH, $CF_3$, halo, —$NO_2$, $C_{1-4}$ alkoxy, —$NR_{83}R_{84}$, or

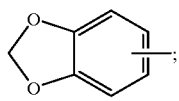

f)

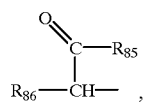

g)

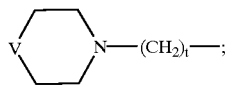

V is a) O, b) $CH_2$, or c) $NR_{87}$;

$R_{83}$ and $R_{84}$ at each occurrence are the same or different and are a) H, or b) $C_{1-4}$ alkyl;

$R_{85}$ is a) OH, b) $C_{1-4}$ alkoxy, or

C) —$NR_{88} R_{89}$;

$R_{86}$ is a) H, or b) $C_{1-7}$ alkyl optionally substituted with indolyl, OH, mercaptyl, imidazoly, methylthio, amino, phenyl optionally substituted with OH, —C(=O)—$NH_2$, —$CO_2H$, or —C(=NH)—$NH_2$;

$R_{87}$ is a) H, b) phenyl, or c) $C_{1-6}$ alkyl optionally substituted by OH;

$R_{88}$ and $R_{89}$ at each occurrence are the same or different and are a) H, b) $C_{1-5}$ alkyl c) $C_{3-6}$ cycloalky, or d) phenyl;

$R_{90}$ is a) $C_{1-8}$ alkyl optionally substituted with $C_{1-6}$ alkoxy or $C_{1-6}$ hydroxy, $C_{3-6}$ cycloalkyl, a 6-membered aromatic optionally benzo-fused heterocyclic moiety having one to three nitrogen atoms, which can in turn be substituted with one or two —$NO_2$, $CF_3$, halo, —CN, OH, $C_{1-5}$ alkyl, $C_{1-5}$ alkoxy, or $C_{1-5}$ acyl;

b)

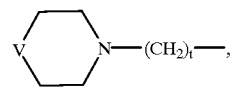

c) phenyl, or d) pyridyl;

$R_{91}$ is a) $C_{1-16}$ alkyl, b) $C_{2-16}$ alkenyl, wherein the substituents (a) and (b) can be optionally substituted swith $C_{1-6}$ alkoxycarbonyl, or a 5-, 6-, 7-membered aromatic heterocyclic moiety having one to three atoms selected from the group consisting of S, N, and O, c) an aromatic moiety having 6 to 10 carbon atoms, or d) a 5-, 6-, 7-membered aromatic heterocyclic moiety having one to three atoms selected from the group consisting of S, N, and O, wherein the substituents (c) and (d) can be optionally substituted with carboxyl, halo, —CN, formyl, $CF_3$, —$NO_2$, $C_{1-6}$ alkyl, $C_{1-6}$ alkoxy, $C_{1-6}$ acyl, $C_{1-6}$ alkylthio, or $C_{1-6}$ alkoxycarbonyl;

$R_{92}$ and $R_{93}$ at each occurrence are the same or different and are a) H, b) phenyl, c) $C_{1-6}$ alkyl, or d) benzyl;

$R_{94}$ and $R_{95}$ at each occurrence are the same or different and are a) H, b) OH, c) $C_{1-6}$ alkyl optionally substituted with —$NR_{83} R_{84}$, or d) $R_{94}$ and $R_{95}$ taken together are =O;

$R_{96}$ is a) an aromatic moiety having 6 to 10 carbon atoms, b) a 5-, or 6-membered aromatic optionally benzo-fused heterocyclic moiety having one to three atoms selected from the group consisting of S, N, and O, wherein the substituents (a) and (b) which can in turn be substituted with one or three —$NO_2$, $CF_3$, halo, —CN, OH, phenyl, $C_{1-5}$ alkyl, $C_{1-5}$ alkoxy, or $C_{1-5}$ acyl, c) morpholinyl, d) OH, e) C$_{1-6}$ alkoxy,
f) —NR$_{83}$R$_{84}$,
g) —C(=O)—R$_{97}$, or
h)

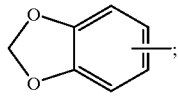

R$_{97}$ is
  a) morpholinyl,
  b) OH, or
  c) C$_{1-6}$ alkoxy;
h is 1, 2, or 3;
i is 0, 1, or 2;
j is 0 or 1;
k is 3, 4, or 5;
l is 2 or 3;
m is 4 or 5;
n is 0, 1, 2, 3, 4, or 5;
p is 0, 1, 2, 3, 4, or 5; with the proviso that n and p together are 1, 2, 3, 4, or 5;
q is 1, 2, 3, or 4;
r is 2, 3, or 4;
t is 0, 1, 2, 3, 4, 5, or 6;
u is 1 or 2.

DETAILED DESCRIPTION OF THE INVENTION

The new compounds of the invention can be prepared using known compounds and intermediates of oxzolidinones, isoxazolines and butyolactones as intermediates and synthetic methods known in the art. Thioamides of the invention can typically be prepared by the reaction of the corresponding arnide with Lawesson's reagent.

Compounds disclosed in the following publications are suitable intermediates for preparation of the compounds of this invention and are hereby incorporated by reference for their disclosure of suitable compounds that can be converted to the subject thiocarbonyl derivatives.

U.S. Pat. Nos. 5,225,565; 5,182,403; 5,164,510; 5,247,090; 5,231,188; 5,565,571; 5,547,950; and 5,523,403.

PCT Application and publications PCT/US93/04850, WO94/01110; PCT/US94/08904, WO95/07271; PCT/US95/02972, WO95/25106; PCT/JUS95/10992, WO96/13502; PCT/US96/05202, WO96/35691; PCT/US96/12766; PCT[US96/13726; PCT/US96/14135; PCT/US96/17120; PCT/US96/19149; PCT/US97/01970; PCT/US95/12751, WO96/15130; and PCTJUS96/00718, WO96/23788.

Chemical conversion techniques for converting various intermediates having a CH$_2$NH$_2$ on the oxazolidinone ring to CH$_2$NH—C(S)—CH$_3$ is disclosed by Hartke, K., Barrmeyer, S., J. prakt. Chem. 1996, 338, 251–6. Similarly, conversion of CH$_2$NHC(=O)CH$_3$ to CH$_2$NHC(S)NHCH$_3$ is reported by Cava, M. P.; Levinson, M. I., Thionation Reactions of Lawesson's Reagents, Tetrahedron 1985, 41, 5061–87.

For the purpose of the present invention, the carbon content of various hydrocarbon containing moieties is indicated by a prefix designating the minimium and maximum number of carbon atoms in the moiety, i.e., the prefix C$_{i-j}$ defines the number of carbon atoms present from the integer "i" to the integer "j", inclusive, Thus, C$_{1-4}$ alkyl refers to alkyl of 1–4 carbon atoms, inclusive, or methyl, ethyl, propyl, butyl and isomeric forms thereof.

The terms "C$_{1-2}$ alkyl", "C$_{1-3}$ alkyl", "C$_{1-4}$ alkyl", "C$_{1-5}$ alkyl", "C$_{1-6}$ alkyl", "C$_{1-8}$ alkyl", and "C$_{1-16}$ alkyl" refer to an alkyl group having one to two, one to three, one to four, one to five, one to six, one to eight, or one to sixteen carbon atoms respectively such as, for example, methyl, ethyl, propyl, butyl, pentyl, hexyl, heptyl, octyl, nonyl, decyl, undecyl, dodecyl, tridecyl, tetradecyl and their isomeric forms thereof.

The terms "C$_{2-4}$ alkenyl", "C$_{2-5}$ alkenyl", "C$_{2-8}$ alkenyl", "C$_{2-14}$ alkenyl" and "C$_{2-16}$ alkenyl" refer to at least one double bond alkenyl group having two to four, two to five, two to eight, two to fourteen, or two to sixteen carbon atoms, respectively such as, for example, ethenyl, propenyl, butenyl, pentenyl, pentdienyl, hexenyl, hexdienyl, heptenyl, heptdienyl, octenyl, octdienyl, octatrienyl, nonenyl, nonedienyl, nonatrienyl, undecenyl, undecdienyl, dodecenyl, tridecenyl, tetradecenyl and their isomeric forms thereof.

The terms "C$_{2-5}$ alkynyl", "C$_{2-8}$ alkynyl", and "C$_{2-10}$ alkynyl" refer to at least one triple bond alkynyl group having two to five, two to eight, or two to ten carbon atoms respectively such as, for example, ethynyl, propynyl, butynyl, pentynyl, pentdiynyl, hexynyl, hexdiynyl, heptynyl, heptdiynyl, octynyl, octdiynyl, octatriynyl, nonynyl, nonediynyl, nonatriynyl and their isomeric forms thereof.

The terms "C$_{3-4}$ cycloalkyl", "C$_{3-6}$ cycloalkyl", "C$_{5-6}$ cycloalkyl", and "C$_{3-8}$ cycloalkyl" refer to a cycloalkyl having three to four, three to six, five to six, or three to eight carbon atoms respectively such as, for example, cyclopropyl, cyclobutyl, cyclopentyl, cyclohexyl, cycloheptyl, cyclooctyl, and their isomeric forms thereof.

The terms "C$_{1-4}$ alkoxy", "C$_{1-6}$ alkoxy", and "C$_{1-8}$ alkoxy" refer to an alkyl group having one to four, one to six, or one to eight carbon atoms respectively attached to an oxygen atom such as, for example, methoxy, ethoxy, propyloxy, butyloxy, pentyloxy, hexyloxy, heptyloxy, or octyloxy and their isomeric forms thereof.

The terms "C$_{1-6}$ alkylamino", and "C$_{1-8}$ alkylamino" refer to an alkyl group having one to six, or one to eight carbon atoms respectively attached to an amino moiety such as, for example, methylamino, ethylamino, propylamino, butylamino, pentylamino, hexylamino, heptylamino, or octoylamino and their isomeric forms thereof.

The terms "C$_{1-6}$ dialkylamino", and "C$_{1-8}$ dialkylamino" refer to two alkyl groups having one to six, or one to eight carbon atoms respectively attached to an amino moiety such as, for example, dimethylamino, methylethylamino, diethylamino, dipropylamino, methypropylamino, ethylpropylamino, dibutylamino, dipentylamino, dihexylamino, methylhecylamino, diheptylamino, or dioctoylamino and their isomeric forms thereof.

The terms "C$_{1-3}$ acyl", "C$_{1-4}$ acyl", "C$_{1-5}$ acyl", "C$_{1-6}$ acyl", "C$_{1-8}$ acyl", and "C$_{2-8}$ acyl" refer to a carbonyl group having an alkyl group of one to three, one to four, one to five, one to six, one to eight, or two to eight carbon atoms.

The terms "C$_{1-4}$ alkoxycarbonyl", "C$_{1-6}$ alkoxycarbonyl", and "C$_{1-8}$ alkoxycarbonyl" refer to an ester group having an alkyl group of one to four, one to six, or one to eight carbon atoms.

The term "C$_{1-8}$ alkyl phenyl" refers to an alkyl group having one to eight carbon atoms and isomeric forms thereof which is substituted with at least one phenyl radical.

The term "C$_{2-8}$ alkenyl phenyl" refers to a at least one double bond alkenyl group having one to eight carbon atoms and isomeric forms thereof which is substituted with at least one phenyl radical.

The term "C$_{1-8}$ alkyl pyridyl" refers to an alkyl group having one to eight carbon atoms and isomeric forms thereof which is substituted with at least one pyridyl radical.

The term "$C_{1-8}$ hydroxyl" refers to an alkyl group having one to eight carbon atoms and isomeric forms thereof attached to a hydroxy group.

The term "$C_{1-8}$ alkylsulfonyl" refers to an alkyl group having one to eight carbon atoms and isomeric forms thereof attached to a $SO_2$ moiety.

The term "$C_{1-6}$ alkylthio" refers to an alkyl group having one to six carbon atoms and isomeric forms thereof attached to a sulfur atom.

The term "Het" refers to 5 to 10 membered saturated, unsaturated or aromatic heterocyclic rings containing one or more oxygen, nitrogen, and sulfur forming such groups as, for example, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, $^3$-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl,1-purinyl, 3-isothiazolyl, 4-isothiazolyl and 5-isothiazolyl, 1,3,4,-oxadiazole, $^4$-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate.

The term halo refers to fluoro, chloro, bromo, or iodo.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

When Q is the structure of

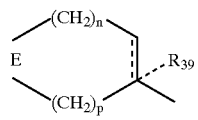

the dotted line in the heterocyclic ring means that this bond can be either single or double. In the case where the dotted line is a double bond, the $R_{39}$ group will not be present.

The compounds of Formula I of this invention contain a chiral center at C5 of the isoxazoline ring, and as such there exist two enantiomers or a racemic mixture of both. This invention relates to both the enantiomers, as well as mixtures containing both the isomers. In addition, depending on substituents, additional chiral centers and other isomeric forms may be present in any of A or $R_1$ group, and this invention embraces all possible stereoisomers and geometric forms in these groups.

The compounds of this invention are useful for treatment of microbial infections in humans and other warm blooded animals, under both parenteral and oral administration.

The pharmaceutical compositions of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound according to this invention.

The quantity of active component, that is the compound according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 four times per day.

When the compounds according to this invention are administered parenterally, i.e., by injection, for example, by intravenous injection or by other parenteral routes of administration. Pharmaceutical compositions for parenteral administration will generally contain a pharmaceutically acceptable amount of the compound or a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compound of this invention generally will be dissolved in the carrier in an amount sufficient to provide a pharmaceutically acceptable injectable concentration in the range of about 1 mg/mL to about 400 mg/mL of solution. The resulting liquid pharmaceutical composition will be administered so as to obtain the above-mentioned antibacterially effective amount of dosage. The compounds according to this invention are advantageously administered orally in solid and liquid dosage forms.

MIC Test Method

The in vitro MICs of test compounds were determined by a standard agar dilution method. A stock drug solution of each analog is prepared in the preferred solvent, usually DMSO:H$_2$O (1:3). Serial 2-fold dilutions of each sample are made using 1.0 ml aliquots of sterile distilled water. To each 1.0 ml aliquot of drug is added 9 ml of molten Mueller Hinton agar medium. The drug-supplemented agar is mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35° C.

Following incubation the Minimum Inhibitory Concentration (MIC µg/ml), the lowest concentration of drug that inhibits visible growth of the organism, is read and recorded. The data is shown in Tables I and II.

TABLE 1

| Structure | Oxazolidinone MIC Values (Gram+) | | | | |
| --- | --- | --- | --- | --- | --- |
| | SAUR 9213 | SEPI 12084 | EFAE 9217 | SPNE 9912 | SPYO 152 |
| Comparison* | 16 | 4 | 8 | .5 | 1 |
| Example 3 | 4 | 1 | 2 | .25 | .5 |
| Comparison* | 2 | 1 | 2 | .5 | 1 |

TABLE 1-continued

| Structure | Oxazolidinone MIC Values (Gram+) | | | | |
|---|---|---|---|---|---|
| | SAUR 9213 | SEPI 12084 | EFAE 9217 | SPNE 9912 | SPYO 152 |
| Example 1 | 1 | .25 | .5 | .13 | .13 |
| Example 5 | 1 | .25 | .5 | <.125 | .25 |
| Example 6 | 2 | 1 | 2 | .5 | 1 |
| Comparison* | .5 | .25 | 1 | .13 | .25 |
| Example 2 | 8 | 2 | 4 | 2 | 4 |

SAUR: *S. aureus*
SEPI: *S. epidermidis*
EFAE: *E. faecalis*
SPNE: *S. pneumoniae*
SPYO: *S. pyogenes*
*not a compound of the subject invention

TABLE II

| Example No. | SAUR 9213 MIC | SEP1 30593 MIC | EFAE 12712 MIC | SPNE 9912 MIC | SPYO 152 MIC | HINF 30063 MIC | MCAT 30610 MIC | EFAE 9217 MIC |
|---|---|---|---|---|---|---|---|---|
| 1 | 1 | 0.25 | 0.5 | <0.125 | <0.125 | 8 | 1 | 0.5 |
| 2 | 8 | 4 | 8 | 2 | 4 | >16 | >16 | 4 |
| 3 | 4 | 1 | 1 | 0.25 | 0.5 | 16 | 4 | 2 |
| 5 | 1 | 0.5 | 0.5 | <0.125 | 0.25 | 4 | 2 | 0.5 |
| 6 | 2 | 2 | 2 | 0.5 | 1 | 16 | 8 | 2 |
| 7 | 0.5 | 0.25 | 0.5 | <0.125 | 0.25 | 4 | 1 | 0.5 |
| 8 | 2 | 1 | 0.5 | <0.125 | 0.25 | 4 | 2 | 1 |
| 9 | 0.5 | 0.25 | 0.25 | <0.125 | <0.125 | 2 | 0.5 | 0.25 |
| 10 | 2 | 1 | 0.5 | <0.125 | 0.25 | 2 | 1 | 1 |
| 11 | 0.25 | 0.25 | 0.25 | <0.125 | 0.25 | 2 | 1 | 0.25 |
| 12 | 1 | 0.5 | 0.25 | <0.125 | <0.125 | 1 | 0.5 | 0.5 |
| 13 | 1 | 1 | 2 | 0.5 | 1 | >16 | 8 | 2 |
| 14 | 1 | 0.5 | 1 | 0.25 | 0.5 | 8 | 1 | 1 |
| 15 | 32 | 16 | 32 | 4 | 8 | >64 | 64 | 32 |
| 16 | 8 | 8 | 16 | 2 | 8 | >64 | 32 | 16 |
| 17 | 2 | 2 | 4 | 1 | 2 | 64 | 16 | 4 |
| 18 | 2 | 1 | 2 | <0.5 | 1 | 32 | 4 | 2 |
| 19 | 32 | 16 | 32 | 16 | 16 | 64 | 32 | 32 |
| 21 | 4 | 4 | 8 | 2 | 4 | 64 | 16 | 8 |
| 22, 23 | 0.5 | 0.5 | 1 | <0.125 | 0.25 | 4 | 2 | 1 |
| 24 | 1 | 0.25 | 0.5 | <0.125 | 0.25 | 4 | 2 | 0.5 |
| 25 | 0.5 | 0.25 | 0.5 | <0.125 | <0.125 | 2 | 2 | 0.5 |
| 26 | 1 | 0.5 | 1 | 0.25 | 0.5 | 16 | 2 | 1 |
| 27 | 0.5 | 0.5 | 0.5 | <0.125 | 0.25 | 4 | 2 | 1 |
| 28 | 0.5 | 0.25 | 0.5 | 0.25 | 0.25 | 2 | 1 | 0.5 |
| 29 | 0.25 | 0.25 | 0.25 | <0.125 | <0.125 | 2 | 0.5 | 0.25 |
| 30 | 4 | 1 | 0.5 | <0.125 | 0.25 | 8 | 2 | 1 |
| 31 | 2 | 1 | 1 | <0.125 | 0.25 | 4 | 1 | 1 |
| 32 | 16 | 2 | 2 | 0.25 | 0.25 | 8 | 2 | 4 |
| 33 | 4 | 2 | 1 | 0.25 | 0.25 | 4 | 2 | 4 |
| 34 | 2 | 1 | 2 | 0.5 | 1 | >16 | 4 | 2 |
| 35 | 1 | 0.5 | 1 | 0.25 | 0.5 | 16 | 2 | 1 |

Key:
SAUR 9213: *S. aureus*
SEP1 30593: *S. epidermidis*
EFAE 12712: *E. Faecium*
SPNE 9912: *S. pneumoniae*
SPYO 152: *S. pyogenes*
HINF 30063: *Haemophilus influenzae*
MCAT 30610: *Moraxella catarrhalis*
EFAE 9217: *Enterococcus faecalis*

As shown in Scheme 1, the intermediates II for the compounds of this invention are also intermediates disclosed in the oxazolidinone patents and published applications hereinabove incorporated by reference. The intermediates IV for this invention are final products (Examples) from the oxazolidinone patents and published applications hereinabove incorporated by reference.

As shown in Scheme 1, Step 1, and illustrated in Example 5, the isothiocyanates III can be conveniently prepared by allowing the amine intermediates (II) to react with 1,1'-thiocarbonyldi-2(1H)-pyridone in solvents such as methylene chloride at 0 to 25° C. The thioureas (Ia, R'=H, alkyl$_{1-4}$) can then be prepared as shown in Step 2 by the reaction of III with ammonia or the appropriate primary amines in solvents such as 1,4-dioxane or tetrahydrofuran at 0–50° C. Alternatively, as illustrated in Example 6 and shown in Step 3, the thioureas can be prepared by allowing II to react with an appropriate isothiocyanate (R'—N=C=S) in solvents such as tetrahydrofuran at 0–50° C. Thioamides (Ib, R"=H, alkyl$_{1-4}$) are prepared by allowing II to react with an appropriate dithioester (R'"S—C(=S)—R", Step 4 as illustrated in Example 4. This reaction is carried out in aqueous-alcoholic solvents at 0–50° C. in the presence of an equivalent of an alkali metal hydroxide. This reaction, especially when R'" is methyl or ethyl, can be catalyzed by an alkali metal fluoride.

The reaction of II with R'"—S—C(S)—R'" (R'"=CH$_3$, C$_2$H$_5$) to give Ib (Step 4) can also be carried out in the presence of a tertiary amine base such as triethylamine in solvents such as THF, dioxane or methylene chloride at 10–50° C. for 3–48 hr.

When the reaction conditions are tolerated by the substituents on R (see, for example, Examples 1–3) the thioamides (Ib, R"—H, alkyl$_{1-4}$) can also be conveniently prepared (Step 5) by allowing the appropriate amide intermediates (IV) to react with reagents such as 2,4-bis(p-methoxyphenyl)-1,3-dithiadiphosphetane-2,4-disulfide (Lawesson's Reagent) in 1,4-dioxane, benzene, toluene or tetrahydrofuran at 60–110° C.; phosphorus decasulfide and sodium carbonate in tetrahydrofuran at 20–50° C. [Brillon, D., Synthetic Communications, 20, 3085 (1990)] or phosphorus decasulfide and sodium fluoride in 1,2-dimethoxyethane at 20–50° C. [Hartke, K., Gerber, H.-D., J. Prakt. Chem., 338, 763 (1996)].

Compounds Ic are prepared (Step 6) by allowing II to react first with carbon disulfide and a tertiary amine base such as triethylamine in solvent mixtures containing water and methanol, ethanol or isopropanol at 10–50° C. for 5–24 hours. The resulting intermediate is treated with an alkylating agent (R'" X where X represents bromo, iodo, alkylsulfonyloxy or arylsulfonyloxy) at 0–30° C. to give compounds Ic. In Step 7, compounds Ic are allowed to react with alkali metal alkoxide such as sodium methoxide or potassium ethoxide in the corresponding alkanol as solvent. This reaction is conveniently carried out at the reflux temperature of the alkanol for 1–24 hr.

SCHEME 1

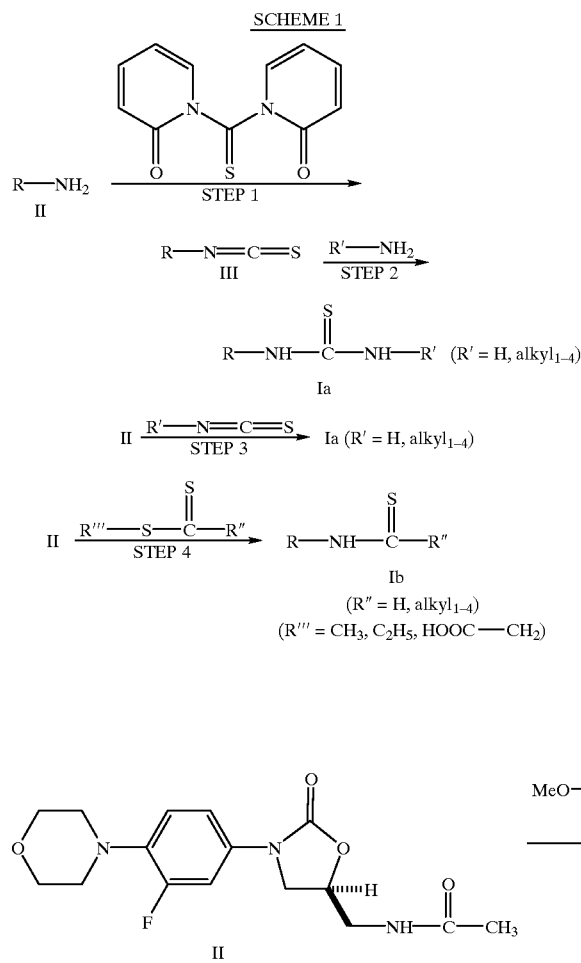

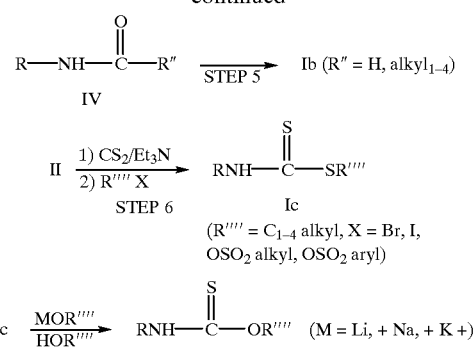

In order to more fully illustrate the nature of the invention and the manner of practicing the same, the following experimental examples are presented.

EXAMPLE 1

(S)-N-[[3-[3-Fluoro-4-(4-morpholinyl)phenyl]-2-oxo-5-oxazolidinyl]methyl]thioacetamide (I)

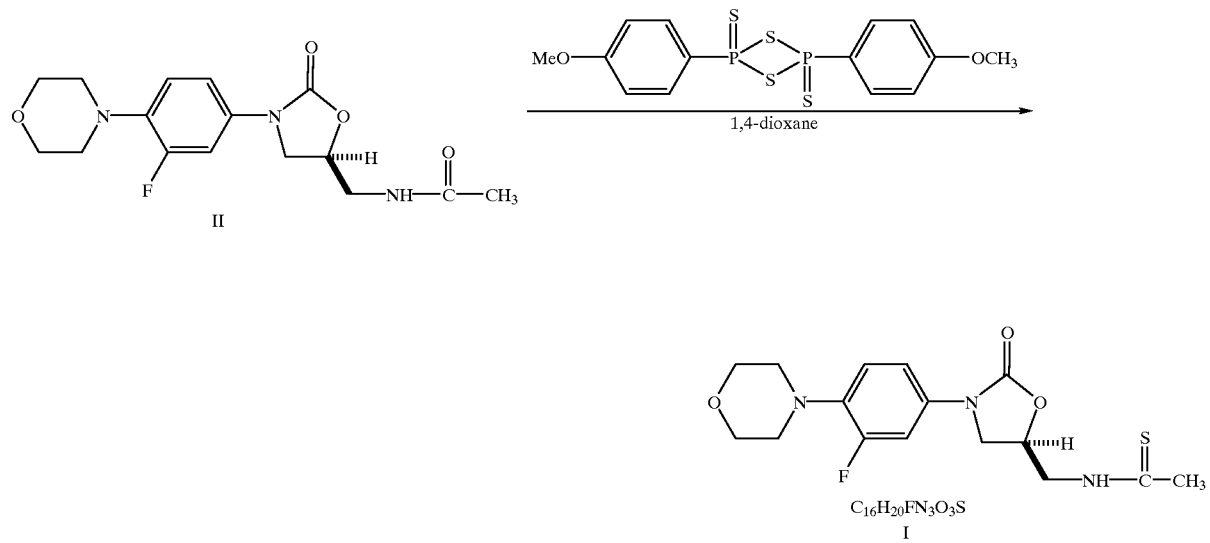

A stirred mixture of II (PCT/US94/08904, 3.37 g, 10.0 mmol) in dry dioxane (100 mL), under nitrogen was treated with Lawesson's Reagent (4.04 g, 10.0 mml), warmed to reflux during 1 h and refluxed for 1.5 h. The reaction was complete by TLC on silica gel with 10% MeOH—CHCl$_3$. It was kept at ambient temperature for 18 h and concentrated in vacuo. Chromatography of the residue on silica gel with mixtures of acetone-methylene chloride containing 10–15% acetone gave the product which was crystallized from acetone-hexane to give 1: mp 157.5–158.5° C.; HRMS theory for C$_{16}$H$_{20}$FN$_3$O$_3$S (M$^+$): 353.1209; found: 353.1212. Anal. calcd for C$_{16}$H$_{20}$FN$_3$O$_3$S: C, 54.38; H, 5.38; N, 11.89; S, 9.07. Found: C, 54.21; H, 5.58; N, 11.78; S, 8.93.

EXAMPLE 2

(S)-N-[[3-[3-Fluoro-4-[4-(5-methyl-1,3,4-thiadiazol-2-yl)-1-piperazinyl]phenyl]-2-oxo-5-oxazolidinyl]methyl]thioacetamide (2)

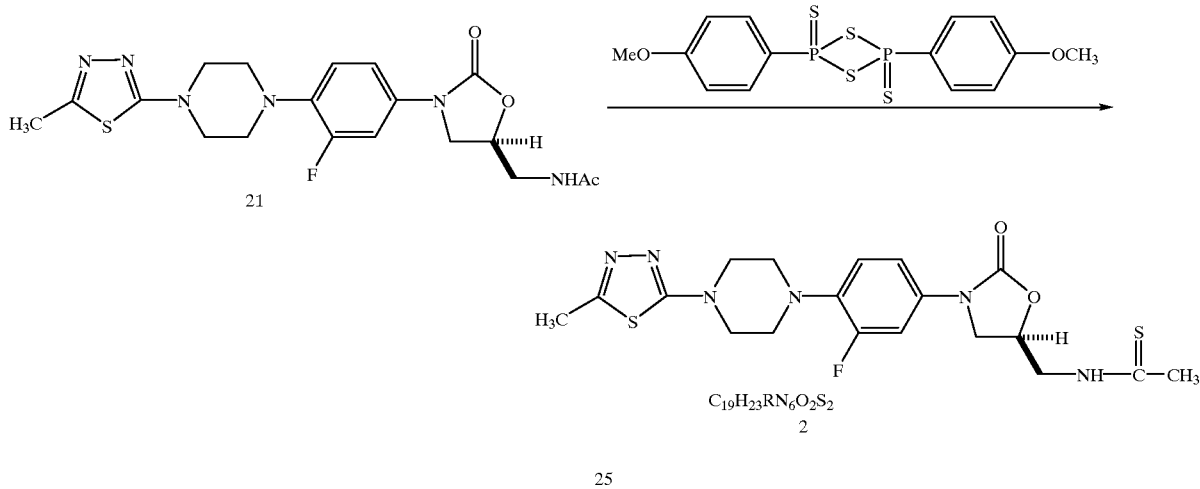

According to Example 1, for the preparation of 1, 21 (PCT/US97/01970) was allowed to react with Lawesson's Reagent in refluxing dioxane to give 2: mp 222–223° C.; HRMS theory for $C_{19}H_{24}FN_6O_2S_2$ (M+H$^+$): 451.1386; found 451.1381.

EXAMPLE 3

(S)-N-[[3-[3-Fluoro-4-[2',5'-dioxospiro[piperidine-4,4'-imidazolidine]-1-yl]phenyl]-2-oxo-5-oxazolidinyl]methyl]thioacetamide (3)

STEP A: (S)-N-[[3-[3-Fluoro-4-[2',5'-dioxospiro[piperidine-4,4'-imidazolidine]-1-yl]phenyl]-2-oxo-5-oxazolidinyl]methyl]acetamide (32)

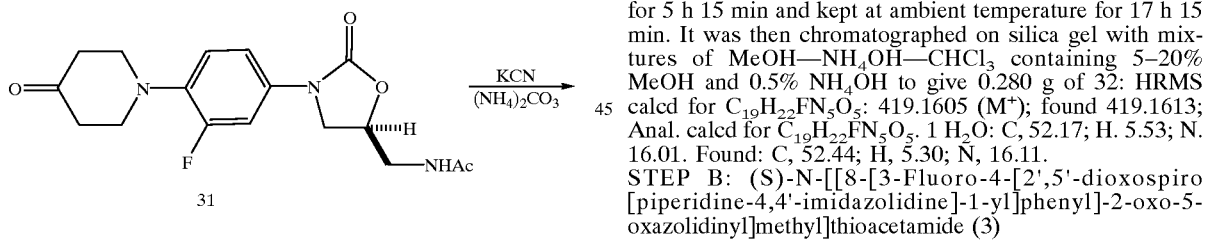

A stirred suspension of 31 (Case 4780.P CP, 0.349 g, 1.00 mmol) in 1:1 EtOH:H$_2$O (5 mL), under nitrogen, was treated with potassium cyanide (0.130 g, 2.00 mmol) and ammonium carbonate (0.701 g, 7.30 mmol), warmed at 55–60° C. for 5 h 15 min and kept at ambient temperature for 17 h 15 min. It was then chromatographed on silica gel with mixtures of MeOH—NH$_4$OH—CHCl$_3$ containing 5–20% MeOH and 0.5% NH$_4$OH to give 0.280 g of 32: HRMS calcd for $C_{19}H_{22}FN_5O_5$: 419.1605 (M$^+$); found 419.1613; Anal. calcd for $C_{19}H_{22}FN_5O_5$. 1 H$_2$O: C, 52.17; H. 5.53; N. 16.01. Found: C, 52.44; H, 5.30; N, 16.11.

STEP B: (S)-N-[[8-[3-Fluoro-4-[2',5'-dioxospiro[piperidine-4,4'-imidazolidine]-1-yl]phenyl]-2-oxo-5-oxazolidinyl]methyl]thioacetamide (3)

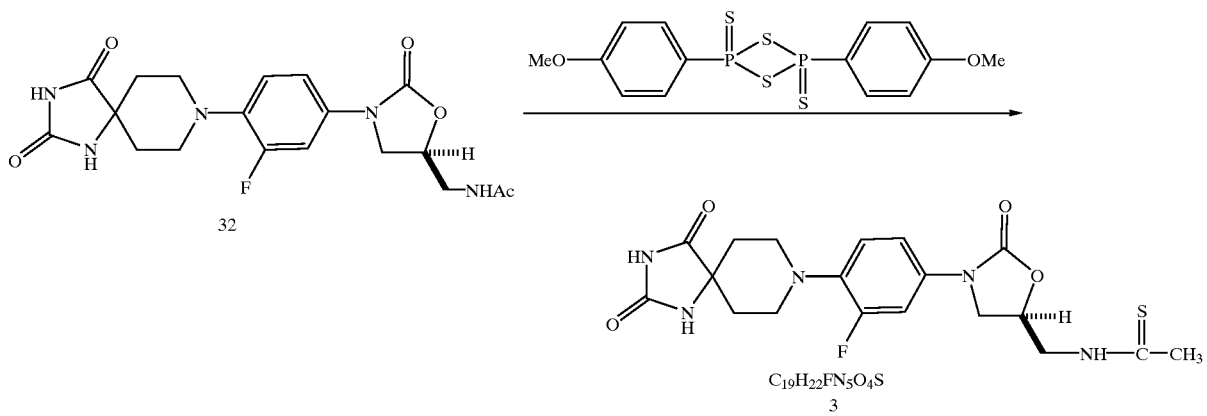

A stirred suspension of 32 (0.210 g, 0.500 mmol) in dioxane (5.0 mL), under nitrogen was treated with Lawesson's Reagent (0.202 g, 0.500 mmol), refluxed for 4 h and concentrated in vacuo. The residue was chromatographed on silica gel with mixtures of MeOH—NH$_4$OH—CHCl$_3$ containing 1–10% MeOH and 0.1–0.5% NH$_4$OH and the resulting product was crystallized from MeOH—CHCl$_3$—EtOAc to give 0.0491 g of 3: mp 218.5° C.; HR FAB MS theory for C$_{19}$H$_{22}$FN$_5$O$_4$S (M$^+$): 435.1376; found 435.1370. Anal. calcd for C$_{19}$H$_{22}$FN$_5$O$_4$S.0.5 H$_2$O: C, 51.34; H, 5.21; N, 15.76. Found: C, 51.69; H, 5.00; N, 15.25.

EXAMPLE 4

(S)-N -[[3-[3-Fluoro-4-(4-morpholinyl)phenyl]-2-oxo-5-oxazolidinyl]methyl]thioacetamide (4)

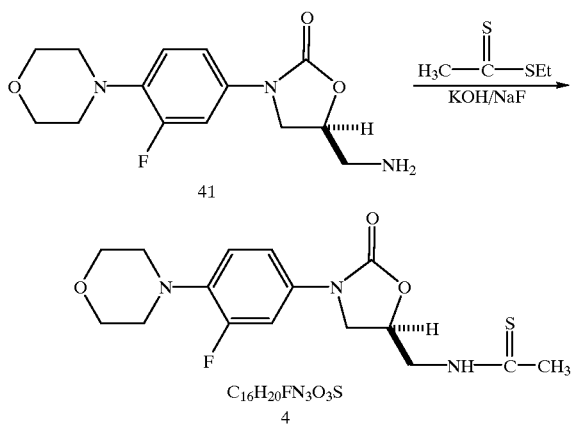

A solution of 41 (148 mg, 0.500 mmuol) and 0.97M KOH (0.515 mL) in absolute EtOH (5 mL) was added to a solution of ethyl dithioacetate (57 μL, 0.50 mmol) and sodium fluoride (20 mg, 0.47 mmol) in absolute EtOH (5 mL) and the mixture was kept at ambient temperature for 3 h 40 min. Additional ethyl dithioacetate (5 μL) was added after 1 h 55 min and additional 0.97M KOH (40 mL) and sodium fluoride (6 mg) were added to the mixture after 3h 5 min. The reaction was followed by TLC on silica gel with 10% MeOH—CHCl$_3$ and 30% acetone-CH$_2$Cl$_2$. The major product had an R$_f$ on TLC that was the same as that of 4.

EXAMPLE 5

(S)-N-[[3-[3-Fluoro-4-(4-morpholinyl)phenyl]-2-oxo-5-oxazolidinyl]methyl]thiourea (5)

STEP A:

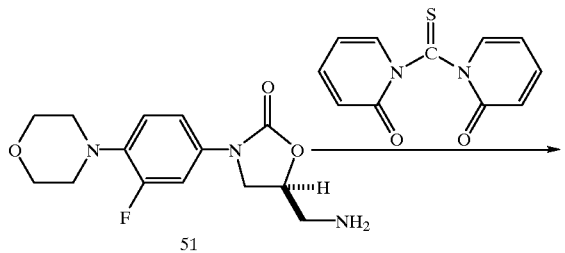

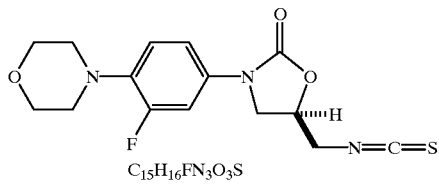

A solution of 51 (PCT/US94/08904, 2.07 g, 7.00 mmol) in CH$_2$Cl$_2$ was added, dropwise during 30 min. under nitrogen to an ice cold, stirred solution of 1,1'-thiocarbonyldi-2(1H)-pyridone (1.95 g, 8.40 mmol) in CH$_2$Cl$_2$ (70 mL). The mixture was warmed slowly to ambient temperature and kept for 18 h. It was then diluted with CH$_2$Cl$_2$, washed with water and aqueous NaCl, dried (Na$_2$SO$_4$) and concentrated. Chromatography of the residue on silica gel with 10% acetonitrile-CH$_2$Cl$_2$ gave 1.60 g of the isothiocyanate: HRMS theory for C$_{15}$H$_{16}$FN$_3$O$_3$S (M$^+$): 337.0896; found 337.0888.

STEP B:

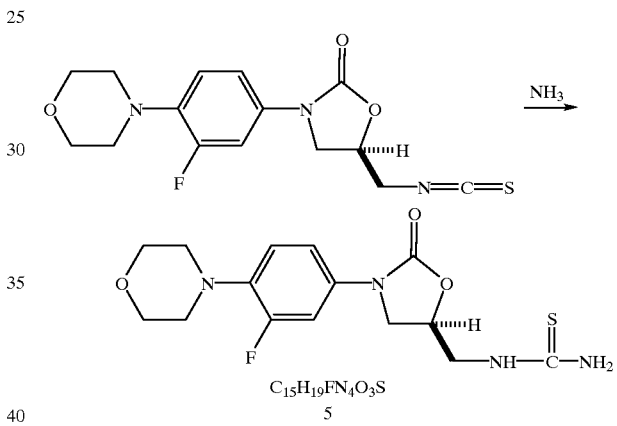

Anhydrous ammonia was bubbled for 7 min through a stirred solution of the product from Step I (1.00 g, 2.96 mmol) in THF (10 mL) and the mixture was kept at ambient temperature for 3 h 25 min and concentrated in vacuo. Crystallization of the residue from acetone-hexane gave 0.861 g of 5: mp 199–199.5° C.; MS m/z 354 (M$^+$). Anal. calcd for C$_{15}$H$_{19}$FN$_4$O$_3$S: C, 50.84; H, 5.40; N, 15.81. Found: C, 50.87; H, 5.39; N, 15.72.

EXAMPLE 6

(S)-N-[[3-[3-Fluoro-4-(4-morpholinyl)phenyl]-2-oxo-5-oxazolidinyl]methyl]-N'-methylthiourea (6)

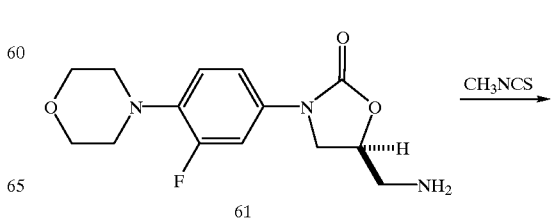

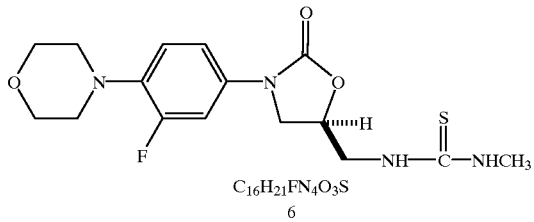

C16H21FN4O3S
6

A stirred solution of methyl isothiocyanate (93 mg, 1.27 mmol) in THF, was treated with 61 (295 mg, 1.00 mmol), kept at ambient temperature for 18 h and concentrated in vacuo. The residue was recrystallized from EtOAc-hexane to give 246 mg of 6: mp 158–160° C.; MS m/z 368 (M+). Anal. calcd for $C_{16}H_{21}FN_4O_3S$: C, 52.16; H, 5.74; N, 15.21. Found: C, 52.20; H, 5.85; N, 15.17.

EXAMPLE 7

(S)-cis-N-[[3-[3-Fluoro-4-(tetrahydro-1-oxido-2H-thiopyran-4-yl)phenyl]-2-oxo-5-oxazolidinyl]methyl]ethanethioamide

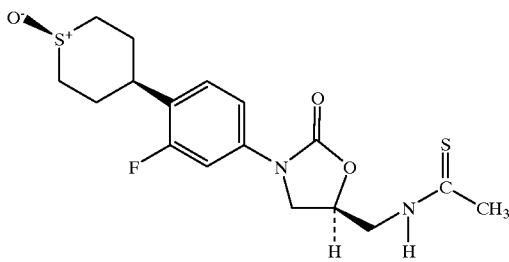

Step 1: A mixture of (S)-(−)-N-[[3-[3-fluoro-4-(3,6-dihydro-2H-thiopyran-4-yl)phenyl]-2-oxo-5-oxazolidinyl]methyl]acetamide S-oxide (4.50 g, can be obtained according to the procedures disclosed in International Publication No. WO 97/09328) and platinum oxide (697 mg) in methanol (164 mL) is shaken on the Parr apparatus under a hydrogen atmosphere at 40 psi for 18 hours. The catalyst is then removed by filtration through Celite, and the filtrate is concentrated under reduced pressure and the residue chromatographed on silica gel (230–400 mesh, 350 g), eluting with a gradient of methanol/methylene chloride (3/97–7/93). Pooling and concentration of those fractions with an $R_f$=0.44 by TLC (methanol/chloroform, 10/90) gives (S)-cis-(−)-N-[[3-[3-Fluoro-4-(tetrahydro-1-oxido-2H-thiopyran-4-yl)phenyl]-2-oxo-5-oxazolidinyl]methyl]acetamide, mp 203–204° C.

Step 2: A mixture of the compound prepared in Step 1 (2.50 g) and hydroxylamine hydrochloride (2.36 g) in pyridine (30.6 mL) and ethanol (3.4 mL) is stirred in a screw-cap vial at 100° C. for 22 hrs and at ambient temperature for 16 hrs, during which additional hydroxylamine hydrochloride (944 mg) and pyridine (4 mL) is added. The reaction mixture is then concentrated under reduced pressure, diluted with saturated aqueous sodium bicarbonate (100 mL) and saline (50 mL), adjusted to pH 11 with solid sodium carbonate and extracted with methanol/methylene chloride (10/90, 5×100 mL). The combined organic phase is concentrated under reduced pressure, and the crude product is chromatographed on silica gel (230–400 mesh, 150 g), eluting with a gradient of methanol/methylene chloride (6/94–10/90). Pooling and concentration of those fractions with an $R_f$=0.14 by TLC (methanolchloroform, 10/90) gives (S)-cis-3-[3-fluoro-4-(tetrahydro-1-oxido-2H-thiopyran-4-yl)phenyl]-5-aminomethyl-2-oxazolidinone, mp 159–161° C.

Step 3: A solution of ethyl dithioacetate (105 mL, 0.919 mmol) and sodium fluoride (39 mg, 0.919 mmol) in ethanol (9.2 mL) under a nitrogen atmosphere was treated with a mixture of (S)-cis-3-[3-fluoro-4-(tetrahydro-1-oxido-2H-thiopyran-4-yl)phenyl]- 5-aminomethyl-2-oxazolidinone, as prepared in Step 2, (300 mg, 0.919 mmol) and aqueous potassium hydroxide (1M, 0.92 mL) in ethanol (46 mL). The resulting solution was stirred at ambient temperature for 4 hours and was then diluted with methylene chloride (150 mL) and washed with water (50 mL), aqueous potassium hydrogen sulfate (1M, 50 mL) and brine (25 mL). The organic phase was dried over anhydrous sodium sulfate and concentrated in vacuo, and the crude product was triturated with methylene chloride/diethyl ether and filtered to give the title compound, mp 176–177° C. (dec.).

EXAMPLE 8

(S)-cis-[[3-[3-Fluoro-4-(tetrahydro-1-oxido-2H-thiopyran-4-yl)phenyl]-2-oxo-5-oxazolidinyl]methyl]thiourea

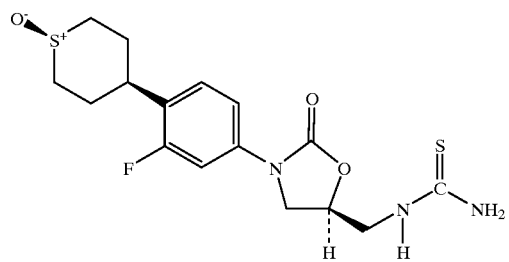

Step 1: A solution of 1,1'-thiocarbonyldi-2(1H)-pyridone (235 mg, 1.01 mmol) in anhydrous methylene chloride (10 mL) at 0° C. under a nitrogen atmosphere was treated with a solution of (S)-cis-3-[3-fluoro-4-(tetrahydro-1-oxido-2H-thiopyran-4-yl)phenyl]-5-aminomethyl-2-oxazolidinone, as prepared in Example 7, Step 2, (275 mg, 0.843 mmol) in anhydrous methylene chloride (34 mL) over 30 minutes. The resulting mixture was stirred at 0° C. for 30 minutes and at ambient temperature for 1 hour and was then diluted with methylene chloride (40 mL), washed with water (25 mL) and brine (25 mL), dried over anhydrous sodium sulfate and concentrated in vacuo. The crude product was chromatographed on silica gel (70–230 mesh, 20 g), eluting with acetonitrile/methylene chloride (40/60), and those fractions with an $R_f$=0.07 by TLC (acetonitrile/methylene chloride, 30/70) were pooled and concentrated to give (S)-cis-3-[3-Fluoro-4-(tetrahydro-1-oxido-2H-thiopyran-4-yl)phenyl]-5-isothiocyanatomethyl-2-oxazolidinone, mp 187–190° C. (dec.).

Step 2: A solution of (S)-cis-3-[3-fluoro-4-(tetrahydro-1-oxido-2H-thiopyran-4-yl)phenyl]-5-isothiocyanatomethyl-2-oxazolidinone (Step 1, 290 mg, 0.787 mmol) in anhydrous tetrahydrofuran (39 mL) at 0° C. under a nitrogen atmosphere was treated (bubbled) with a stream of ammonia gas for 5 minutes. The reaction pot was sealed, and the resulting mixture was stirred at 0° C. for 1 hour. The excess ammonia was then removed under a stream of nitrogen, and the reaction mixture was concentrated in vacuo to give the crude product. Recrystallization from methanoilmethylene chloride/diethyl ether gave the title compound, mp 206–208° C. (dec.).

EXAMPLE 9

(S)-trans-N-[3-[3-Fluoro-4-(tetrahydro-1-oxido-2H-thiopyran-4-yl)phenyl]-2-oxo-5-oxazolidinyl]methyl]ethanethioamide

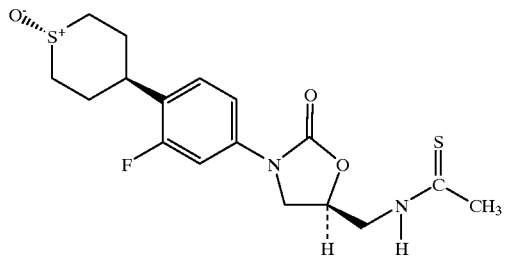

Step 1: (S)-(−)-N-[[3-[3-fluoro-4-(3,6-dihydro-2H-thiopyran-4-yl)phenyl]-2-oxo-5-oxazolidinyl]methyl] acetamide S-oxide (disclosed in International Publication No. WO 97/09328) may be reduced to the corresponding cis- and trans-sulfoxides by catalytic hydrogenation in the presence of a catalyst and solvent. Alternatively, the sulfide by product of this reduction reaction can be oxidized with an oxidizing agent such $NaIO_4$ or meta-chloroperoxybenzoic acid in solvent to provide the cis- and trans-sulfoxides. The isomeric mixture can then be separated by chromatography to isolate the trans-sulfoxide, mp 211–212° C. (dec.). A mixture of the trans-sulfoxide, (S)-trans-(−)-N-[[3-[3-fluoro-4-(tetrahydro-1-oxido-2H-thiopyran-4-yl)phenyl]-2-oxo-5-oxazolidinyl]methyl]acetamide, (0.90 g) and hydroxylamine hydrochloride (0.85 g) in pyridine (11.0 mL) and ethanol (1.2 mL) is stirred in a screw-cap vial at 100° C. for 23 hrs and at ambient temperature for 19 hrs, during which additional hydroxylamine hydrochloride (340 mg) and pyridine (1 mL) is added. The reaction mixture is then concentrated under reduced pressure, diluted with saturated aqueous sodium carbonate (50 mL) and saline (50 mL) and extracted with methanol/methylene chloride (10/90, 6×100 mL). The combined organic phase is concentrated under reduced pressure, and the crude product is chromatographed on silica gel (230–400 mesh, 45 g), eluting with a gradient of methanolmethylene chloride (7.5/92.5–10/90). Pooling and concentration of those fractions with an $R_f$= 0.14 by TLC (methanol/chloroform, 10/90) gives (S)-trans-3-[3-fluoro-4-(tetrahydro-1-oxido-2H-thiopyran-4-yl)phenyl]-5-aminomethyl-2-oxazolidinone, mp 138–140° C.

Step 2: A solution of ethyl dithioacetate (105 mL, 0.919 mmol) and sodium fluoride (39 mg, 0.919 mmol) in ethanol (9.2 mL) under a nitrogen atmosphere was treated with a mixture of (S)-trans-3-[3-fluoro-4-(tetrahydro-1-oxido-2H-thiopyran-4-yl)phenyl]-5-aminomethyl-2-oxazolidinone, as prepare in Step 1, (300 mg, 0.919 mmol) and aqueous potassium hydroxide (1M, 0.92 mL) in ethanol (46 mL). The resulting solution was stirred at ambient temperature for 17 hours and was then diluted with methylene chloride (150 mL), washed with water (2×50 mL) and brine (25 mL), dried over anhydrous sodium sulfate and concentrated in vacuo. The crude product was chromatographed on silica gel (230–400 mesh, 35 g), eluting with methanol/methylene chloride (3/97), and those fractions with an $R_f$=0.56 by TLC (methanol/chloroform, 10/90) were pooled and concentrated and the residue recrystallized from methylene chloride/diethyl ether to give the title compound, mp 193–194° C. (dec.).

EXAMPLE 10

(S)-trans-[[3-[3-Fluoro-4-(tetrahydro-1-oxido-2H-thiopyran-4-yl)phenyl]-2-oxo-5-oxazolidinyl]methyl]thiourea

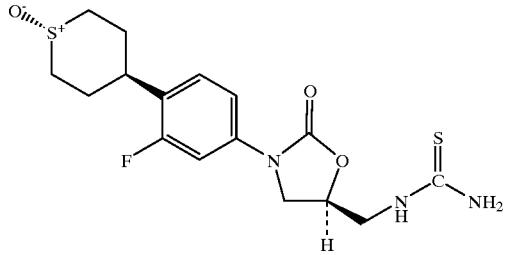

Step 1: A solution of 1,1'-thiocarbonyldi-2(1H)-pyridone (192 mg, 0.827 mmol) in anhydrous methylene chloride (8.3 mL) at 0° C. under a nitrogen atmosphere was treated with a solution of (S)-trans-3-[3-fluoro-4-(tetrahydro-1-oxido-2H-thiopyran-4-yl)phenyl]-5-aminomethyl-2-oxazolidinone, as prepared in Example 9, Step 1, (225 mg, 0.689 mmol) in anhydrous methylene chloride (28 mL) over 30 minutes. The resulting mixture was stirred at 0° C. for 30 minutes and at ambient temperature for 40 minutes and was then diluted with methylene chloride (20 mL), washed with water (15 mL) and brine (15 mL), dried over anhydrous sodium sulfate and concentrated in vacuo. The crude product was chromatographed on silica gel (32–63 mm, 40 g), eluting with a gradient of acetonitrile/methylene chloride (30/70–60/40) under 15 psi $N_2$, and those fractions with an $R_f$ 32 0.12 by TLC (acetonitrile/methylene chloride, 30/70) were pooled and concentrated to give (S)-trans-3-[3-Fluoro-4-(tetrahydro-1-oxido-2H-thiopyran-4-yl)phenyl]-5-isothiocyanatomethyl-2-oxazolidinone, mp 165–167° C.

Step 2: A solution of (S)-trans-3-[3-fluoro-4-(tetrahydro-1-oxido-2H-thiopyran-4-yl)phenyl]-5-isothiocyanatomethyl-2-oxazolidinone (Step 1, 230 mg, 0.624 mmol) in anhydrous tetrahydrofuran (31.2 mL) at 0° C. under a nitrogen atmosphere was treated (bubbled) with a stream of ammonia gas for 5 minutes. The reaction pot was sealed, and the resulting mixture was stirred at 0° C. for 1 hour. The excess ammonia was then removed under a stream of nitrogen, and the reaction mixture was concentrated in vacuo to give the crude product. Trituration with methanol/methylene chloride/diethyl ether gave the title compound, mp 209–210° C. (dec.).

EXAMPLE 11

(S)-N-[[3-[3-Fluoro-4-(tetrahydro-1,1-dioxido-2H-thiopyran-4-yl)phenyl]-2-oxo-5-oxazolidinyl]methyl]ethanethioamide

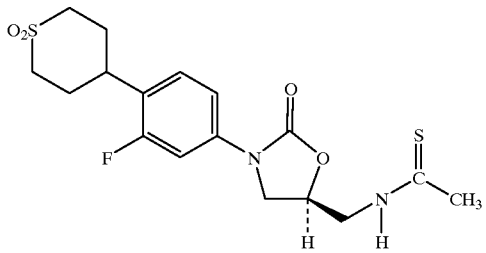

Step 1: Starting with (S)-cis-(−)-N-[[3-[3-Fluoro-4-(tetrahydro-1-oxido-2H-thiopyran-4-yl)phenyl]-2-oxo-5- oxazolidinyl]methyl]acetamide as prepared in Example 7, Step 1, and following the general procedure of Step 2, and making non-critical variations by substituting (S)-(−)-N-[[3-[3-fluoro-4-(tetrahydro-2H-thiopyran-4-yl)phenyl]-2-oxo-5-oxazolidinyl]methyl]acetamide S,S-dioxide (disclosed in International Publication No. WO 97/09328) for (S)-cis-(−)-N-[[3-[3-fluoro-4-(tetrahydro-1-oxido-2H-thiopyran-4-yl)phenyl]-2-oxo-5-oxazolidinyl]methyl]acetamide, the product (S)-(−)-3-[3-Fluoro-4-(tetrahydro-1,1-dioxido-2H-thiopyran-4-yl)phenyl]-5-aminomethyl-2-oxazolidinone is obtained, mp 194° C. (dec.).

Step 2: A solution of ethyl dithioacetate (100 mL, 0.876 mmol) and sodium fluoride (37 mg, 0.876 mmol) in ethanol (8.8 mL) under a nitrogen atmosphere was treated with a mixture of (S)-(−)-3-[3-fluoro-4-(tetrahydro-1,1-dioxido-2H-thiopyran-4-yl)phenyl]-5-aminomethyl-2-oxazolidinone, as prepared in Step 1, (300 mg, 0.876 mmol) and aqueous potassium hydroxide (1M, 0.88 mL) in ethanol (43.8 mL). The resulting mixture was stirred at ambient temperature for 26 hours, during which additional ethyl dithioacetate (50 mL, 0.438 mmol), sodium fluoride (19 mg, 0.438 mmol), aqueous potassium hydroxide (1M, 0.44 mL) and ethanol (3.0 mL) was added, and was then diluted with methylene chloride (150 mL), washed with water (50 mL), aqueous potassium hydrogen sulfate (1M, 50 mL) and brine (25 mL), dried over anhydrous sodium sulfate and concentrated in vacuo. The crude product was recrystallized from methylene chloride/diethyl ether to give the title compound, mp 186–187° C. (dec.).

EXAMPLE 12

(S)-N-[[3-[3-Fluoro-4-(tetrahydro-1,1-dioxido-2H-thiopyran-4-yl)phenyl]-2-oxo-5-oxazolidinyl]methyl]thiourea

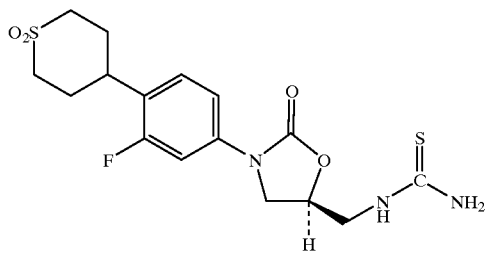

Step 1: A solution of 1,1'-thiocarbonyldi-2(1H)-pyridone (304 mg, 1.31 mmol) in anhydrous methylene chloride (13 mL) at 0° C. under a nitrogen atmosphere was treated with a solution of (S)-(−)-3-[3-fluoro-4-(tetrahydro-1,1-dioxido-2H-thiopyran-4-yl)phenyl]-5-aminomethyl-2-oxazolidinone, as prepared in Example 11, Step 1, (375 mg, 1.09 mmol) in anhydrous methylene chloride (88 mL) over 30 minutes. The resulting mixture was stirred at 0° C. for 30 minutes and at ambient temperature for 30 minutes and was then diluted with methylene chloride (40 mL), washed with water (25 mL) and brine (25 mL), dried over anhydrous sodium sulfate and concentrated in vacuo. The crude product was chromatographed on silica gel (230–400 mesh, 45 g), eluting with acetonitrile/methylene chloride (7.5/92.5), and those fractions with an $R_f$=0.64 by TLC (acetonitrile/methylene chloride, 20/80) were pooled and concentrated to give (S)-3-[3-fluoro-4-(tetrahydro-1,1-dioxido-2H-thiopyran-4-yl)phenyl]-5-isothiocyanatomethyl-2-oxazolidinone, mp 158–162° C. (dec.).

Step 2: A solution of (S)-3-[3-fluoro-4-(tetrahydro-1,1-dioxido-2H-thiopyran-4-yl)phenyl]-5-isothiocyanatomethyl-2-oxazolidinone (Step 1, 380 mg, 0.988 mmol) in anhydrous tetrahydrofuran (49 mL) at 0° C. under a nitrogen atmosphere was treated (bubbled) with a stream of ammonia gas for 5 minutes. The reaction pot was sealed, and the resulting mixture was stirred at 0° C. for 1 hour. The excess, ammonia was then removed under a stream of nitrogen, and the reaction mixture was concentrated in vacuo to give the crude product. Recrystallization from methanol/methylene chloride/diethyl ether gave the title compound, mp 196–198° C. (dec.).

EXAMPLE 13

(S)-N-[[3-[3-Fluoro-4-(4-morpholinyl)phenyl]-2-oxo-5-oxazolidinyl]methyl]-thioformamide (7)

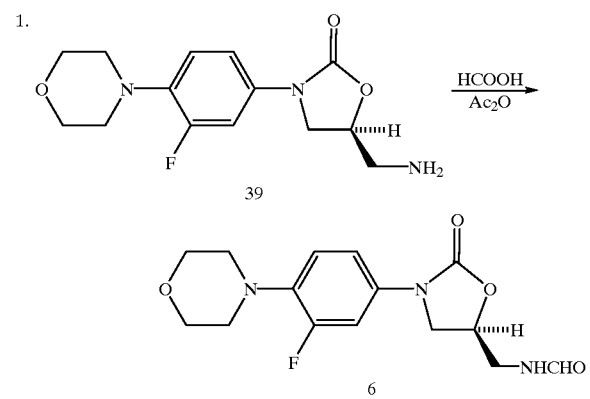

A stirred mixture of acetic anhydride (0.23 mL, 0.0024 mol) and 95–97% formic acid (0.10 mL, 0.0027 mL) was warmed, under nitrogen at 50–55° C. for 2 h, cooled to ambient temperature and treated, portionwise during 2 min, with $39^8$ (0.45 g, 0.0015 mol). The suspension was kept at ambient temperature for 4 h and the resulting solution was treated with Et$_2$O (1 mL) and kept at ambient temperature for 18 h. The mixture was diluted with additional Et$_2$O (10 mL) and the solid was collected by filtration, washed with Et$_2$O and dried to give 0.38 g of $6^9$: MS (ES) m/z 324 (M+H$^+$), 346 (M+Na$^+$); $^1$H NMR (300 mHz, CDCl$_3$) d 3.08 (m, 4H), 3.72 (m, 2H), 3.77 (d,d, 1H), 3.89 (m, 4H), 4.04 (t, 1H), 4.80 (m, 1H), 6.33 (s, 1H), 7.05 (m, 2H), 7.45 (d,d, 1H), 8.27 (s, 1H).

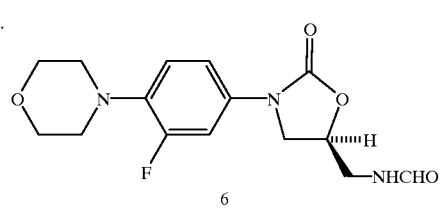

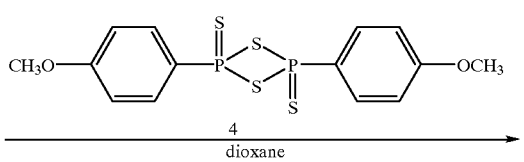

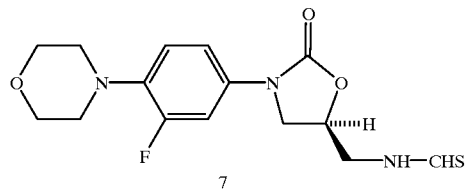

A stirred mixture of 6 (0.38 g, 0.00118 mol) in dioxane (20 mL), under nitrogen was treated with 4 (0.51 g, 0.00126 mol), warmed to reflux during 30 min and kept at this temperature for 90 min. It was then evaporated under a stream of nitrogen. The residue was chromatographed on silica gel with 1.25% MeOH—$CH_2Cl_2$ and the slightly impure product was rechromatographed on silica gel with 25% EtOAc—$CH_2Cl_2$. The resulting product was crystallized from EtOAc-methyl tert-butyl ether to give 0.114 g of 7: mp 150–155° C. (dec); IR (DRIFT) 3322, 1752 $cm^{-1}$; MS(ES) m/z 340 (M+H$^+$), 362 (M+Na$^+$); $^1$HNMR [300 MHz, $(CD_3)_2SO$] d 2.94 (m, 4H), 3.72 (m, 4H), 3.77 (d,d, 1H), 3.94 (t, 2H), 4.12 (t, 1H), 4.93 (m, 1H), 7.05 (t, 1H), 7.16 (d,d, 1H), 7.47 (d,d, 1H), 9.33 (d, 1H), 10.59 (s, 1H). Anal. calcd for $C_{15}H_{18}FN_3O_3S$: C, 53.08; H, 5.35; N, 12.38. Found: C, 53.02; H, 5.44; N, 12.36.

An ice cold, stirred solution of 39[8] (0.395 g, 0.00134 mol) and triethyl amine (0.186 mL, 0.0027 mol) in $CH_2Cl_2$ (20 mL), under nitrogen was treated, dropwise during 2 min. with a solution of propionyl chloride (0.128 mL, 0.00147 mol) in $CH_2Cl_2$ (3 mL) The mixture was kept in the ice bath for 20 min and at ambient temperature for 1 h. It was then diluted with $CH_2Cl_2$, washed with saturated $NaHCO_3$, water and brine, dried ($MgSO_4$) and concentrated. The residue (8)[9] was used without further purification in the next reaction.

1.

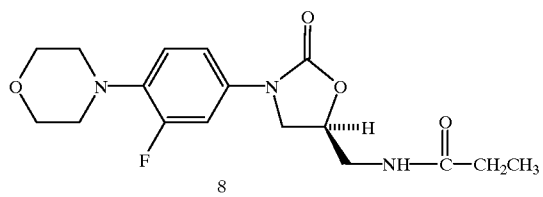

2.

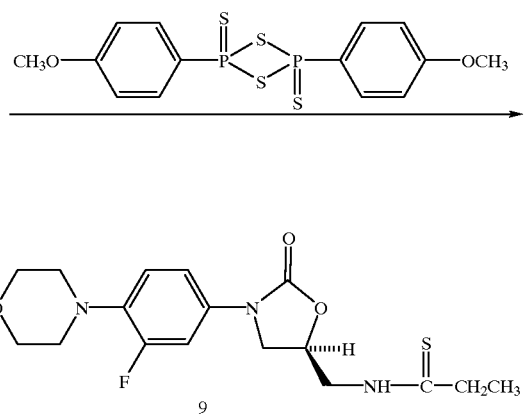

EXAMPLE 14

(S)-N-[[3-[3-Fluoro-4-(4-morpholinyl)phenyl]-2-oxo-5-oxazolidinyl]methyl]thiopropion-amide (9)

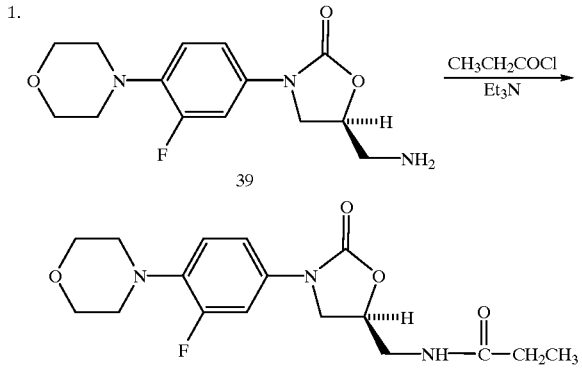

A stirred mixture of the product (8) from the previous reaction and dioxane (20 mL), under nitrogen, was treated, portionwise during 1 min. with Lawesson's reagent (0.58 g, 0.0014 mol) and refluxed for 2 h; it was then concentrated. The residue was chromatographed on silica gel with 2% MeOH—$CHCl_3$ and the product was crystallized from methyl tert-butyl ether to give 0.259 g of 9: mp 138–139° C.; MS(ES) m/z 368 (M+H$^+$), 390 (M+Na$^+$); IR (DRIFT) 3284, 3266, 1748, 1744 $cm^{-1}$; $[\alpha]^{24}_D$ +20° (MeOH); 1H NMR [300 MHz, $(CD_3)_2SO$] d 1.12 (t, 3H), 2.56 (q, 2H), 2.94 (m, 4H), 3.72 (m, 4H), 3.78 (d,d, 1H), 3.90 (t, 2H), 4.11 (t, 1H), 4.93 (m, 1H), 7.05 (t, 1H), 7.16 (d,d, 1H), 7.47 (d,d, 1H), 10.30 (broad s, 1H). Anal. calcd for $C_{17}H_{22}FN_3O_3S$: C, 55.57; H, 6.03; N, 11.44. Found: C, 55.68; H, 6.21; N, 11.37.

EXAMPLE 15

(S)-N-[[3-[3-Fluoro-4-(4-morpholinyl)phenyl]-2-oxo-5-oxazolidinyl]methyl]-2-chlorothioacetamide (11)

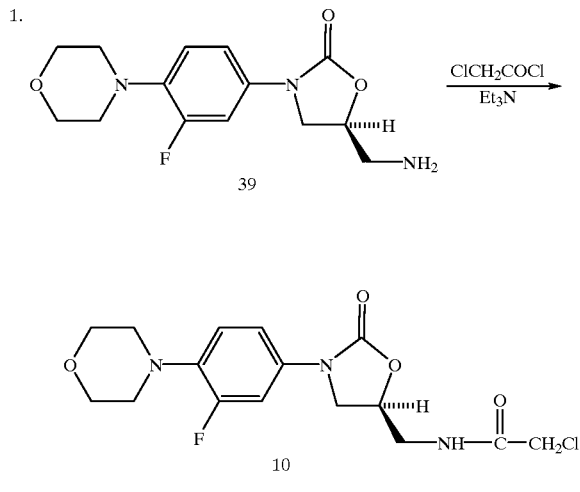

A stirred solution of 39 (1.54 g, 5.2 mmol) and triethylamine (750 mg, 7.5 mmol) in H$_2$Cl$_2$ (50 mL), under nitrogen, was treated, dropwise, during 15 min with a solution of chloroacetyl chloride (465 mL, 5.8 mmol) in CH$_2$Cl$_2$ (30 mL) and kept at ambient temperature for 18 h. It was then washed with saturated NaHCO$_3$ and dilute NaCl, dried (Na$_2$SO$_4$) and concentrated. The residue was flash chromatographed on silica gel with 20–30% acetone-CH$_2$Cl$_2$ to give 1.49 g of 10$^9$ which was used in the next reaction without further purification.

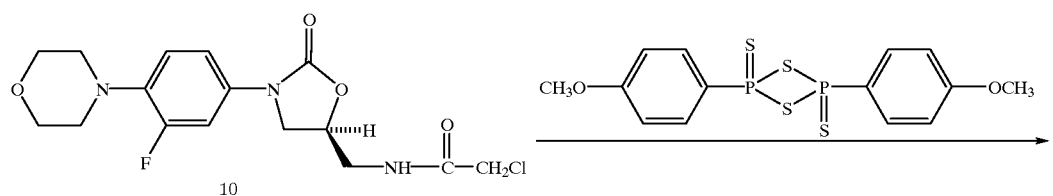

A stirred mixture of 10 (0.371 g, 1.0 mmol) and Lawesson's reagent (0.420 mg, 1.04 mmol) in dioxane (10 mL) was refluxed, under nitrogen for 2 h and concentrated under reduced pressure. The residue was chromatographed on silica gel with 3–10% acetone-CH$_2$Cl$_2$ to give 0.143 g of 11: MS (CI) m/z 388 (M+H$^+$); $^1$H NMR (300 MHz, CDCl$_3$) d 3.07 (m, 4H), 3.77 (d,d, 1H), 3.88 (m, 4H), 4.04 (m, 1H), 4.12 (t, 1H), 4.35 (m, 1H), 4.61 (s, 2H), 4.98 (m, 1H), 6.96 (t, 1H), 7.08 (d,d, 1H), 7.44 (d,d, 1H), 8.69 (s, 1H). Anal. calcd for C$_{16}$H$_{19}$ClFN$_3$O$_3$S: C, 49.55; H, 4.94; N, 10.83. Found: C, 49.38; H, 5.20; N, 10.27.

EXAMPLE 16

(S)-N-[[3-[3-Fluoro-4-(4-moropholinyl)phenyl]-2-oxo-5-oxazolidinyl]methyl]-α,α,α-trifluorothioacetamide (13)

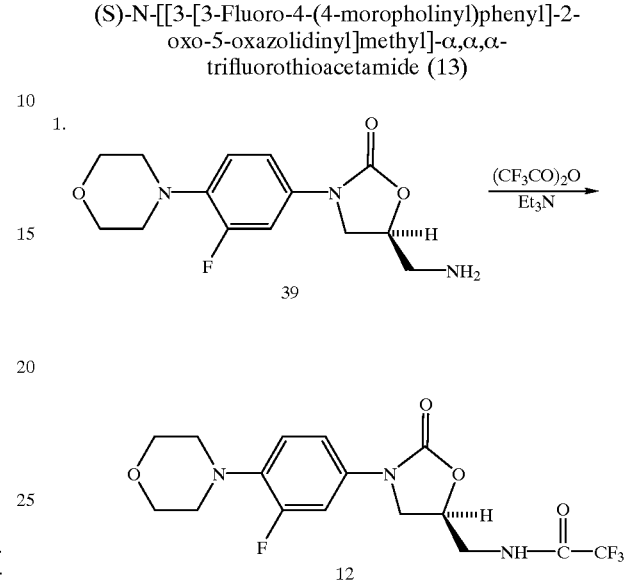

An ice cold stirred solution of 39 (0.590 g, 2.0 mmol) and triethylamine (640 mL, 4.6 mmol) in CH$_2$Cl$_2$ (10 mL) was treated with trifluoroacetic anhydride (325 mL, 2.3 mmol) and kept in the ice bath for 10 min and then at ambient temperature. The reaction was followed by TLC on silica gel with 30% acetone-CH$_2$Cl$_2$. Additional trifluoroacetic anhydride and triethylamine were added after 3 d (64 mL/125 mL), 4 d (100 mL/220 mL) and 6 d (325 mL/1.0 mL). The reaction was complete 1 h after the last addition; it was mixed with CH$_2$Cl$_2$, washed with water and dilute NaCl, dried (Na$_2$SO$_4$) and concentrated. The solid residue was recrystallized from acetone-heptane to give 0.566 g of 12: mp 161–164° C. (dec); MS(EI) m/z 391 (M$^+$). Anal. calcd for C$_{16}$H$_{17}$F$_4$N$_3$O$_4$: C, 49.11; H, 4.38; N, 10.74. Found: C, 48.99; H, 4.56; N, 10.73.

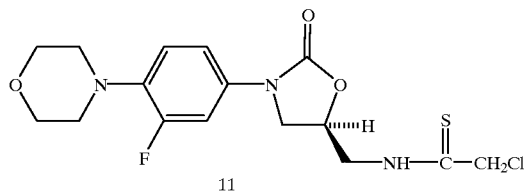

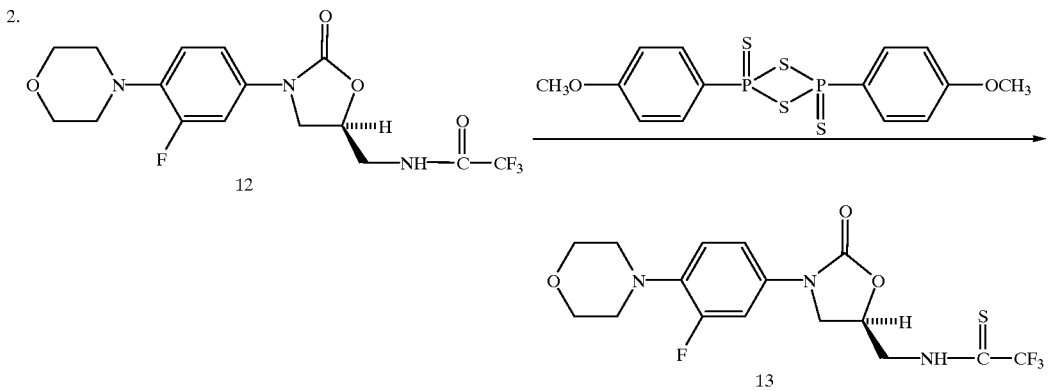

A stirred mixture of 12 (0.391 g, 1.0 mmol) and Lawesson's reagent (0.422 g, 1.1 mmol) in dioxane (10 mL) was refluxed, under nitrogen for 2 h, cooled slowly to ambient temperature and concentrated in vacuo. The residue was flash chromatographed on silica gel with 5–15% acetone-$CH_2Cl_2$ and the product was crystallized from acetone-heptane to give 0.249 g of 13: mp 151–152° C.; MS(EI) m/z 407 ($M^+$), 363, 209, 151, 95; $^1H$ NMR (300 MHz, $CDCl_3$) d 3.05 (m, 4H), 3.75 (d,d, 1H), 3.87 (m, 4H), 3.95 (m, 1H), 4.14 (t, 1H), 4.32 (m, 1H), 5.01 (m, 1H), 6.92 (t, 1H), 7.05 (d,d, 1H), 7.38 (d,d, 1H), 9.03 (s, 1H). Anal. calcd for $C_{16}H_{17}F_4N_3O_3S$: C, 47.17; H, 4.21; N, 10.31. Found: C, 47.09; H, 4.35; N, 10.27.

EXAMPLE 17

(S)-N-[[3-[3-Fluoro-4-(4-morpholinyl)phenyl]-2-oxo-5-oxazolidinyl]methyl]-α-fluorothioacetamide (15)

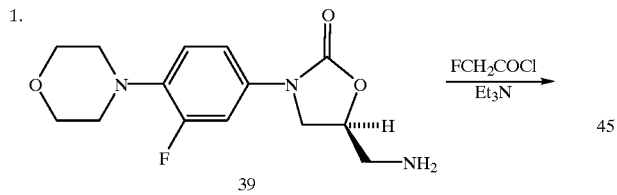

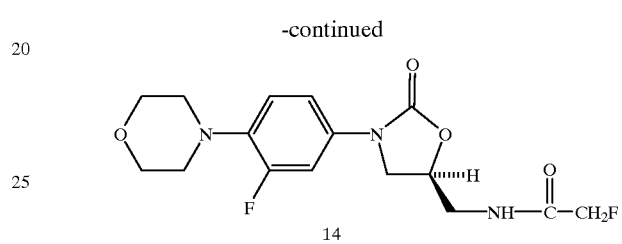

A stirred, ice cold solution of 39 (0.590 g, 2.0 mmol) and triethylamine (611 mL, 4.4 mmol) in $CH_2Cl_2$ (10 mL), under nitrogen, was treated, dropwise, with a solution of fluoroacetyl chloride (220 mL, 2.2 mmol) in $CH_2Cl_2$ (5 mL), kept in the ice bath for 10 min and at ambient temperature for 2 h. It was then diluted with $CH_2Cl_2$, washed with water and dilute NaCl, dried ($Na_2SO_4$) and concentrated. The residue was chromatographed on silica gel with 10–30% acetone-$CH_2Cl_2$ to give 0.180 g of 14: MS(ES) m/z 356 ($M+H^+$), 378 ($M+Na^+$).

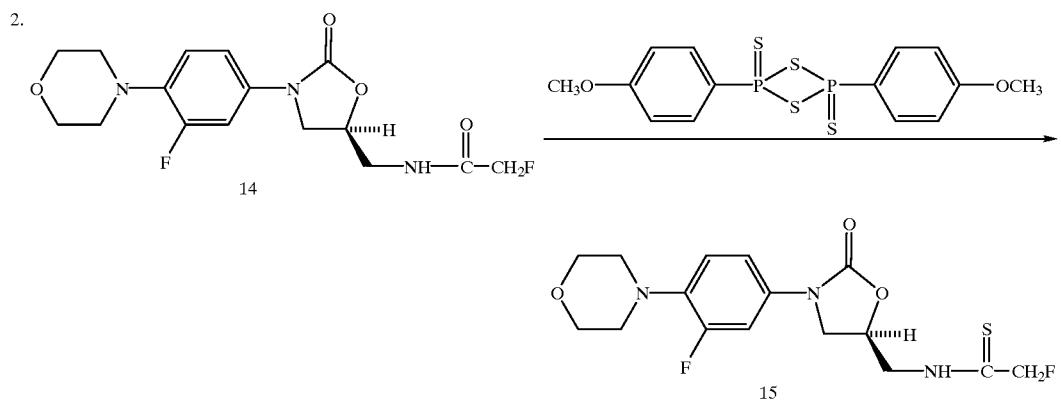

A solution of 14 (0.180 g, 0.507 mmol) in dioxane, under nitrogen, was treated with Lawesson's reagent (0.206 g, 0.51 mmol), warmed at 90–100° C. for 1 h and concentrated in vacuo. The residue was chromatographed on silica gel with 15% acetone-$CH_2Cl_2$ to give 0.161 g of 15: MS(EI) m/z 371 ($M^+$); $^1$H NMR (300 MHz, $CDCl_3$) d 3.05 (m, 4H), 3.78 (d,d, 1H), 3.87 (m, 4H), 4.03 (m, 1H), 4.11 (t, 1H), 4.38 (m, 1H), 4.98 (m, 1H), 5.07 (s, 1H), 5.23 (s, 1H), 6.93 (t, 1H), 7.08 (dd, 1H), 7.42 (d,d, 1H), 8.42 (s, 1H). Anal. calcd for $C_{16}H_{19}F_2N_3O_3S$: C, 51.74; H, 5.16; N, 11.31. Found: C, 51.79; H, 5.31; N, 11.02.

EXAMPLE 18

(S)-N-[[3-[3-Fluoro-4-(4-morpholinyl)phenyl]-2-oxo-5-oxazolidinyl]methyl]-α,α-difluorothioacetamide (17)

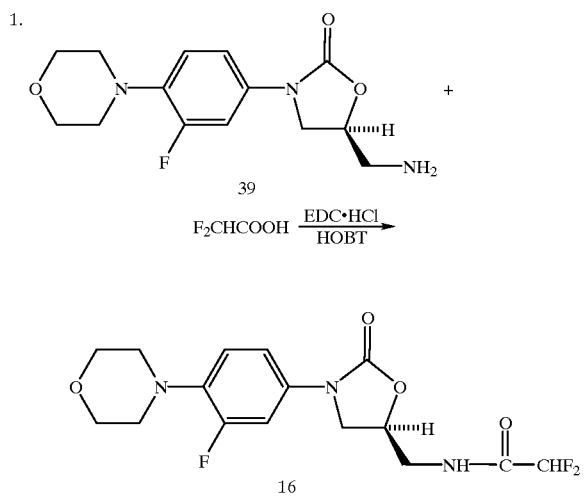

A stirred, ice cold mixture of 39 (0.590 g, 2.0 mmol), difluoroacetic acid (190 mL, 2.0 mmol), and 1-hydroxybenzotriazole (0.297 g, 2:2 mmol) in DMF (5 mL) under nitrogen, was treated with 1-(3-dimethylaminopropyl)-3-ethylcarbodiimide hydrochloride (0.843 g, 4.4 mmol) and kept at ambient temperature for 18 h. It was diluted with $CH_2Cl_2$, washed with water and dilute NaCl, dried ($Na_2SO_4$) and concentrated. The solid residue was crystallized form EtOAc-heptane to give 0.617 g of 16: mp 149–150° C.; 1H NMR (300 MHz, CDCl3) d 3.05 (m, 4H), 3.66 (m, 2H), 3.85 (m, 5H), 4.08 (t, 1H), 4.80 (m, 1H), 5.93 (t, J=53.9 Hz, 1H), 6.92 (t, 1H), 7.06 (m, 2H), 7.39 (d,d, 1H); MS(EI) mlz 373 ($M^+$). Anal. calcd for $C_{16}H_{18}F_3N_3O_4$: C, 51.48; H, 4.86; N, 11.26. Found: C, 51.59; H, 4.91; N, 11.29.

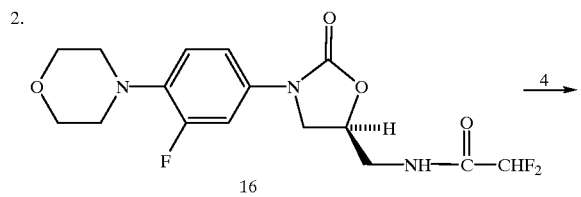

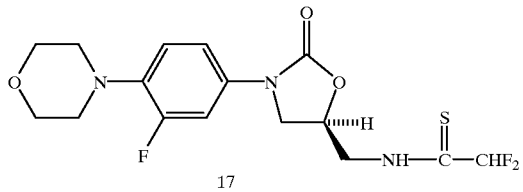

A stirred solution of 16 (0.373 g, 1.00 mmol) in dioxane (10 mL), under nitrogen was treated with Lawesson's reagent (0.404 g, 1.00 mmol), warmed at about 95° C. for 1 h and concentrated in vacuo. Chromatography of the residue on silica gel with 10% acetone-$CH_2Cl_2$ and cyrstallization of the product from EtOAc-heptane gave 0.276 g of 17: mp 125–127° C.; MS(EI) m/z 389 ($M^+$), 345, 305, 247, 209, 195, 151, 138, 123, 109, 95; $^1$H NMR (300 MHz, $CDCl_3$) d 3.05 (m, 4H), 3.76 (d,d, 1H), 3.86 (m, 4H), 4.01 (m, 1H), 4.12 (t, 1H), 4.30 (m, 1H), 4.99 (m, 1H), 6.20 (t, J=55.9 Hz, 1H), 6.92 (t, 1H), 7.06 (d,d, 1H), 7.38 (d,d, 1H), 8.78 (broad s, 1H). Anal. calcd for $C_{16}H_{18}F_3N_3O_3S$: C, 49.35; H, 4.66; N, 10.79. Found: C, 49.37; H, 4.71; N, 10.83.

EXAMPLE 19

(S)-N-[[3-[3-Fluoro-4-(4-morpholinyl)phenyl]-2-oxo-5-oxazolidinyl]methyl]-α-cyanothioacetamide (19)

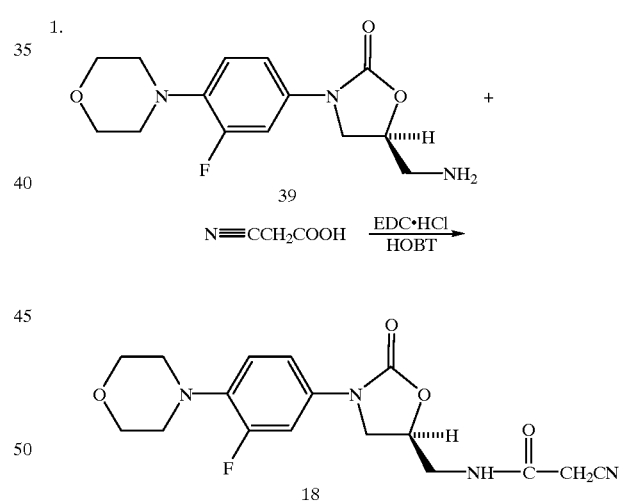

An ice cold, stirred mixture of 39 (0.646 g, 2.19 mmol), cyanoacetic acid (0.179 g, 2.1 mmol) and 1-hydroxybenzotriazole (0.351 g, 2.6 mmol) in DMF (5 mL), under nitrogen, was treated with 1-(3-dimethylaminopropyl)-3-ethylcarbodiimide hydrochloride (0.997 g, 5.2 mmol) and kept at ambient temperature for 24 h. It was diluted with $CH_2Cl_2$, washed with water and dilute NaCl, dried ($Na_2SO_4$) and concentrated. The solid residue was crystallized from EtOAc-heptane to give 0.546 g of 18: mp 172–174° C.: IR (DRIFT) 3316, 2256, 1754, 1684 $cm^{-1}$; MS(EI) m/z 362 ($M^+$). Anal. calcd for $C_{17}H_{19}FN_4O_4$: C, 56.35; H, 5.28; N, 15.46. Found: C, 56.33; H, 5.30; N, 15.36.

2.

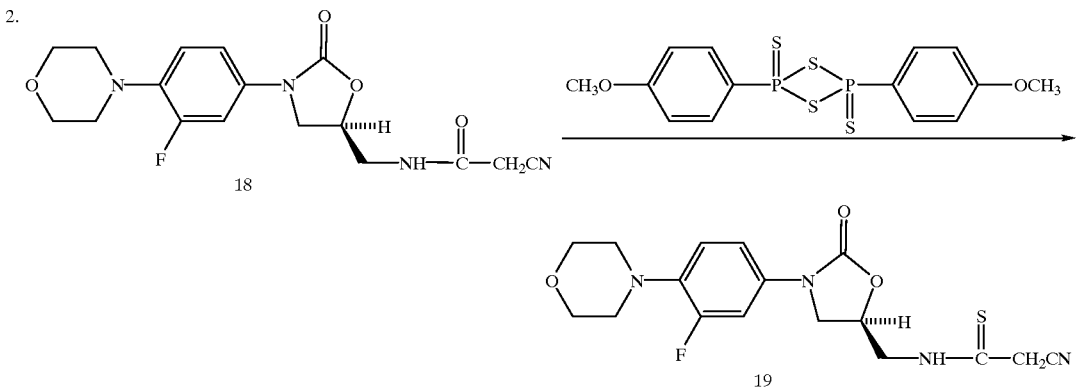

A stirred solution of 18 (0.453 mg, 1.25 mmol) in dioxane (10 mL), under nitrogen, was treated with Lawesson's reagent (0.505 g, 1.25 mmol) and warmed at about 100° C. When the reaction was over (TLC with 30% acetone-$CH_2Cl_2$) the mixture was cooled and concentrated in vacuo. Chromatography of the residue on silica gel witth 10–20% acetone-$CH_2Cl_2$ and crystallization of the product from EtOAc-heptane gave 0.110 g of 19: mp 186–187° C. (dec); MS(ES) m/z 379 (M+H$^+$), 401 (M+Na$^+$); $^1$H NMR (300 MHz, CDCl$_3$) d 3.05 (m, 4H), 3.81 (d,d, 1H), 3.86 (m, 4H), 3.89 (s, 2H), 4.09 (t, 1H), 4.14 (m, 2H), 5.01 (m, 1H), 6.92 (t, 1H), 7.05 (d,d, 1H), 7.34 (d,d, 1H), 9.15 (s, 1H); IR (DRIFT) 3244, 2260, 1754 cm$^{-1}$. Anal. calcd for $C_{17}H_{19}FN_4O_3S$: C, 53.96; H, 5.06; N, 14.81. Found: C, 53.88; H, 5.39; N, 14.61.

EXAMPLE 20

(S)-N-[[3-[3-Fluoro-4-(4-morpholinyl)phenyl]-2-oxo-5-oxazolidinyl]methyl]-α,α-dichlorothioacetamide (21)

1.

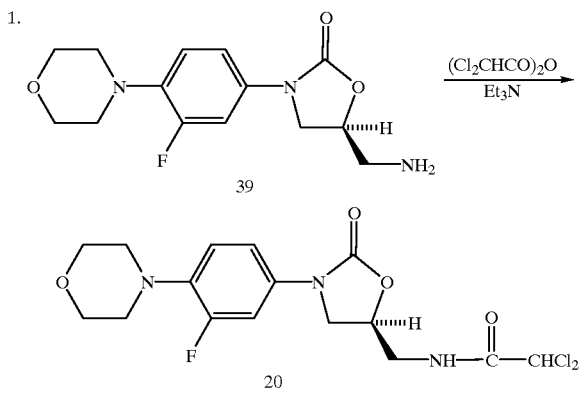

A stirred, ice cold solution of 39 (0.885 g, 3.00 mmol) and triethylamine (975 mL, 7 mmol) in $CH_2Cl_2$ (15 mL), under nitrogen was treated, dropwise with a solution of dichloroacetic anhydride (555 mL, 3.5 mmol) in $CH_2Cl_2$ (5 mL) and kept in the ice bath for 15 min and at ambient temperature for 18 h. It was diluted with $CH_2Cl_2$, washed with water, saturated $NaHCO_3$ and dilute NaCl, dried ($Na_2SO_4$) and concentrated. Chromatography of the residue on silica gel with 10% acetone-$CH_2Cl_2$ and crystallization of the product from acetone-heptane gave 0.463 g of 20: mp 197–198° C. (dec); MS(ES) m/z 406 (M+H$^+$), 428 (M+Na$^+$); $^1$H NMR (300 MHz, CDCl$_3$) d 3.05 (m, 4H), 3.75 (m, 3H), 3.86 (m, 4H), 4.07 (t, 1H), 4.83 (m, 1H), 5.94 (s, 1H), 6.92 (t, 1H), 7.06 (m, 2H), 7.41 (d,d, 1H).

2.

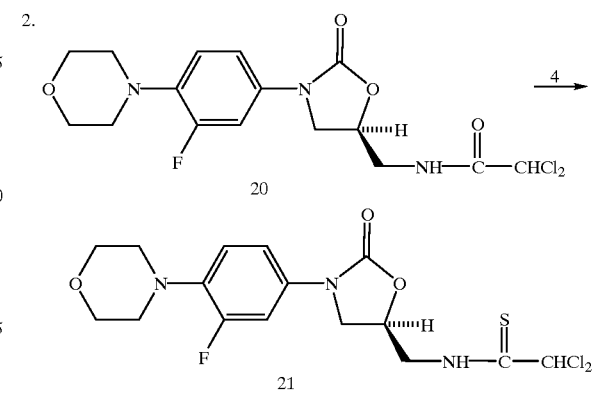

A stirred solution of 20 (0.305 g, 0.75 mmol) in dioxane (5 ml), under nitrogen, was treated with Lawesson's reagent (0.202 g, 0.5 mmol), warmed at about 90° C. for 1 hour, cooled and concentrated in vacuo. Chromatography of the residue on silica gel first with 30% acetone-heptane and then with 10% acetone-methylene chloride and crystallization of rh product form methylene chloride-heptane gave 0.203 g with 21: mp 143–144° cd.; HR17S (EI) calculated for $C_{16}H_{18}cl_2$ F $N_3$ $O_3$ S(M) 421.0431. Anal. calcd for $C_{16}H_{18}cl_2$ F $N_3$ $O_3$ S, C, 45.51; H, 4.30; N, 9.95. Found: C, 45.47; H, 4.24; H, 9.88.

EXAMPLE 21

(S)-N-[[3-[3-Fluoro-4-(4-morpholinyl)phenyl]-2-oxo-5-oxazolidinyl]methyl]-α-(methoxycarbonyl)thioacetamide (23)

1.

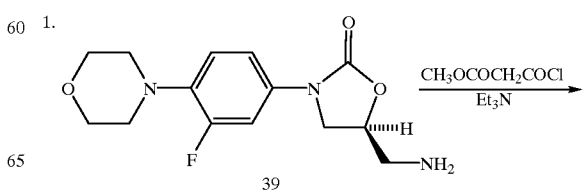

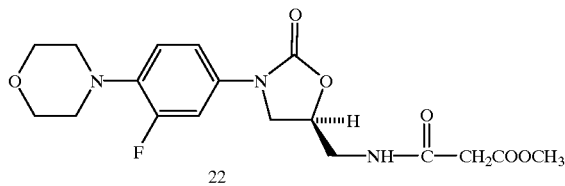

A stirred solution of 39 (0.955 g, 3.2 mmol) and triethylamine (650 mL, 4.5 mmol) in $CH_2Cl_2$ (50 mL), under nitrogen, was treated, dropwise during 15–20 min with a solution of methyl malonyl chloride (475 mL, 4.3 mmol) in $CH_2Cl_2$ (10 mL) and kept at ambient temperature for 3 days. It was then washed with water and dilute NaCl, dried and concentrated. The residue was flash chromatographed on silica gel with 15–30% acetone-$CH_2Cl_2$ and the product was crystallized form acetone-hexane to give 0.873 g of 22: mp 150–151° C.; $^1$H NMR (300 MHz, $CDCl_3$) d 3.03 (m, 4H), 3.34 (s, 2H), 3.67 (s, 3H), 3.69 (m, 2H), 3.76 (d,d, 1H), 3.85 (m, 4H), 4.00 (t, 1H), 4.78 (m, 1H), 6.90 (t, 1H), 7.06 (d,d, 1H), 7.41 (d,d, 1H), 7.57 (t, 1H); MS(ES) m/z 396 (M+H$^+$), 418 (M+Na$^+$); HRMS (FAB) calcd for $C_{18}H_{23}FN_3O_6$ (M+H$^+$) 396.1571, found 396.1579. Anal. calcd for $C_{18}H_{22}FN_3O_6$: C, 54.68; H, 5.61; N, 10.63. Found: C, 54.69; H, 5.68; N, 10.58.

2.

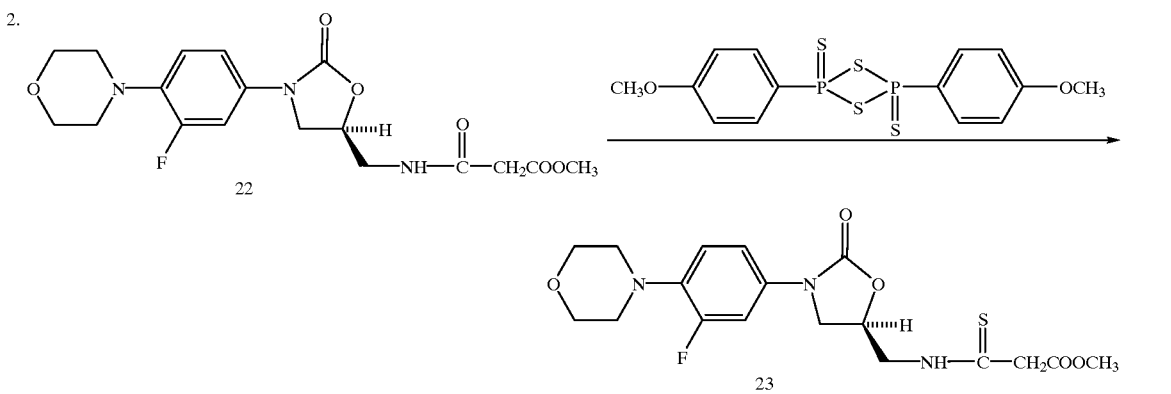

A stirred solution of 22 (0.395 g, 1.0 mmol) in dioxane (10 mL), under nitrogen, was treated with Lawesson's reagent (0.202 g, 0.5 mmol) and kept at ambient temperature for 4 h 10 min and at 80–90° C. for 1.5 h. The reaction was followed by TLC on silica gel with 10% MeOH—$CHCl_3$. At this time a new, less polar product had begun to form. It was kept at ambient temperature for 18 h and at 80° C. for 2 h; additional Laewsson's reagent (40 mg, 0.099 mmol) was added and warming at 80° C. was continued for 2 h; some starting material still remained. The mixture was concentrated and the residue was chromatographed on silica gel with 15% acetone-$CH_2Cl_2$ to give 0.348 g of 23: $^1$H NMR (300 MHz, $CDCl_3$) d 3.05 (m, 4H), 3.71 (s, 3H), 3.81 (d,d, 1H), 3.86 (m, 4H), 3.88 (s, 2H), 4.07 (t, 1H), 4.19 (m, 2H), 4.99 (m, 1H), 6.91 (t, 1H), 7.07 (d,d, 1H), 7.42 (d,d, 1H), 9.52 (s, 1H); IR (DRIFT) 3269, 1743 cm$^{-1}$; MS(EI) m/z 411 (M$^+$). Anal. calcd for $C_{18}H_{22}FN_3O_5S$: C, 52.54; H, 5.39; N, 10.21. Found: C, 52.58; H, 5.43; N, 10.14.

EXAMPLE 22

(S)-N-[[3-[4-[1-[1,2,4]Triazolyl]phenyl]-2-oxo-5-oxazolidinyl]methyl]thioacetamide (25)

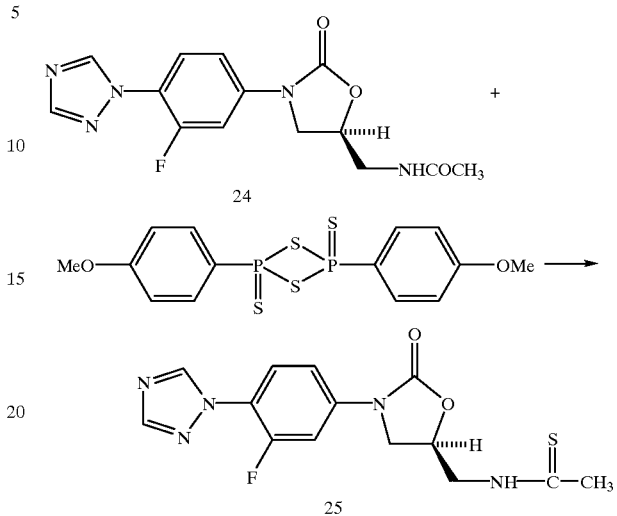

A stirred mixture of 24$^{10,11}$ (0.150 g, 0.470 mmol) and dioxane (12.5 mL), under nitrogen, was treated with Lawesson's reagent (0.20 g, 0.50 mmol), refluxed for 1.5 h, kept at ambient temperature for 18 h and concentrated in vacuo. Flash chromatography of the residue on silica gel with 5% MeOH—$CHCl_3$ gave the product which was crystallized from MeOH to give 0.100 g (63.4%) of 25: mp 161–163° C.; $^1$H NMR [300 MHz, $(CD_3)_2SO$] d 2.43 (s, 3H), 3.87 (m, 3H), 4.22 (t, 1H), 4.99 (m, 1H), 7.51 (d, 1H), 7.77 (m, 2H), 8.26 (s, 1H), 8.97 (d, 1H), 10.35 (broad s, 1H); IR (mull) 3259, 3226, 3044, 1752 cm$^{-1}$; MS(ES) m/z 336 (M+H$^+$), 358 (M+Na$^+$). Anal. calcd for $C_{14}H_{14}FN_5O_2S$: C, 50.14; H, 4.21; N, 20.88. Found: C, 50.18; H, 4.26; N, 20.94.

EXAMPLE 23

(S)-N-[[3-[4-[1-[1,2,4]Triazolyl]phenyl]-2-oxo-5-oxazolidinyl]methyl]thioacetamide (25)

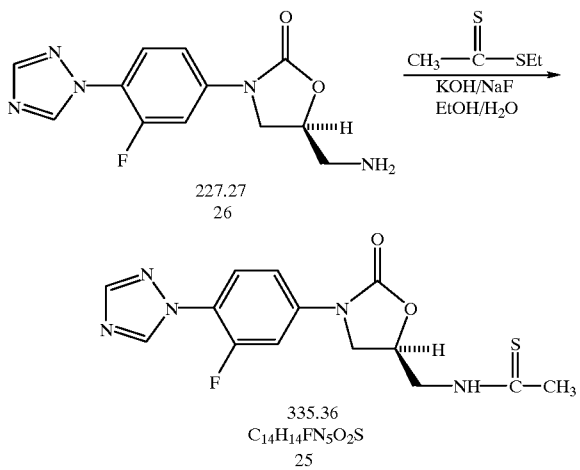

A stirred mixture of 26[10,12] (0.26 g, 0.938 mmol), ethyl dithioacetate (0.12 g, 0.998 mmol), sodium fluoride (0.040 g, 0.953 mmol) and absolute EtOH (10 mL), under nitrogen, was treated during 5 min with a solution of 0.97M KOH (1.03 mL) in EtOH and kept at ambient temperature for 2 h. It was then diluted with $CH_2CL_2$ (75 mL), washed with water, 1M $KHSO_4$, water and brine and evaporated. The residue was flash chromatographed on silica gel with 5% MeOH—$CHCl_3$ and the product was crystallized from MeOH to give 0.118 g, mp 164–165° C. (dec) and 0.026 g, mp 162–163° C. (dec) of 25.

EXAMPLE 24

(S)-N-[[3-[1-(Hydroxyacetyl)-5-indolinyl]-2-oxo-5-oxazolidinyl]methyl]thioacetamide (28)

1.
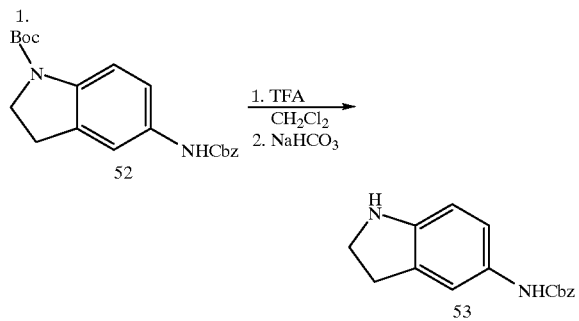

A stirred, ice cold solution of 52[13,14] (8.80 g, 0.0240 mol) in $CH_2Cl_2$ (25 mL) was treated during 20 min with a solution of trifluoroacetic acid (25 mL) in $CH_2Cl_2$ (10 mL). The mixture was kept in the ice bath for 2 h 15 min and concentrated under reduced pressure. A solution of the residue in $CH_2Cl_2$ was washed with saturated $NaHCO_3$ and dilute NaCl, dried ($Na_2SO_4$) and concentrated. The residue was used in the next reaction without further purification. A sample of this material (53) had: $^1H$ NMR (300 MHz, $CDCl_3$) d 3.00 (t, 2H), 3.54 (t, 2H), 3.85 (broad s, 1H), 5.17 (s, 2H), 6.59 (d, 1H), 6.66 (broad s, 1H), 6.91 (d, 1H), 7.23 (s, 1H), 7.36 (m, 5H); MS m/z 269 (M+H$^+$).

2.
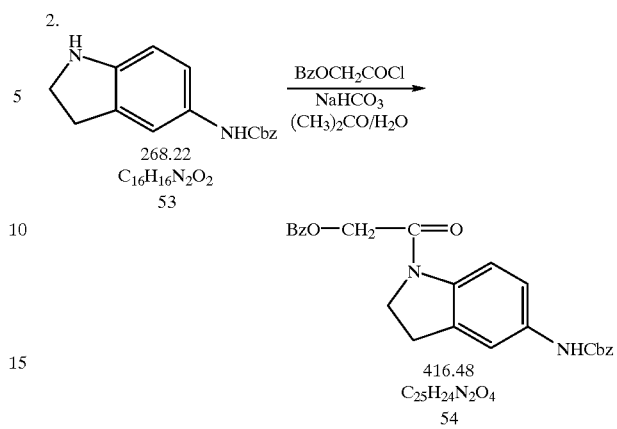

An ice cold, stirred mixture of 53 (crude product from the previous reaction), acetone (200 mL), saturated $NaHCO_3$ (200 mL) and water (30 mL) was treated, dropwise during 20 min, with a solution of benzyloxyacetyl chloride (4.70 mL, 0.030 mol) in acetone (55 mL), warmed slowly to ambient temperature and kept for 18 h. Additional benzyloxyacetyl chloride (1.0 mL) in acetone 35 mL) was added dropwise and the mixture was kept at ambient temperature for an additional 3 h and diluted with EtOAc and water. A solid was collected by filtration and dried to give 4.00 g of crude product. The EtOAc solution was dried ($Na_2SO_4$) and concentrated to give 5.36 g of additional crude product. Crystallization of the product from EtOAc gave a total of 6.35 g of 54[14], mp 157–169.5° C. The analytical sample had: mp 158–159.5° C.; $^1H$ NMR (300 MHz, $CDCl_3$) δ3,16 (t,2H), 4.01(t,2H), 4.21 (s, 2H), 4.69 (s, 2H), 5.19 (s, 2H), 6.67 (s, 1H), 6.97 (d, 1H), 7.36 (m, 10H), 7.50 (braod s, 1H), 8.15 (d, 1H); MS(EI) m/z (relative intensity) 416 (M$^+$, 9), 310 (8), 202 (10), 133 (8), 92 (8), 91 (99), 79 (7), 77 (9), 65 (12), 51 (6); IR (mull) 2381, 1722, 1659, 1608, 1558 cm$^{-1}$. Anal. calcd for $C_{25}H_{24}N_2O_4$: C, 72.10; H, 5.81; N, 6.73. Found: C, 72.05; H, 5.86; N, 6.68.

3.
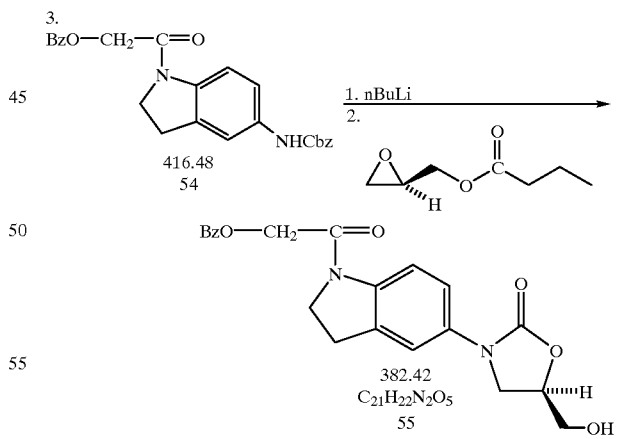

A stirred suspension of 54 (1.16 g, 2.78 mmol) in THF (42 mL) was cooled, under nitrogen, to −78° C. and treated, dropwise, during 5 min with 1.6M n-BuLi in hexane (1.83 mL). It was kept at −78° C. for 50 min, treated, dropwise, during 5 min with a solution of (R)-(−)-glycidyl butyrate (0.500 g, 3.47 mmol) in THF (2 mL), allowed to warm to ambient temperature during 3 h and kpet for 18 h. It was then diluted with EtOAc, washed with saturated $NH_4Cl$, water and brine, dried (MgSO$_4$) and concentrated. Chromatography of the residue on silica gel with 3% MeOH-0.2% NH$_4$OH—CHCl$_3$ gave 0.60 g (56%) of 55[14]: $^1$H NMR [300 MHz, (CD$_3$)$_2$SO] δ3.14 (t, 2H), 3.59 (m, 2H), 3.79 (d,d, 1H), 4.03 (m, 3H), 4.29 (s, 2H), 4.58 (s, 2H), 4.65 (m, 1H), 5.20 (t, 1H), 7.31 (m, 6H), 7.55 (s, 1H), 8.03 (d, 1H); MS(ES) m/z 383 (M+H$^+$), 405 (M+Na$^+$).

4.

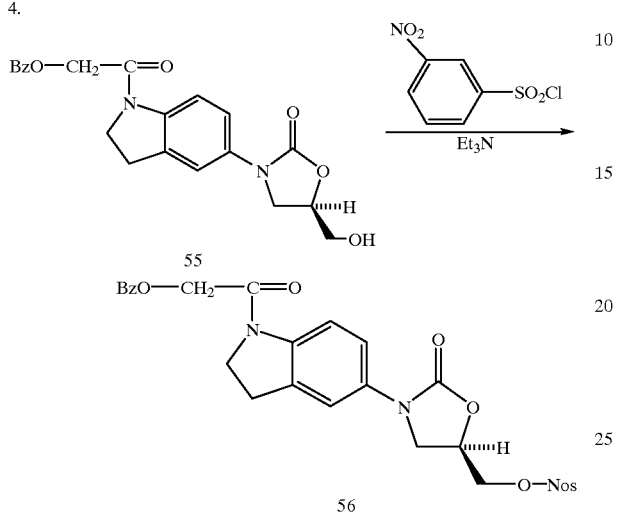

An ice cold, stirred mixture of 55 (0.60 g, 1.57 mmol), triethylamine (2.2 mL), and CH$_2$Cl$_2$ (12 mL), under nitrogen, was treated with 3-nitrobenzenesulfonyl chloride (0.44 g, 1.99 mmol) and kept in the ice bath for 30 min and at ambient temperature for 60 min. It was then diluted with CH$_2$Cl$_2$, washed with water and brine, dried (Na$_2$SO$_4$) and concentrated. Chromatography of the residue on silica gel with 15% CH$_3$CN—CH$_2$Cl$_2$ gave 0.70 g of 56: $^1$H NMR (300 MHz, CDCl$_3$) d 3.19 (t, J=8.3 Hz, 2H), 3.88 (d,d, 1H), 4.04 (t, J=8.4 Hz, 2H), 4.14 (t, 1H), 4.23 (s, 2H), 4.42 (m, 2H), 4.70 (s, 2H), 4.84 (m, 1H), 6.97 (m, 1H), 7.34 (m, 5H), 7.58 (s, 1H), 7.81 (t, 1H), 8.22 (m, 2H), 8.53 (m, 1H), 8.73 (m, 1H); MS(ES) m/z 568 (M+H$^+$), 590 (M+Na$^+$).

5.

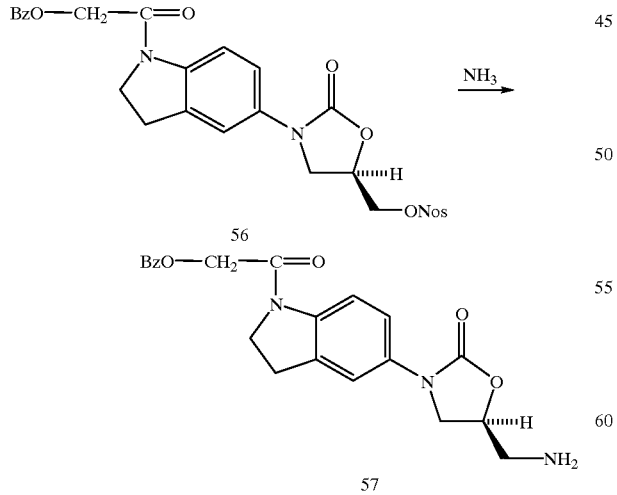

A stirred mixture of 56 (crude product from 0.00314 mol of 55), acetonitride (70 ml), isopropanol (70 mL) and 29% ammonium hydroxide (70 mL) was warmed at 40–44° C. for 7 h and kept at ambient temperature for 18 h. It was concentrated in vacuo to an aqueous residue with was extracted with CH$_2$Cl$_2$. The extract was washed with water and brine, dried (Na$_2$SO$_4$) and concentrated. Chromatography of the residue on silica gel with 8% MeOH-0.5% NH$_4$OH—CHCl$_3$ gave 1.05 g of 57: $^1$H NMR [300 MHz, (CD$_3$)$_2$SO] d 2.78 (m, 2H), 3.13 (t, 2H), 3.82 (d,d, 1H), 4.01 (m, 3H), 4.29 (s, 2H), 4.58 (s, 2H), 4.58 (m, 1H), 7.31 (m, 6H), 7.54 (broad s, 1H), 8.03 (d, 1H); MS(ES) m/z 382 (M+H$^+$), 404 (M+Na$^+$).

6.

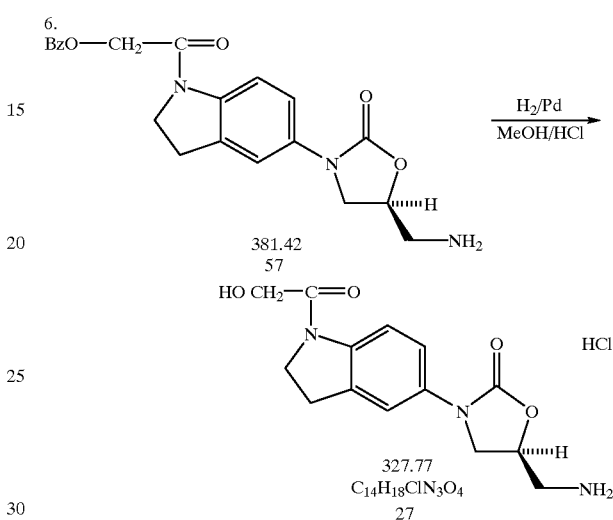

A mixture of 57 (0.46 g, 1.21 mmol), MeOH (150 mL), 1 M HCl (1.2 mL) and 5% palladium-on-carbon catalyst (250 mg) was hydrogenated at an initial pressure of 49 psi for 5 h. Additional 1M HCl (0.5 mL) and catalyst (100 mg) were added and hydrogenation was continued for 18 h. The catalyst was removed by filtration and the filtrate was concentrated to give 0.34 g of 27: $^1$H NMR [300 MHz, (CD$_3$)$_2$SO] δ3.15 (t, 2H), 3.22 (broad s, 2H), 3.84 (d,d, 1H), 4.00 (t, 2H), 4.15 (s, 2H), 4.15 (m, 1H), 4.92 (m, 1H), 7.24 (q, 1H), 7.50 (d, 1H), 8.03 (d, 1H), 8.37 (broad s, 3H); MS(ES) m/z 2.92 (M+H$^+$).

7.

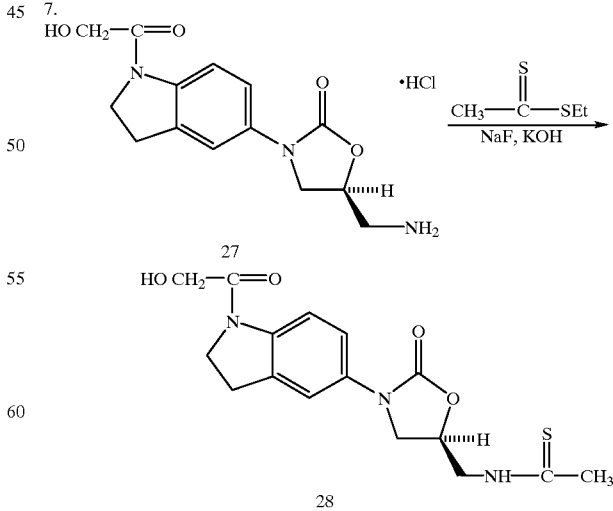

A suspension of 27 (0.10 g, 0.34 mmol) in a mixture of EtOH (15 mL) and 0.97M KOH (0.7 mL) was added, under nitrogen to a stirred mixture of ethyl dithioacetate (0.0412 g, 0.343 mmol) and sodium fluoride (0.0137 g, 0.326 mmol) in EtOH (5 mL) and the mixture was kept at ambient temperature for 2 h 15 min. Additional 0.97M KOH (0.2 mL), sodium iodide (6 mg) and ethyl dithioacetate (20 mg) were added and the mixture was stirred for 2 h, mixed with CH$_2$Cl$_2$ (150 mL), washed with water, 1M KHSO$_4$ and brine, dried (Na$_2$SO$_4$) and concentrated. The residue was crystallized from acetone to give 0.0404 g of 28: mp 175–176° C. (dec); MS (FAB) m/z 350 (M+H$^+$), 349 (M$^+$), 331, 316, 205, 73; HR MS (FAB) calcd for C$_{16}$H$_{20}$N$_3$O$_4$S (M+H$^+$) 350.1174, found 350.1183; $^1$H NMR [300 MHz, (CD$_3$)$_2$SO] d 2.42 (s, 3H), 3.14 (t, 2H), 3.79 (d,d, 1H), 3.89 (t, 2H), 4.00 (t, 2H), 4.12 (m, 3H), 4.83 (t, 1H), 4.90 (m, 1H), 7.25 (d, 1H), 7.50 (s, 1H), 8.03 (d, 1H), 10.35 (s, 1H); IR (DRIFT) 3255, 3223, 3068, 1747, 1639, 1614 cm$^{-1}$.

EXAMPLE 25

(S)-N-[[3-[3-Fluoro-4-[4-(hydroxyacetyl)-1-piperazinyl]phenyl]-2-oxo-5-oxazolidinyl]methyl]thioacetamide (30)

1.

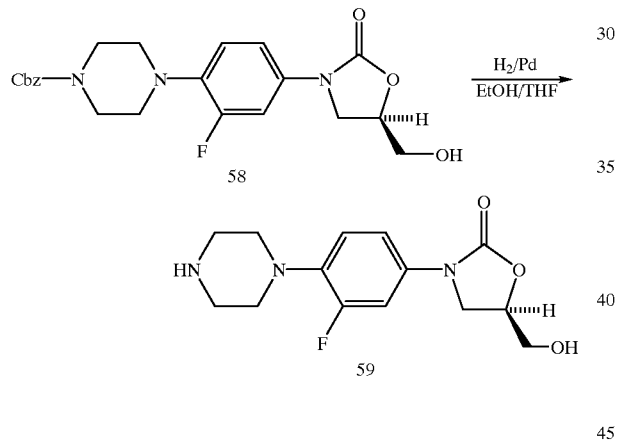

A mixture of 58[15] (3.00 g, 7.00 mmol), THF (60 mL), absolute EtOH (100 mL) and 10% palladium-on-carbon catalyst (415 mg) was hydrogenated at an initial pressure of 58 psi for 2 h 50 min. The catalyst was removed by filtration and the filtrate was concentrated in vacuo to give 2.67 g of 59 which was used without further purification in the next reaction: $^1$H NMR (300 MHz, CDCl$_3$) d 2.16 (broad s), 3.02 (m, 8H), 3.73 (d,d, J=3.9, 12.6 Hz, 1H), 3.96 (m, 3H), 4.72 (m, 1H), 6.92 (t, J=9.2 Hz, 1H), 7.11 (m, 1H), 7.43 (d,d, J=2.6, 14.3 Hz, 1H); MS(ES) m/z 296 (M+H$^+$).

2.

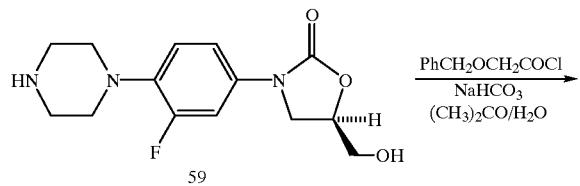

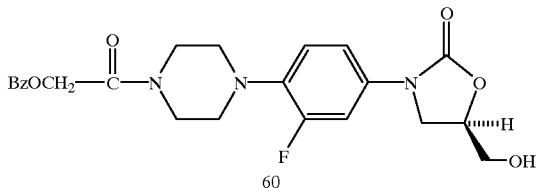

A stirred, ice cold mixture of 59 (2.67 g from the previous reaction), acetone (190 mL) and saturated NaHCO$_3$ (70 mL) was treated, dropwise during 2–3 min with a solution of benzyloxyacetyl chloride (1.34 mL, 8.61 mmol) in acetone (25 mL), kept in the ice bath for 1 h and diluted with EtOAc. The aqueous layer was extracted with EtOAc and the combined organic solution was washed with dilute NaCl, dried and concentrated. Chromatography of the residue on silica gel with 30% acetone-CH$_2$Cl$_2$ gave 2.64 g of 60: $^1$H NMR (300 MHz, CDCl$_3$) d 2.28 (broad s, 1H), 3.00 (m, 4H), 3.66 (m, 2H), 3.77 (m, 3H), 3.96 (m, 3H), 4.22 (s, 2H), 4.61 (s, 2H), 4.74 (m, 1H), 6.88 (t, J=9.2 Hz, 1H), 7.12 (m, 1H), 7.35 (s, 5H), 7.46 (d,d, J=2.6, 14.2 Hz, 1H); IR (mull) 3406, 1748, 1647 cm$^{-1}$; HRMS(EI) calcd for C$_{23}$H$_{26}$FN$_3$O$_5$ (M$^+$) 443.1856, found 443.1842.

3.

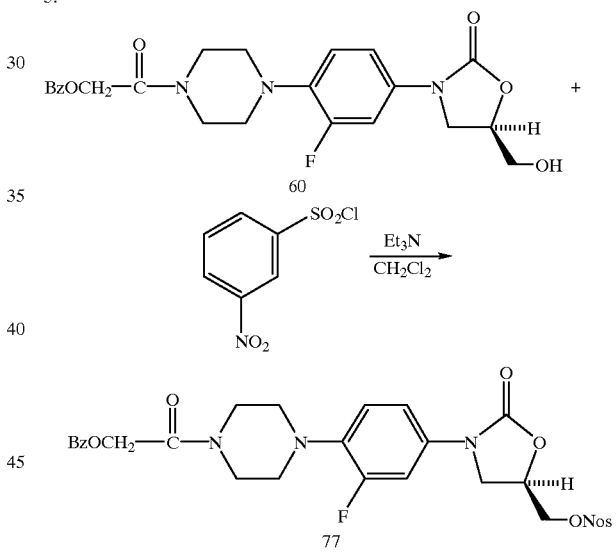

A stirred, ice cold mixture of 60 (2.64 g, 6.00 mmol) and triethylamine (1.14 mL, 8.16 mmol) in CH$_2$Cl$_2$ (200 mL), under nitrogen, was treated with 3-nitrobenzenesulfonyl chloride (1.78 g, 8.04 mmol), warmed to ambient temperature and kept for 5 h 20 min. Additional 3-nitrobenzenesulfonyl chlroide (180 mg) and triethylamine (0.20 mL) were added and the mixture was kept at ambient temperature for 18 h, diluted with CH$_2$Cl$_2$ and washed with water and dilute NaCl, dried (Na$_2$SO$_4$) and concentrated. Chromatography of the residue on silica gel with 40–60% acetone-hexane gave 3.36 g of 77: $^1$H NMR (300 MHz, CDCl$_3$) d 3.02 (broad s, 4H), 3.66 (broad s, 2H), 3.78 (broad s, 2H), 3.87 (d,d, J=5.9, 9.1 Hz, 1H), 4.09 (t, J=9.2 Hz, 1H), 4.22 (s, 2H), 4.41 (m, 2H), 4.61 (s, 2H), 4.84 (m, 1H), 6.88 (t, J=9.1 Hz, 1H), 7.02 (m, 1H), 7.35 (m, 6H), 7.82 (t, J=8.0 Hz, 1H), 8.23 (m, 1H), 8.53 (m, 1H), 8.73 (m, 1H); MS(ES) m/z 629 (M+H$^+$).

4.

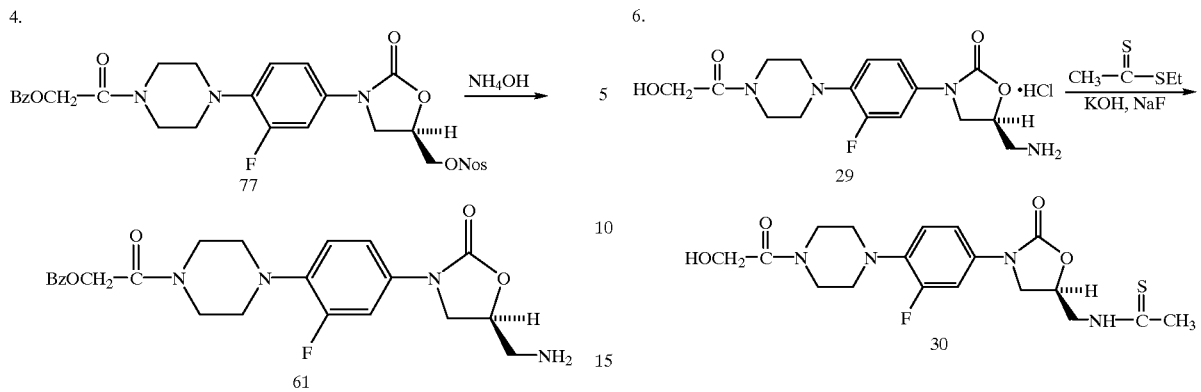

A solution of 77 (3.36 g, 5.34 mmol) in a mixture of acetonitrile (90 mL), isopropanol (90 mL) and concentrated ammonium hydroxide (90 mL) was warmed at 40–45 °C. for 18 h, treated with addition. ammonium hydroxide (30 mL), warmed at 40–45° C. for 8 h, treated with additional ammonium hydroxide (25 mL) and warmed at 45° C. for 18 h. It was then mixed with water and extracted with $CH_2Cl_2$. The extract was washed with dilute NaCl, dried ($Na_2SO_4$) and concentrated. Chromatography of the residue on silica gel with 5% MeOH-0.5% $NH_4OH$—$CHCl_3$ gave 2.44 g of 61: $^1H$ NMR (300 MHz, $CDCl_3$) d 1.50 (broad s), 3.04 (m, 6H), 3.65 (broad s, 2H), 3.81 (m, 3H), 3.99 (t, 1H), 4.21 (s, 2H), 4.61 (s, 2H), 4.66 (m, 1H), 6.88 (t, 1H), 7.12 (m, 1H), 7.33 (m, 5H), 7.47 (d,d, 1H); MS(ES) m/z 443 (M+H$^+$).

5.

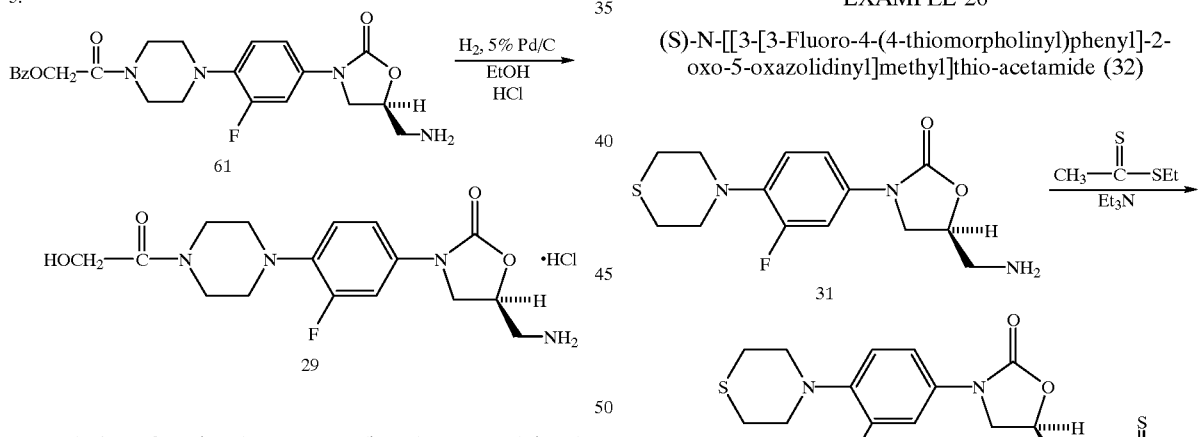

A solution of 61 (1.45 g, 3.3 mmol) and 1.0N HCl (3.65 mL) in 95% EtOH (150 mL) was treated with 5% palladium-on-carbon catalyst (500 mg) and hydrogenated at an initial pressure of 54 psi for 20 h 15 min. Additional 1.0N HCl (0.5 mL) and catalyst (100 mg) were added and hydrogenation was continued for 20 h 30 min at an initial pressure of 60 psi. The reaction was compete by TLC; it was neutralized with concentrated $NH_4OH$, filtered and concentrated in vacuo to give 1.18 g of 29: $^1H$ NMR [300 MHz, $(CD_3)_2SO$] d 2.94 (broad s, 4H), 3.19 (m, 2H), 3.48 (broad s, 2H), 3.60 (broad s, 2H), 3.84 (m, 1H), 4.14 (m, 3H), 4.66 (broad s, 1H), 4.93 (m, 1H), 7.07 (t, 1H), 7.16 (d,d, 1H), 7.48 (d,d, 1H), 8.04 (broad s); IR (mull) 3420, 3099, 3040, 3008, 1755, 1641 cm$^{-1}$; MS(ES) m/z 353 (M+H$^+$). Anal. calcd for $C_{16}H_{22}ClFN_4O_4$: C, 49.42; H, 5.70; Cl, 9.12; N, 14.41. Found: C, 48.16; H, 5.82; Cl, 10.00; N, 14.28.

6.

A stirred mixture of ethyl dithioacetate (180 mL, 1.56 mmol), sodium fluoride (72 mg, 1.7 mmol), 29 (500 mg, 1.29 mmol) and EtOH (70 mL) under nitrogen, was treated with 0.97M KOH (1.46 mL, 1.42 mmol) and the resulting solution was kept at ambient temperature for 3 h 35 min, diluted with $CHCl_3$, washed with water and dilute NaCl, dried ($Na_2SO_4$) and concentrated. Chromatography of the residue on silica gel with 5% MeOH-0.5% $NH_4OH$—$CHCl_3$ and crystallization of the resulting product from absolute EtOH gave 0.238 mg (44.9%) 30: mp 163–165° C.; $^1H$ NMR (300 MHz, $CDCl_3$) d 2.60 (s, 3H), 3.06 (m, 4H), 3.45 (m, 2H), 3.61 (m, 1H), 3.82 (m, 3H), 4.07 (m, 2H), 4.25 (m, 3H), 4.97 (m, 1H), 6.91 (t, 1H), 7.07 (m, 1H), 7.45 (d,d, 1H), 7.91 (broad s, 1H); MS(FAB) m/z (relative intensity) 411 (M+H+, 100), 410 (M$^+$, 66.5), 266 (3.1); IR 3292, 1733, 1653 cm$^{-1}$. Anal. calcd for $C_{18}H_{23}FN_4O_4S$: C, 52.67; H, 5.65; N, 13.65. Found: C, 52.76; H, 5.58; N, 13.64.

EXAMPLE 26

(S)-N-[[3-[3-Fluoro-4-(4-thiomorpholinyl)phenyl]-2-oxo-5-oxazolidinyl]methyl]thio-acetamide (32)

An ice cold, stirred mixture of 31 (0.38 g, 0.0012 mol) and triethylamine (0.38 mL, 0.0027 mol) in THF (12 mL), under nitrogen, was treated with ethyl dithioacetate (0.16 mL, 0.0014 mol) and then kept at ambient temperature for 24.5 h and concentrated in vacuo. A solution of the residue in $CH_2Cl_2$ was washed with saturated $NaHCO_3$, water and brine, dried ($MgSO_4$) and concentrated. Crystallization of the residue from EtOAc-hexane gave 0.355 g of 32: mp 155–156° C.; MS(ES) m/z 370 (M+H$^+$), 392 (M+Na$^+$); IR (DRIFT) 3206, 3042, 1759, 1738 cm$^{-1}$; $^1H$ NMR (300 MHz, $CDCl_3$) d 2.60 (s, 3H), 2.95 (s, 4H), 3.43 (m, 4H), 3.82 (d, d, 1H), 4.08 (m, 2H), 4.27 (m, 1H), 4.98 (m, 1H), 7.06 (m, 1H), 7.33 (broad s, 1H), 7.51 (d, 1H), 8.03 (broad s, 1H). Anal. calcd for $C_{16}H_{20}FN_3O_2S_2$: C, 52.01; H, 5.46; N, 11.37. Found: C, 51.86; H, 5.43; N, 11.20.

EXAMPLE 27

(S)-N-[[3-[3-Fluoro-4-(4-thiomorpholinyl)phenyl]-2-oxo-5-oxazolidinyl]methyl]thio-acetamide, thiomorpholine S-oxide (34)

1.

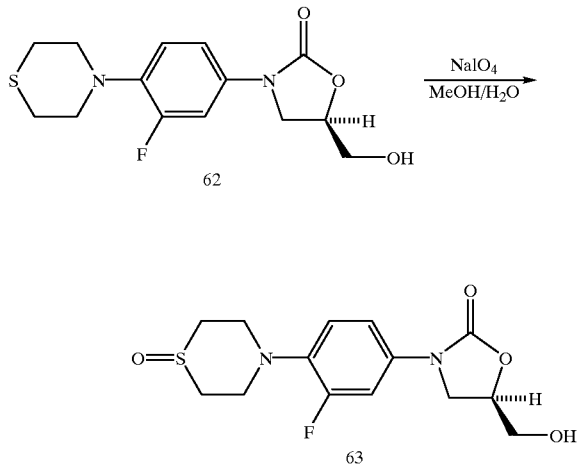

An ice cold, stirred mixture of sodium metaperiodate (1.08 g, 5.05 mmol) and water (12 mL), under nitrogen, was treated with 62[16] (1.5 g, 4.8 mmol) and MeOH (17 mL) and kept at 6° C. for 18 h and at 4° C. for 3 h. It was then treated with additional sodium metaperiodate (0.1 g), kept at 4° C. for 3 h and extracted with $CHCl_3$. The extract was dried ($MgSO_4$) and concentrated to give 1.4 g of 63: $^1$H NMR [300 MHz, $(CD_3)_2SO$] d 2.84 (m, 2H), 3.01 (m, 2H), 3.16 (m, 2H), 3.50 (m, 3H), 3.65 (m, 1H), 3.77 (d,d, 1H), 4.03 (t, 1H), 4.66 (m, 1H), 5.18 (t, 1H), 7.16 (m, 2H), 7.52 (m, 1H); MS(ES) m/z 329 (M+H$^+$), 351 (M+Na$^+$).

2.

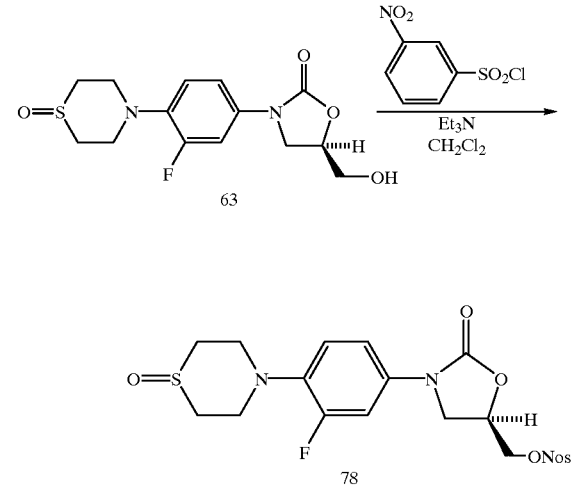

An ice cold, stirred mixture of 63 (1.27 g, 3.87 mmol) and triethylamine (0.732 mL, 5.25 mmol) in $CH_2Cl_2$ (130 mL), under nitrogen, was treated with m-nitrobenzenesulfonyl chloride (1.15 g, 5.19 mmol) and kept at ambient temperature for about 24 h. It was diluted with $CH_2Cl_2$, washed with water and brine, dried ($Na_2SO_4$) and concentrated to give 78 which was used in the next reaction without purfication.

3.

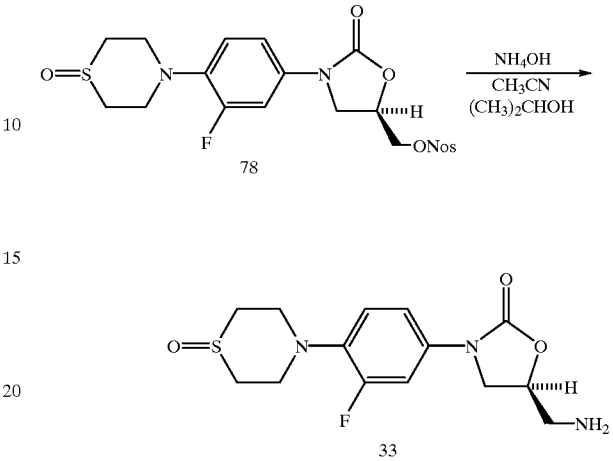

A stirred mixture of the product (78) from the previous reaction, acetonitrile (70 mL) and isopropanol (70 mL) was treated with concentrated ammonium hydroxide (70 mL, 29.9% $NH_3$) and kept at 40° C. for 2 h, at ambient temperature for 18 h and at 40–45° C. for 4 h; it was concentrated to about 50 mL, diluted with water and extracted with $CH_2Cl_2$. The extracts were washed with water and brine, dried ($MgSO_4$) and concentrated. Chromatography of the residue on silica gel with 5% MeOH—$CHCl_3$ gave 0.58 g of 33: MS(ES) m/z 328 (M+H$^+$), 350 (M+Na$^+$); $^1$H NMR [300 MHz, $(CD_3)_2SO$] d 2.81 (m, 4H), 3.01 (m, 2H), 3.16 (m, 2H), 3.30 (broad s), 3.49 (m, 2H), 3.80 (d,d, 1H), 4.01 (t, 1H), 4.58 (m, 1H), 7.19 (m, 2H), 7.51 (m, 1H).

4.

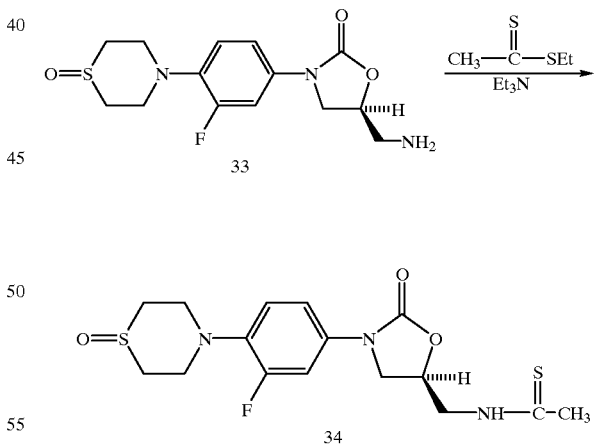

A stirred suspension of 33 (3.7 g, 0.011 mol) and triethylamine (3.5 mL, 0.025 mol) in THF (120 mL) was cooled, in an ice bath, under nitrogen, treated, dropwise during 2 min, with a solution of ethyl dithioacetate (1.47 mL, 0.0128 mol) in THF (2 mL) and kept at ambient temperature for 22 h. The resulting solution was concentrated and the residue crystallized from acetonitrile to give 3.61 g of 34: mp 176–177° C.; $^1$H NMR [300 MHz, $(CD_3)_2SO$] d 2.42 (s, 3H), 2.85 (m, 2H), 3.01 (m, 2H), 3.18 (m, 3H), 3.50 (m, 2H), 3.78 (d,d, 1H), 3.89 (broad s, 2H), 4.12 (t, 1H), 4.92 (m, 1H), 7.18 (m, 2H), 7.49 (m, 1H), 10.33 (s, 1H); IR (DRIFT) 3186, 3102, 1741 cm$^{-1}$; MS(ES) m/z 386 (M+H$^+$), 408 (M+Na$^+$). Anal. calcd for $C_{16}H_{20}FN_3O_3S_2 \cdot 0.5\ H_2O$: C, 48.71; H, 5.37; N, 10.65; S, 16.26; $H_2O$, 2.38. Found: C, 48.75; H, 5.17; N, 10.72; S, 16.07; $H_2O$, 1.72.

EXAMPLE 28

(S)-N-[[3-[3-Fluoro-4-(4-thiomorpholinyl)phenyl]-2-oxo-5-oxazolidinyl]methyl]thio-acetamide, thiomorpholine S, S-dioxide (36)

1.

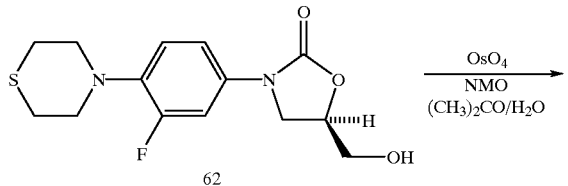

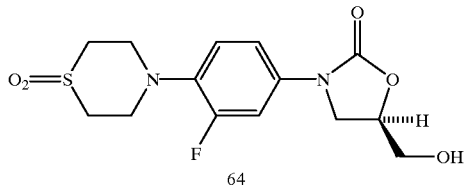

A stirred mixture of 62$^{16}$ (0.399 g, 0.00128 mol) in 25% water/acetone (12 mL), under nitrogen was treated with N-methylmorpholine, N-oxide (0.45 g, 0.00384 mol) and 0.1 mL of a 2.5 wt % solution of osmium tetroxide in tert-butanol. It was kept at ambient temperature for 18 h, mixed with saturated NaHSO$_3$ (50 mL) and extracted with CH$_2$Cl$_2$. The extract was washed with saturated NaHSO$_3$ and brine, dried (Na$_2$SO$_4$) and concentrated. The residue was mixed with 3.5% MeOH—CH$_2$Cl$_2$ and filtered; the solid was dissolved in 15% MeOH—CH$_2$Cl$_2$ and concentrated to give 0.29 g of 64. The filtrate was chromatographed on silica gel with 3.5% MeOH—CH$_2$Cl$_2$ to give 0.1 of additional 64: MS(ES) m/z 345 (M+H$^+$), 367 (M+Na$^+$); $^1$H NMR [300 MHz, (CD$_3$)$_2$SO] d 3.26 (m, 4H), 3.44 (m, 4H), 3.60 (m, 2H), 3.80 (d,d, 1H), 4.05 (t, 1H), 4.69 (m, 1H), 7.22 (m, 2H), 7.54 (d, 1H).

2.

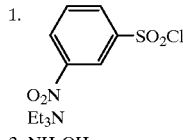

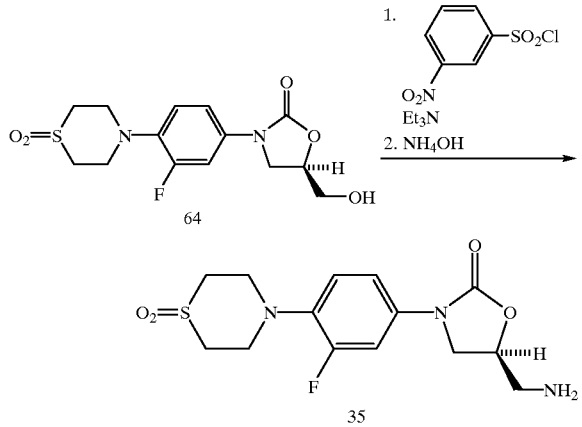

A stirred mixture of 64 (0.39 g, 0.00113 mol) and triethylamine (0.214 mL, 0.00154 mol) in CH$_2$Cl$_2$ (37 mL) was cooled, under nitrogen, in an ice bath and treated, portionwise during 5 min, with 3-nitrobenzenesulfonyl chloride (0.335 g, 0.00151 mol). The mixture was kept in the ice bath for 20 min and at ambient temperature for 18 h and concentrated in vacuo. A stirred solution of the residue in 2-propanol (25 mL) and acetonitrile (25 mL), under nitrogen, was treated with 30% NH$_4$OH (25 mL), warmed at 50–55° C. for 6 h and kept at ambient temperature for 48 h. It was concentrated to remove the organic solvents, diluted with water and extracted with CH$_2$Cl$_2$. The extract was washed with water and brine, dried (MgSO$_4$) and concentrated. Flash chromatography of the residue on silica gel with 6% MeOH-0.4% NH$_4$OH—CHCl$_3$ gave 0.29 g of 35: $^1$H NMR [300 MHz, (CD$_3$)$_2$SO] d 1.59 (broad s, 2H), 2.78 (m, 2H), 3.24 (m, 4H), 3.43 (m, 4H), 3.81 (d,d, 1H), 4.01 (t, 1H), 4.57 (m, 1H), 7.18 (m, 2H), 7.52 (m, 1H); MS(ES) m/z 344 (M+H$^+$), 366 (M+Na$^+$).

3.

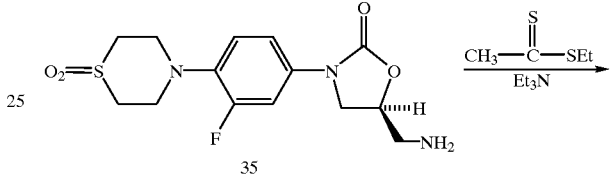

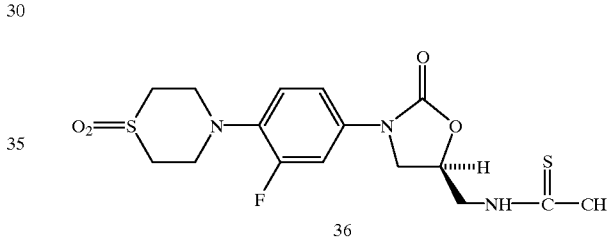

A stirred, ice cold suspension of 35 (0.28 g, 0.85 mmol) in a mixture of Et$_3$N (0.26 mL, 1.9 mmmol) and THF (10 mL) was treated with ethyl dithioacetate (0.11 mL, about 6 drops) and kept in the ice bath for 20 min and then at ambient temperature; the reaction was followed by TLC. After 20 h there was still a suspension and only partial reaction; additional THF (10 mL) and ethyl dithioacetate (3 drops) were added. After an additional 48 h the reaction was still incomplete; the suspension was treated with CH$_2$Cl$_2$ (10 mL) and kept for 72 h. At this time almost complete solution and an almost complete conversion to product had been obtained. An additional drop of ethyl dithioacetate was added and the mixture was kept at ambient temperature for 5 d and concentrated in vacuo. The residue was mixed with EtOAc, washed with saturated NaHCO$_3$, water and brine, dried (MgSO$_4$) and concentrated. Crystallization of the residue from MeOH—EtOAc gave 0.209 g of 36: mp 197–198° C.; $^1$H NMR [300 MHz, (CD$_3$)$_2$SO] d 2.42 (s, 3H), 3.24 (m, 4H), 3.43 (m, 4H), 3.78 (d,d, 1H), 3.88 (m, 2H), 4.12 (t, 1H), 4.92 (m, 1H), 7.18 (m, 2H), 7.50 (m, 1H), 10.37 (broad s, 1H); IR (mull) 3300, 3267, 1743 cm$^{-1}$; MS(ES) m/z 424 (M+Na$^+$). Anal. calcd for C$_{16}$H$_{20}$FN$_3$O$_4$S$_2$: C, 47.87; H, 5.02; N, 10.47. Found: C, 47.84; H, 5.23; N, 10.28.

EXAMPLE 29

(S)-N-[[3-[3,5-Difluoro-4-[4-(hydroxyacetyl)-1-piperazinyl]phenyl]-2-oxo-5-oxazolidinyl]methyl]thioacetamide (38)

3.

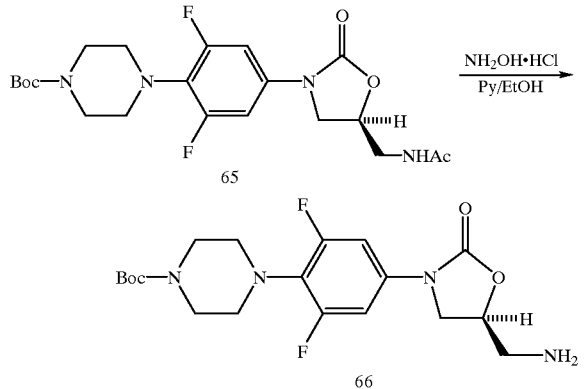

A stirred mixture of 65[17,18] (1.8 g, 0.00396 mol), pyridine (30 mL) and absolute EtOH (3 mL), under nitrogen, was treated with hydroxylamine hydrochloride (1.44 g, 0.0207 mol), warmed to the reflux temperature during 2 h, refluxed for 3.5 h, kept at ambient temperature for 18 h and at reflux for 4 h. It was concentrated in vacuo and the residue was mixed with water, adjusted to pH 11 with saturated NaHCO$_3$ and extracted with Et$_2$O. The extracts were washed with brine, dried (Na$_2$SO$_4$) and concentrated. Chromatography of the residue on silica gel with 5% MeOH-0.35%, NH$_4$OH—CHCl$_3$ gave 0.75 g of recovered 65 and 0.72 g of 66: $^1$H NMR [300 MHz, (CD$_3$)$_2$SO] d 1.40 (s, 9H), 1.72 (broad s, 2H), 2.78 (m, 2H), 2.97 (m, 4H), 3.40 (m, 4H), 3.80 (d,d, 1H), 4.00 (t, 1H), 4.59 (m, 1H), 7.27 (d, 2H); MS(ES) m/z 413 (M+H$^+$), 435 (M+Na$^+$).

2.

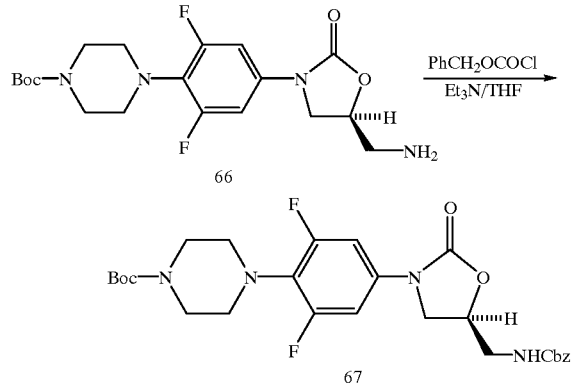

An ice cold, stirred mixture of 66 (0.75 g, 0.0018 mol) and triethylamine (0.315 mL, 0.00225 mol) in THF (12 mL), under nitrogen, was treated, dropwise with benzyl chloroformate (0.29 mL, 0.0020 mol), kept in the ice bath for 15 min and at ambient temperature for 2 h and concentrated in vacuo. The residue was mixed with CH$_2$Cl$_2$ and washed with saturated NaHCO$_3$, water and brine, dried (Na$_2$SO$_4$) and concentrated. This residue was mixed with Et$_2$O and filtered to give 0.939 g of 67: mp 116–118° C.; $^1$H NMR (300 MHz, CDCl) d 1.48 (s, 9H), 3.08 (m, 4H), 3.53 (m, 4H), 3.60 (m, 2H), 3.73 (m, 1H), 3.96 (t, 1H), 4.76 (m, 1H), 5.10 (s, 2H), 5.21 (m, 1H), 7.07 (d, 2H), 7.31 (s, 5H); MS(ES) m/z 547 (M+H$^+$), 569 (M+Na$^+$).

3.

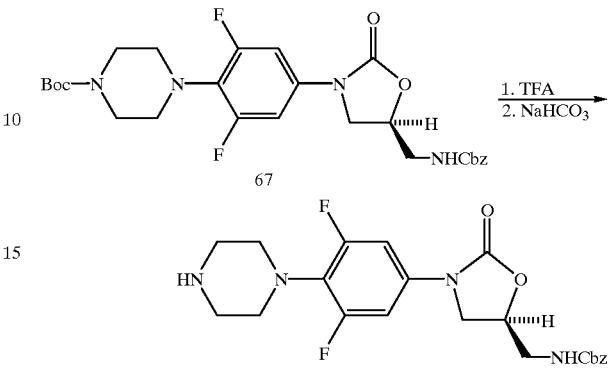

Compound 67 (0.805 g, 0.00147 mol) was added with stirring, portionwise during 5 min, under nitrogen, to ice cold trifluoroacetic acid (9 mL). The resulting solution was kept in the ice bath for 1 h and then concentrated under a stream of nitrogen.

The residue was mixed with ice and saturated NaHCO$_3$ and extracted with CH$_2$Cl$_2$; the extract was washed with water and brine, dried (Na$_2$SO$_4$) and concentrated to give 0.63 g of product. The combined aqueous layer was reextracted with EtOAc; the extracts were washed with water and brine, dried (Na$_2$SO$_4$) and concntrated to give additional product. The combined product amounted to 0.68 g of 68 which was used in the next reaction without further purification.

4.

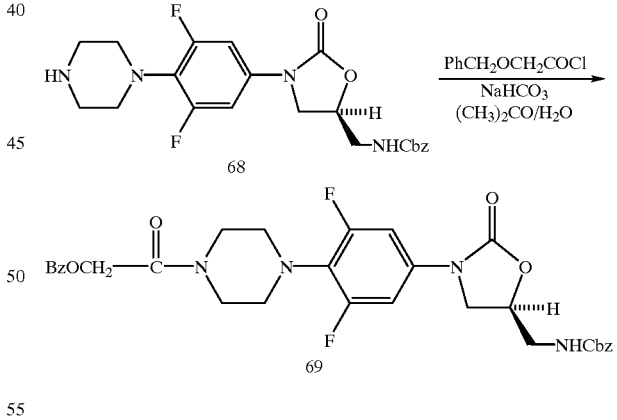

An ice cold, stirred mixture of 68 (0.68 g, 0.00152 mol), saturated NaHCO$_3$ (15.2 mL) and acetone (40 mL), under nitrogen was treated, dropwise during 15 min, with a solution of benzyloxyacetyl chloride (0.29 mL, 0.0019 mol) in acetone (5 mL), kept at ambient temperature for 6 h, diluted with EtOAc and washed with water and brine. The extract was dried (MgSO$_4$) and concentrated in vacuo to give 0.72 g of 69: MS(ES) m/z 395 (M+H$^+$), 617 (M+Na$^+$); 1H NMR (300 MHz, CDCl$_3$) d 3.12 (m, 4H), 3.59 (m, 4H), 3.74 (m, 3H), 3.96 (t, 1H), 4.22 (s, 2H), 4.62 (s, 2H), 4.75 (broad s, 1H), 5.10 (s, 2H), 5.22 (m, 1H), 7.08 (d, 2H), 7.33 (m, 10H).

5.

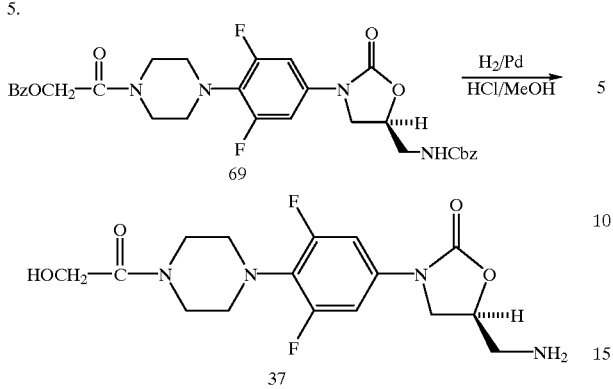

A mixture of 69 (0.72 g, 0.0012 mol), MeOH and 5% palladium-on-carbon catalyst (0.4 g) was hydrogenated at an initial pressure of 45 psi for 4 h. By TLC (8% MeOH-0.5% NH$_4$OH—CHCl$_3$) the starting material had been reduced and two products formed. 1M Hydrochloric acid (1.34 mL) was added and hydrogenation was continued at an initial pressure of 40 psi for 21 h. By TLC only the more polar product remained. The catalyst was removed by filtration and the filtrate was concentrated to give 0.40 g of 37: MS(ES) m/z 371 (M+H$^+$), 393 (M+Na$^+$); $^1$H NMR [300 MHz, (CD$_3$)$_2$SO] d 3.02 (s, 4H), 3.20 (m, 2H), 3.43 (s, 2H), 3.56 (s, 2H), 3.84 (m, 1H), 3.84 (broad s), 4.10 (s, 2H), 4.14 (t, 1H), 4.96 (m, 1H), 7.26 (d, 2H), 8.41 (broad s, 3H).

6.

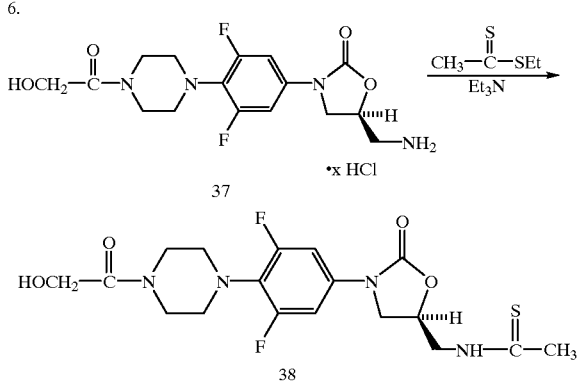

A stirred suspension of 37 (0.38 g) in a solution of Et$_3$N (0.31 mL) and THF (10 mL), under nitrogen, was treated with ethyl dithioacetate (0.13 mL, about 7 drops) and kept at ambient temperature for 7 d; the reaction was followed by TLC (8% MeCH-0.5% NH$_4$OH—CHCl$_3$). Additional ethyl dithioacetate (2 drops) was added after 24 h; after 30 h CH$_2$Cl$_2$ (10 mL) and ethyl dithioacetate (3 drops) were added; after 48 h additional triethylamine (0.3 mL) was added. The mixture was concentrated in vacuo and the residue was mixed with ice and saturated NaHCO$_3$ an extracted with CH$_2$Cl$_2$. The extract was washed with water and brine, dried (MgSO$_4$) and concentrated. The residue was chromatographed on silica gel with 2.5% MeOH-CH$_2$Cl$_2$ and the product was crystallized from MeOH to give 0.182 g of 38: mp 110–111° C. (dec); MS(ES) m/z 429 (M+H$^+$), 451 (M+Na$^+$); HRMS (FAB) calcd for C$_{18}$H$_{23}$F$_2$N$_4$O$_4$S (M+H$^+$) 429.1408, found 429.1415; IR (DRIFT) 1760, 1652, 1639 cm$^{-1}$; [$\alpha$]$^{24}_D$ 8° (MeOH).

EXAMPLE 30

(S)-N-[[3-[4-[1-[1,2,4]Triazolyl]phenyl]-2-oxo-5-oxazolidinyl]methyl]thiourea (44)

1.

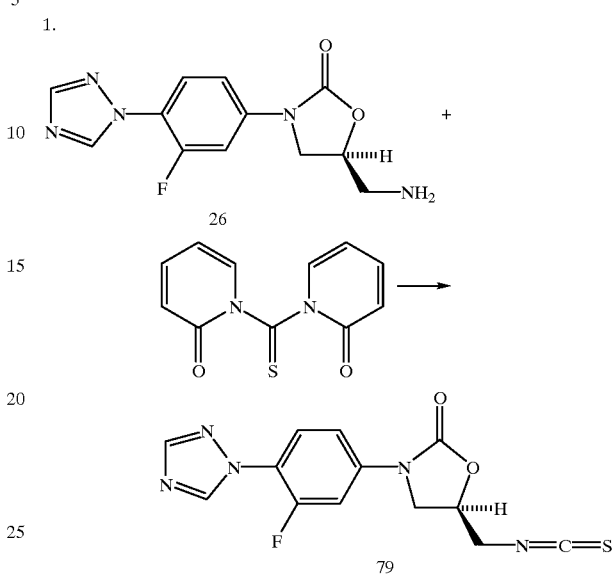

A solution of 26 (0.190 g, 0.685 mmol) in CH$_2$Cl$_2$ (20 mL) was added, dropwise during 20 min, under nitrogen, to an ice cold, stirred solution of 1,1¢-thiocarbonyldi-2(1H)-pyridone (0.193 g, 0.831 mmol) in CH$_2$Cl$_2$ (7 mL). The mixture was kept in the ice bath for 20 min and at ambient temperature for 2 h, diluted with CH$_2$Cl$_2$, washed with water and brine, dried (MgSO$_4$) and concentrated. Chromatography of the residue on silica gel with 10–15% CH$_3$CN—CH$_2$Cl$_2$ gave 0.11 g of 79 which was used in the next reaction without further purification: MS(ES) m/z 320 (M+H$^+$), 342 (M+Na$^+$).

2.

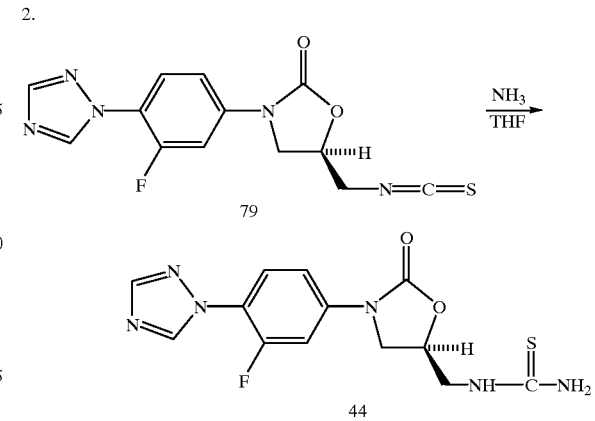

A stirred, ice cold solution of 79 (0.10 g, 0.31 mmol) in THF (15 mL) was treated with excess anhydrous ammonia and kept in the ice bath for 90 min. It was then evaporated under a stream of nitrogen to a volume of about 5 mL to give a solid which was collected by filtration and washed with cold THF to give 0.105 g of 44: mp 214–215° C.; $^1$H NMR [300 MHz, (CD$_3$)$_2$SO] d 3.82 (m, 3H), 4.18 (t, 1H), 4.89 (broad s, 1H), 7.20 (broad s, 2H), 7.50 (d, 1H), 7.79 (m, 2H), 7.93 (t, 1H), 8.26 (s, 1H), 8.97 (s, 1H); MS(ES) m/z 337

(M+H⁺), 359 (M+Na⁺). Anal. calcd for $C_{13}H_{13}FN_6O_2S$: C, 46.42; H, 3.90; N, 24.99. Found: C, 46.22; H, 3.98; N, 24.55.

EXAMPLE 31

(S)-N-[[3-[3-Fluoro-4-[4-(hydroxyacetyl)-1-piperazinyl]phenyl]-2-oxo-5-oxazolidinyl]-methyl]thiourea (45)

1.

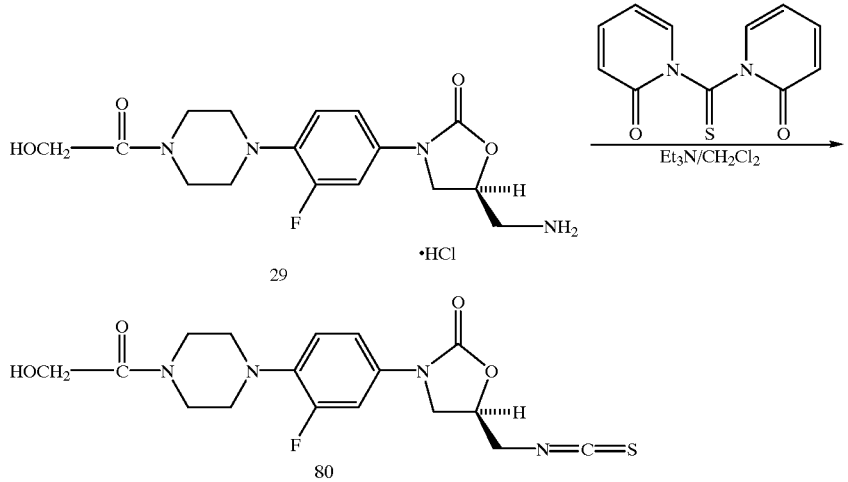

An ice cold, stirred solution of 1,10-thiocarbonyl-2(1H)-dipyridone (0.123 g, 0.530 mmol) in $CH_2Cl_2$ (5 mL), under nitrogen, was treated with a suspension of 29 (0.17 g, 0.4 mmol) in $CH_2Cl_2$ (20 mL) and then during 10 min with a solution of triethylamine (0.111 mL, 0.8 mmol) in $CH_2Cl_2$ (10 mL). It was kept in the ice bath for 30 min, at ambient temperature for 2 h and at <0° C. for 18 h. It was then diluted with $CH_2Cl_2$, washed with water and brine, dried ($MgSO_4$) and concentrated. The residue (80) was used without further purification in the next reaction. A sample of 80 that was purified by flash chromatography on silica gel with 10–20% acetonitrile—$CH_2Cl_2$ had: $^1H$ NMR (300 MHz, $CDCl_3$) d 1.60 (broad s), 3.07 (m, 4H), 3.45 (m, 2H), 3.85 (m, 4H), 3.97 (d,d, 1H), 4.16 (t, 1H), 4.21 (s, 2H), 4.82 (m, 1H), 6.95 (t, 1H), 7.13 (d,d, 1H), 7.47 (d,d, 1H); MS m/z 395 (M+H⁺); 417 (M+Na⁺).

2.

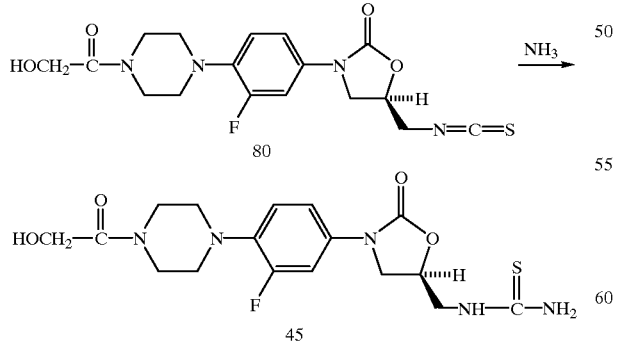

Excess anhydrous ammonia was bubbled into a stirred, ice cold solution of 80 (crude product from the previous reaction) in THF (25 mL) and the mixture was kept in the ice bath for 90 min and concentrated under a stream of nitrogen.

The residue was chromatographed on silica gel with 5% MeOH-0.4% $NH_4OH$—$CHCl_3$ and the product was crystallized from acetonitrile to give 0.0544 g of 45: mp 209–210° C.; $^1H$ NMR [300 MHz, $(CD_3)_2SO$] d 294 (broad s, 4H), 3.47 (broad s, 2H), 3.60 (broad s, 2H), 3.78 (broad s, 3H), 4.07 (t, 1H), 4.10 (d, J=5.5 Hz, 2H), 4.63 (t, J=5.5 Hz, 1H), 4.81 (broad s, 1H), 7.05 (t, 1H), 7.16 (d,d, 1H), 7.15 (broad s, 2H), 7.49 (d,d, 1H), 7.91 (t, 1H); IR (mull) 3443, 3403, 3321, 3202, 3081, 1753, 1655, 1648 cm⁻¹; HRMS (FAB) calcd for $C_{17}H_{23}FN_5O_4S$ (M+H⁺) 412.1454, found 412.1447. Anal. calcd for $C_{17}H_{22}FN_5O_4S$: C, 49.63; H, 5.39; N, 17.02. Found: C, 49.63; H, 5.48; N, 16.99.

EXAMPLE 32

(S)-N-[[3-[1-(Hydroxyacetyl)-5-indolinyl]-2-oxo-5-oxazolidinyl]methyl]thiourea (46)

1.

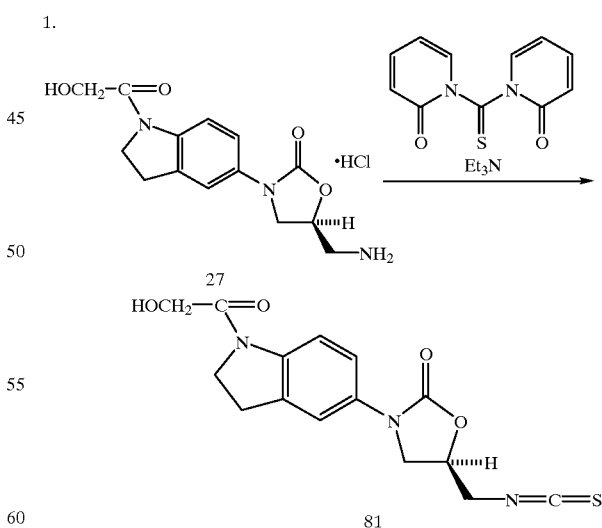

An ice cold, stirred solution of 1,1¢-thiocarbonyldi-2(1H)-pyridone (0.096 g, 0.41 mmol) in $CH_2Cl_2$ (5 mL) was treated with a suspension of 27 (0.10 g, 0.34 mmol) in $CH_2Cl_2$ (15 mL) and then with 0.05 mL (0.36 mmol) of triethylamine. It was kept in the ice bath for 30 min and at ambient temperature for 2 h, diluted with CH$_2$Cl$_2$, washed with water and brine, dried (MgSO$_4$) and concentrated. Chromatography of the residue on silica gel with 20–40% CH$_3$CN—CH$_2$Cl$_2$ gave 0.04 g of 81.

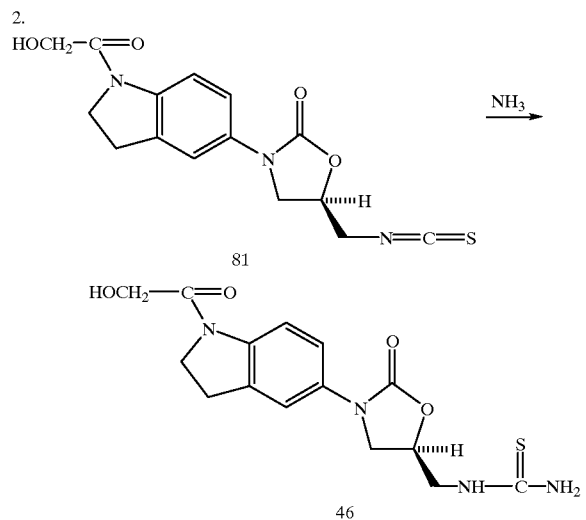

Excess anhydrous ammonia was bubbled into an ice cold solution of 81 (0.04 g) in THF (30 mL) and the mixture was kept in the ice bath for 80 min and concentrated under a stream of nitrogen. The residue was crystallized from CH$_3$CN to give 0.0151 g of 46: mp 214–215° C. (dec); MS (FAB) m/z 351 (M+H$^+$), 350 (M$^+$), 319, 304, 147; HRMS (FAB) calcd for C$_{15}$H$_{19}$N$_4$O$_4$S (M+H$^+$) 351.1127, found 351.1100; IR (DRIFT) 3329, 3296, 3196, 1746, 1655, 1626 cm$^{-1}$.

EXAMPLE 33

(S)-N-[[3-[3-Fluoro-4-(4-thiomorpholinyl)phenyl]-2-oxo-5-oxazolidinyl]methyl]thiourea, thiomorpholine S-oxide (47)

1.

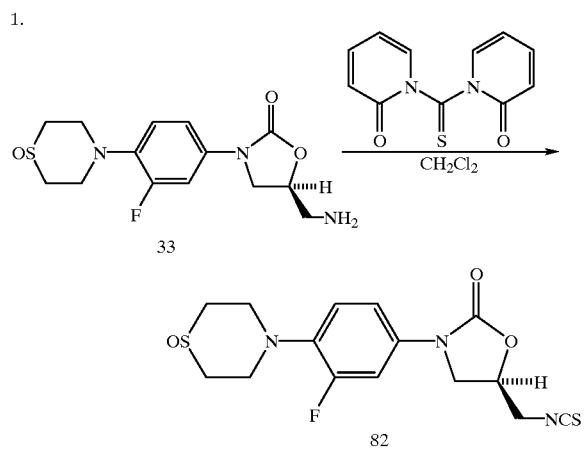

A suspension of 33 (0.30 g, 0.92 mmol) in CH$_2$Cl$_2$ (7 mL) was added, during 20 min, to an ice cold, stirred mixture of 1,1¢-thiocarbonyldi-2(1H)-pyridone (0.258 g, 1.11 mmol) and CH$_2$Cl$_2$ (20 mL). The mixture was kept in the ice bath for 20 min and at ambient temperature for 2 h, mixed with CH$_2$Cl$_2$ (50 mL), washed with water and brine, dried (MgSO$_4$) and concentrated. Chromatography of the product on silica gel with 20–50% CH$_3$CN—CH$_2$Cl$_2$ gave 0.27 g of 82 which was used in the next reaction: MS(ES) m/z 370 (M+H$^+$), 392 (M+Na$^+$).

2.

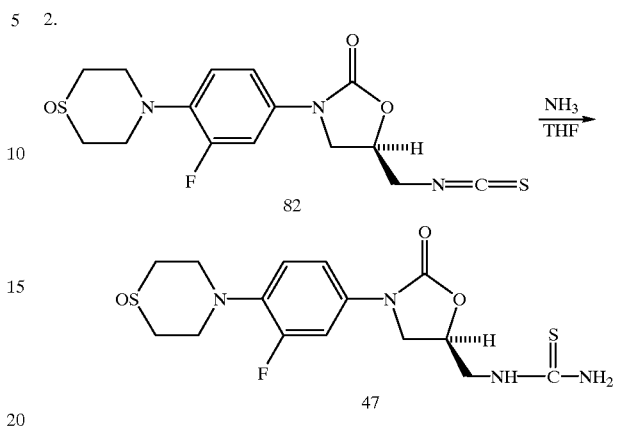

A stirred, ice cold solution of 82 (0.27 g, 0.73 mmol) in THF (15 mL), under nitrogen, was treated with excess anhydrous ammonia, kept in the ice bath for 1 h and concentrated; crystallization of the residue from MeOH gave 0.175 g of 47; mp 212–213° C.; $^1$H NMR [300 MHz, (CD$_3$)$_2$SO] d 2.83 (m, 2H), 3.01 (m, 2H), 3.17 (m, 2H), 3.50 (t, 2H), 3.78 (broad s, 3H), 4.08 (t, 1H), 4.80 (broad s, 1H), 7.17 (m, 2H), 7.17 (broad s, 2H), 7.50 (d, 1H), 7.90 (t, 1H); MS(ES) m/z 409 (M+Na$^+$); IR (mull) 3335, 3284, 3211, 3175, 3097, 1750, 1630 cm$^{-1}$. Anal. calcd for C$_{15}$H$_{19}$FN$_4$O$_3$S$_2$: C, 4(46.62; H, 4.95; N, 14.50. Found: C, 46.50; H, 4.95; N, 14.40.

EXAMPLE 34

(S)-N-[[3-[3-Fluoro-4-(4-morpholinyl)phenyl]-2-oxo-5-oxazolidinyl]methyl—S-methyldithiocarbamate (48)

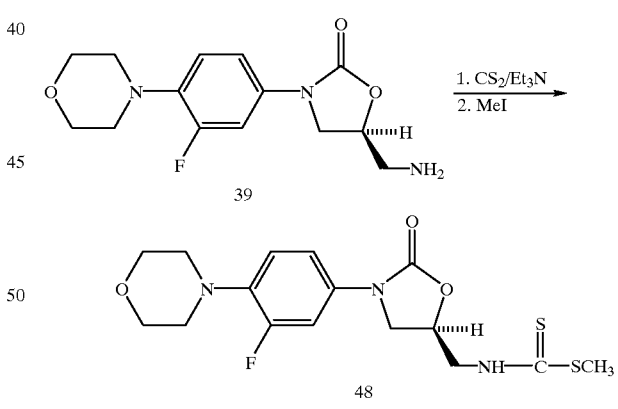

An ice cold, stirred mixture of 39$^8$ (0.59 g, 0.0020 mol), EtOH (1.5 mL), water (2 drops) and triethylamine (0.613 mL, 0.00440 mol), under nitrogen, was treated with carbon disulfide (0.066 mL, 0.0011 mol) and kept in the ice bath for 2 h and at ambient temperature for 18 h. (A solution was obtained after the addition of carbon disulfide; a white precipitate began to form soon after the mixture was warmed to ambient temperature.) The thick suspension was treated, dropwise during 2 min, with a solution of methyl iodide (0.137 mL, 0.00220 mol) in EtOH (2 mL) and the mixture was kept at ambient temperature for 1.5 h and concentrated in vacuo. A solution of the residue in EtOAc was washed with saturated NaHCO₃, water and brine, dried (MgSO₄) and concentrated. The residue was chromatographed on silica gel with 1.8% MeOH—CH₂Cl₂ and the product was crystallized from EtOAc to give 0.197 g of 48: mp 154–156° C.; IR (mull) 3354, 3346, 1726 cm⁻¹. Anal. calcd for $C_{16}H_{20}FN_3O_3S_2$: C, 49.85; H, 5.23; N, 10.90. Found: C, 49.73; H, 5.25; N, 10.82.

EXAMPLE 35

(S)-N-[[3-[3-Fluoro-4-(4-morpholinyl)phenyl]-2-oxo-5-oxazolidinyl]methyl-O-methylthiocarbamate (50)

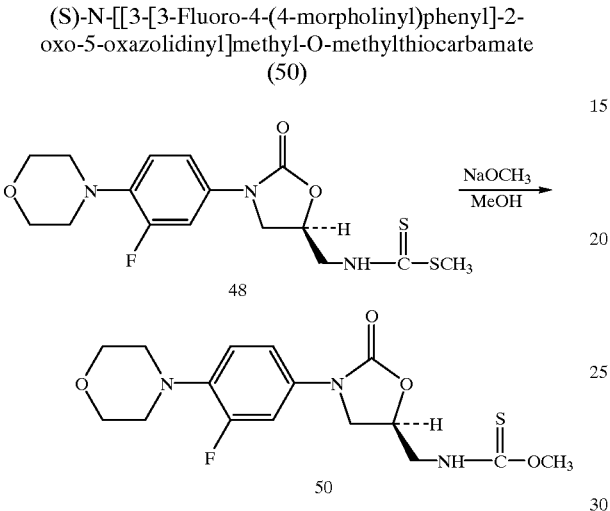

A stirred mixture of 48 (0.200 g, 0.518 mmol), sodium methoxide (0.003 g, 0.06 mmol) and MeOH (5 mL), under nitrogen, was refluxed for 4 h and kept at ambient temperature for 18 h. It was found that the starting material and product had similar mobilities on TLC. the reaction was therefore followed by MS(ES). Starting material was still present. The mixture was refluxed for 3 h, additional sodium methoxide (0.005 g) was added and reflux was continued for 2 h. It was kept at ambient temperature for 18 h, refluxed for 1 h, kept at ambient temperature 1.5 h and concentrated in vacuo. The residue was mixed with ice, the pH was adjusted to 9–10 with 1M KHSO₄ and saturated NaHCO₃ and the mixture was extracted with CH₂Cl₂. The extract was washed with water and brine, dried (MgSO₄) and concentrated. The residue was chromatographed on silica gel with 5% acetone-CH₂Cl₂ and the product was crystallized from EtOAc-hexane to give 0.107 g of 50: mp 128–129° C.; MS(ES) m/z 370 (M+H⁺), 392 (M+Na⁺); IR (DRIFT) 3282, 3251, 1753, 1735 cm⁻¹; ¹H NMR [300 MHz, (CD₃)₂SO] d 2.94 (m, 4H), 3.47, 374 (m,m, 7H), 3.86, 3.91 (s,s, 3H), 4.10 (m, 1H), 4.73, 4.86 (m,m, 1H), 7.05 (t, 1H), 7.16 (d,d, 1H), 7.47 (d,d, 1H), 9.41, 9.50 (s,s, 1H). Anal. calcd for $C_{16}H_{20}FN_3O_4S$: C, 52.02; H, 5.46; N, 11.38. Found: C, 51.97; H, 5.49; N, 11.35.

What is claimed:

1. A compound of the formula I or a pharmaceutical acceptable salt thereof wherein:

G is

R₁ is
a) H,
b) NH₂,
c) NHC₁₋₄alkyl,
d) C₁₋₄alkyl,
e) —OC₁₋₄ alkyl,
f) —SC₁₋₄ alkyl,
g) C₁₋₄ alkyl substituted with one to three fluoro, one to two chloro, CN or —COOC₁₋₄ alkyl,
h) C₃₋₆cycloalkkyl,
i) N(C₁₋₄alkyl)₂, or
j) N(CH₂)₂₋₅;

A is

R₂₃ and R₂₄ are independently
a) H,
b) F,
c) Cl,
d) C₁₋₂alkyl,
e) CN,
f) OH,
g) C₁₋₂alkoxy,
h) nitro, or
i) amino;

Q is

E is
a) —S(=O)ᵢ—, or
b) —O—;

R₃₈ is
a) H,
b) C₁₋₆alkyl, or
c) halo;

the dotted line ---- in the ring system of Q is a single or double bond with the proviso that when ---- is a double bond, R₃₈ is absent;

i is 0, 1, or 2;

n is 0, 1, 2, 3, 4, or 5; and p is 0, 1, 2, 3, 4, or 5; with the proviso that n and p taken together is 1, 2, 3, 4 or 5.

2. A compound of formula I as shown in claim 1 which is

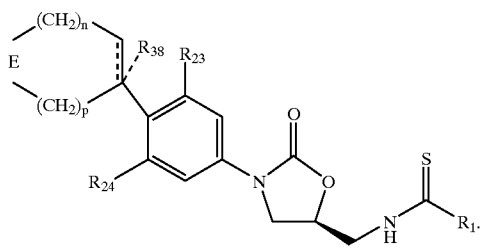

3. A compound of claim 2 wherein $R_{23}$ and $R_{24}$ are independently H or F; wherein $R_{38}$ is hydrogen or absent.

4. A compound of claim 3 wherein E is —$SO_2$—, —SO—, or —S—.

5. A compound of claim 3 wherein E is —O—.

6. A compound of claim 4 wherein n and p taken together is 3.

7. A compound of claim 5 wherein n and p taken together is 3.

8. A compound of claim 6 wherein $R_1$ is
a) H,
b) $NH_2$,
c) $C_{1-4}$ alkyl,
d) —$OC_{1-4}$ alkyl,
e) —$SC_{1-4}$ alkyl,
f) $C_{1-4}$ alkyl substituted with one to two Cl, or
g) $C_{3-6}$cycloalkyl.

9. A compound of claim 7 wherein $R_1$ is
a) H,
b) $NH_2$,
c) $C_{1-4}$ alkyl,
d) —$OC_{1-4}$ alkyl,
e) —$SC_{1-4}$ alkyl,
f) $C_{1-4}$ alkyl substituted with one to two Cl, or
g) $C_{3-6}$cycloalkyl.

10. A compound of claim 2 which is
(a) (S)-cis-N-[[3-[3-fluoro-4-(tetrahydro-l1-oxido-2H-thiopyran-4-yl)phenyl]-2-oxo-5-oxazolidinyl]methyl]ethanethioamide;
(b) (S)-cis-[[3-[3-fluoro-4-(tetrahydro-l1-oxido-2H-thiopyran-4-yl)phenyl]-2-oxo-5-oxazolidinyl]methyl]thiourea;
(c) (S)-trans-N-[[3-[3-Fluoro-4-(tetrahydro-1-oxido-2H-thiopyran-4-yl)phenyl)-2-oxo-5-oxazolidinyl]methyl]ethanethioamide;
(d) (S)-trans-[[3-[3-Fluoro-4-(tetrahydro-1-oxido-2H-thiopyran-4-yl)phenyl]-2-oxo-5-oxazolidinyl]methyl]thiourea;
(e) (S)-N-[[3-[3-Fluoro-4-(tetrahydro-1, 1 -dioxido-2H-thiopyran-4-yl)phenyl]-2-oxo-5-oxazolidinyl]methyl]ethanethioami; or
(f) (S)-N-[[3-[3-Fluoro-4-(tetrahydro- 1,1 -dioxido-2H-thiopyran4-yl)phenyl]-2-oxo-5-oxazolidinyl]methyl]thiourea.

11. A method for treating microbial infections in humans and other warm blooded animals comprising administering to humans and other warm blooded animals in need for such treatment thereof an effective amount of a compound of formula I as shown in claim 1.

12. The method of claim 11 wherein said compound of formula I is administered orally, parenterally, or topically.

13. The method of claim 11 wherein said compound is administered in an amount of from about 0.1 to about 100 mg/kg of body weight/day.

14. The method of claim 11 wherein said compound is administered in an amount of from about 1 to about 50 mg/kg of body weight/day.

15. A pharmaceutical composition comprising a compound of claim 1 and a pharmaceutically acceptable carrier.

* * * * *